(12) United States Patent
Kling et al.

(10) Patent No.: US 7,105,508 B1
(45) Date of Patent: Sep. 12, 2006

(54) INTEGRIN RECEPTORS ANTAGONISTS

(75) Inventors: Andreas Kling, Mannheim (DE); Hervé Geneste, Neuhofen (DE); Udo Lange, Mannheim (DE); Arnulf Lauterbach, Ludwigshafen (DE); Claudia Isabella Graef, Mannheim (DE); Thomas Subkowski, Ladenburg (DE); Uta Holzenkamp, Lambsheim (DE); Helmut Mack, Ludwigshafen (DE); Jens Sadowski, Limburgerhof (DE); Wilfried Hornberger, Neustadt (DE); Volker Laux, Mainz (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 115 days.

(21) Appl. No.: 10/049,266

(22) PCT Filed: Aug. 1, 2000

(86) PCT No.: PCT/EP00/07440

§ 371 (c)(1),
(2), (4) Date: Sep. 9, 2002

(87) PCT Pub. No.: WO01/10847

PCT Pub. Date: Feb. 15, 2001

(30) Foreign Application Priority Data

Aug. 9, 1999 (DE) .............................. 199 36 780

(51) Int. Cl.
*C07D 401/12* (2006.01)
*A61K 31/55* (2006.01)

(52) U.S. Cl. .................. 514/212.04; 540/522
(58) Field of Classification Search ................ 540/522; 514/212.04
See application file for complete search history.

(56) References Cited

FOREIGN PATENT DOCUMENTS

| JP | 61-167663 | 1/1985 |
|---|---|---|
| WO | WO 97/01540 A1 | 1/1997 |
| WO | WO 98/30542 | 7/1998 |
| WO | WO 98/30542 A1 | 7/1998 |
| WO | WO 99/05107 A1 | 2/1999 |
| WO | WO 99/11626 | 3/1999 |
| WO | WO 99/11626 A1 | 3/1999 |
| WO | WO 99/15508 A1 | 4/1999 |
| WO | WO 99/37651 | 7/1999 |

OTHER PUBLICATIONS

E. Ruoslahti et al., Cell 1986, 44, 517-518.
E. Ruoslahti et al., Science 1987, 238, 491-497.
L. Piali et al., J. Cell Biol. 1995, 130, 517-518.
C. D. Buckley et al., J. Cell Science 1996, 109, 437-445.
M. L. Kireeva et al., J. Biol. Chem. 1998, 273, 3090-3096.
E. T. Choi et al., J. Vasc. Surg. 1994, 19, 125-134.
H. Matsuno et al., Circulation 1994, 90, 2203-2206.
E. Noiri et al., Kidney Int. 1994, 46, 1050-1058.
M. S. Goligorsky et al., Proc. Natl. Acad. Sci. 1993, 90, 5700-5704.
E. Noiri et al., Kidney Int. 1995, 48, 1375-1385.
P.A. D'Amore et al., Ann. Rev. Physiol 1987, 49, 453-464.
G. C. Brown et al., Int. Ophthalmol. 1987, 11, 41-50.
P.C. Brooks et al., Cell 1994, 79, 1157-1164.
J. Folkman et al., J. Biol. Chem. 1992, 267, 10931-10934.
L. A. Liotta et al., Cell 1991, 64, 327-336.
J. Folkman et al., Nature 1989, 339, 58-61.
M. Friedlander et al., Science 1995, 270, 1500-1502.
D. T. Denhardt et al., FASEB J. 1993, 7, 1475-1482.
M. A. Horton et al., Exp. Cell Res. 1991, 195, 368-375.
M. Aumailley et al, FEBS Letts 1991, 291, 50-54.
M. Pfaff et al., J. Biol. Chem. 1994, 269, 20233-20238.
D. A. Cheresh et al., J. Biol. Chem. 1987, 262, 17703-17711.

*Primary Examiner*—Bruck Kifle
(74) *Attorney, Agent, or Firm*—Wood, Phillips, Katz, Clark & Mortimer

(57) ABSTRACT

The invention relates to novel compounds which bind to integrin receptors, and to the preparation thereof and the use thereof as drugs.

3 Claims, No Drawings

INTEGRIN RECEPTORS ANTAGONISTS

The invention relates to novel compounds which bind to integrin receptors, and to the preparation and use thereof.

Integrins are cell surface glycoprotein receptors which mediate interactions between identical and different cells and between cells and extracellular matrix proteins. They are involved in physiological processes such as, for example, embryogenesis, hemostasis, wound healing, immune response and formation/maintenance of tissue architecture.

Disturbances in the expression of genes of cell adhesion molecules, and disturbances of the function of receptors may contribute to the pathogenesis of many disorders such as, for example, tumors, thromboembolic events, cardiovascular disorders, pulmonary disorders, disorders of the CNS, of the kidney, of the gastrointestinal tract or inflammations.

Integrins are heterodimers each composed of α and β transmembrane subunits, which are linked noncovalently. To date, 16 different a subunits and 8 different β subunits and 24 different combinations have been identified.

Integrin $\alpha_v\beta_3$, also called vitronectin receptor, mediates the adhesion to a large number of ligands—plasma proteins, extracellular matrix proteins, cell surface proteins—most of which contain the amino acid sequence RGD (Cell, 1986, 44, 517–518; Science 1987, 238, 491–497), such as, for example, vitronectin, fibrinogen, fibronectin, von Willebrand factor, thrombospondin, osteopontin, laminin, collagen, thrombin, tenascin, MMP-2, bone sialoprotein II, various viral, parasitic and bacterial proteins, natural integrin antagonists such as disintegrins, neurotoxins—mambin—and leech proteins—decorsin, ornatin—and some non-RGD ligands such as, for example, Cyr-61, PECAM (L. Piali, J. Cell Biol. 1995, 130, 451–460; Buckley, J. Cell Science 1996, 109, 437–445, J. Biol. Chem. 1998, 273, 3090–3096).

Several integrin receptors show cross—reactivity with ligands which contain the RGD motif. Thus, integrin $\alpha_{IIb}\beta_3$, also called platelet fibrinogen receptor, recognizes fibronectin, vitronectin, thrombospondin, von Willebrand factor and fibrinogen.

Integrin $\alpha_v\beta_3$ is expressed inter alia on endothelial cells, blood platelets, monocytes/macrophages, smooth muscle cells, some B cells, fibroblasts, osteoclasts and various tumor cells such as, for example, melanomas, glioblastomas, carcinomas of the lung, breast, prostate and bladder, osteosarcomas or neuroblastomas.

Increased expression is observed under various pathological conditions such as, for example, in the prothrombotic state, when there is vessel injury, tumor growth or metastasis or reperfusion and on activated cells, in particular on endothelial cells, smooth muscle cells or macrophages.

Involvement of integrin $\alpha_v\beta_3$ has been demonstrated inter alia for the following pathologies:

cardiovascular disorders such as atherosclerosis, restenosis after vessel injury, and angioplasty (neointima formation, smooth muscle cell migration and proliferation) (J. Vasc. Surg. 1994, 19, 125–134; Circulation 1994, 90, 2203–2206), acute kidney failure (Kidney Int. 1994, 46, 1050–1058; Proc. Natl. Acad. Sci. 1993, 90, 5700–5704; Kidney Int. 1995, 48, 1375–1385), angiogenesis-associated microangiopathies such as, for example, diabetic retinopathy or rheumatoid arthritis (Ann. Rev. Physiol 1987, 49, 453–464; Int. Ophthalmol. 1987, 11, 41–50; Cell 1994, 79, 1157–1164; J. Biol. Chem. 1992, 267, 10931–10934), arterial thrombosis, stroke (phase II studies with ReoPro, Centocor Inc., 8th annual European Stroke Meeting), cancers such as, for example, in tumor metastasis or in tumor growth (tumor-induced angiogenesis) (Cell 1991, 64, 327–336; Nature 1989, 339, 58–61; Science 1995, 270, 1500–1502), osteoporosis (bone resorption after proliferation, chemotaxis and adhesion of osteoclasts to bone matrix) (FASEB J. 1993, 7, 1475–1482; Exp. Cell Res. 1991, 195, 368–375, Cell 1991, 64, 327–336), high blood pressure, psoriasis, hyperparathyroidism, Paget's disease, malignant hypercalcemia, metastatic osteolytic lesions, inflammation, cardiac insufficiency, CHF, and for antiviral, antiparasitic or antibacterial therapy and prophylaxis (adhesion and internalization).

Because of its key role, pharmaceutical preparations which contain low molecular weight integrin $\alpha_v\beta_3$ antagonists are of great therapeutic and diagnostic benefit inter alia for the indications mentioned.

Advantageous $\alpha_v\beta_3$ integrin receptor antagonists bind to the integrin $\alpha_v\beta_3$ receptor with increased affinity.

Particularly advantageous $\alpha_v\beta_3$ integrin receptor antagonists additionally show increased selectivity for integrin $\alpha_v\beta_3$ and are less effective in relation to integrin $\alpha_{IIb}\beta_3$ by a factor of at least 10, preferably by a factor of at least 100.

A large number of compounds such as anti-$\alpha_v\beta_3$ monoclonal antibodies, peptides containing the RGD binding sequence, natural RGD-containing proteins (for example disintegrins) and low molecular weight compounds have been shown to have an integrin $\alpha_v\beta_3$ antagonistic effect and have demonstrated a beneficial in vivo effect (FEBS Letts 1991, 291, 50–54; J. Biol. Chem. 1990, 265, 12267–12271; J. Biol. Chem. 1994, 269, 20233–20238; J. Cell Biol 1993, 51, 206–218; J. Biol. Chem. 1987, 262, 17703–17711; Bioorg. Med. Chem. 1998, 6, 1185–1208).

Also known are $\alpha_v\beta_3$ antagonists with a tricyclic molecular structure.

WO 9915508-A1, WO 9830542-A1 and WO 9701540-A1 describe dibenzocycloheptane derivatives, WO 9911626-A1 describes dibenzo[1,4]oxazepine derivatives and WO 9905107-A1 describes benzocycloheptane derivatives.

It is an object of the present invention to provide novel integrin receptor antagonists with advantageous properties.

We have found that this object is achieved by compounds of the formula I $$B\text{---}G\text{---}L \qquad \qquad I$$

where B, G and L have the following meanings:
L a structural element of the formula $I_L$

$$\text{---}U\text{---}T \qquad \qquad I_L$$

where
T is a COOH group or a radical which can be hydrolyzed to COOH and
—U— is  —(X$_L$)$_a$—(CR$_L^1$R$_L^2$)$_b$—, —CR$_L^1$=CR$_L^2$—, ethynylene or =CR$_L^1$—, where
a is 0 or 1,
b is 0, 1 or 2
X$_L$ is CR$_L^3$R$_L^4$, NR$_L^5$, oxygen or sulfur,
R$_L^1$, R$_L^2$, R$_L^3$, R$_L^4$
are, independently of one another, hydrogen, —T, —OH, —NR$_L^6$R$_L^7$, —CO—NH$_2$, a halogen radical, a branched or unbranched, optionally substituted $C_1$–$C_6$-alkyl, $C_2$–$C_6$-alkenyl, $C_2$–$C_6$-alkynyl, $C_3$–$C_7$-cycloalkyl, —CO—NH($C_1$–$C_6$-alkyl), —CO—N($C_1$–$C_6$-alkyl)$_2$ or $C_1$–$C_4$-alkoxy radical, an optionally substituted $C_1$–$C_2$-alkylene-T, $C_2$-alkenylene-T or $C_2$-alkynylene-T radical, an optionally substituted aryl or arylalkyl radical or, in each case independently of one another, two radicals $R_L^1$ and $R_L^2$ or $R_L^3$ and $R_L^4$ or, where appropriate, $R_L^1$ and $R_L^3$ together are an optionally substituted 3- to 7-membered saturated or unsaturated carbocyclic or heterocyclic system which may contain up to three different or identical heteroatoms O, N, S, $R_L^5$, $R_L^6$, $R_L^7$
    are, independently of one another, hydrogen, a branched or unbranched, optionally substituted $C_1$–$C_6$-alkyl, $C_3$–$C_7$-cycloalkyl, CO—O—$C_1$–$C_6$-alkyl, SO$_2$—$C_1$–$C_6$-alkyl or CO—$C_1$–$C_6$-alkyl radical or an optionally substituted CO—O-alkylene-aryl, SO$_2$-aryl, CO-aryl, SO$_2$-alkylene-aryl or CO-alkylene-aryl radical, G a structural element of the formula $I_G$

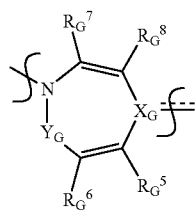

$I_G$ where
the structural element G can be incorporated in both orientations, and $X_G$ is nitrogen or $CR_G^1$ in the case where structural element G is connected to structural element L or B via $X_G$ by a single bond,
or
is carbon in the case where structural element G is connected to structural element L via $X_G$ by a double bond, $Y_G$ is CO, CS, C=$NR_G^2$ or $CR_G^3 R_G^4$,
where
$R_G^1$ is hydrogen, halogen, a hydroxyl group or a branched or unbranched, optionally substituted $C_1$–$C_6$-alkyl or $C_1$–$C_4$-alkoxy radical, $R_G^2$ is hydrogen, a hydroxyl group, a branched or unbranched, optionally substituted $C_1$–$C_6$-alkyl, $C_1$–$C_4$-alkoxy, $C_3$–$C_7$-cycloalkyl or —O—$C_3$–$C_7$-cycloalkyl radical or an optionally substituted aryl, —O-aryl, arylalkyl or —O-alkylene-aryl radical and $R_G^3$, $R_G^4$
    are, independently of one another, hydrogen or a branched or unbranched, optionally substituted $C_1$–$C_6$-alkyl, $C_2$–$C_6$-alkenyl, $C_2$–$C_6$-alkynyl or $C_1$–$C_4$-alkoxy radical or the two $R_G^3$ and $R_G^4$ radicals together are a cyclic acetal —O—CH$_2$—CH$_2$—O— or —O—CH$_2$—O— or the two $R_G^3$ and $R_G^4$ radicals together are an optionally substituted $C_3$–$C_7$-cycloalkyl radical, $R_G^5$, $R_G^6$, $R_G^7$, $R_G^8$
    are, independently of one another, hydrogen, an amino or hydroxyl group, an HN—CO—$R_G^9$ radical, a branched or unbranched, optionally substituted $C_1$–$C_6$-alkyl or $C_1$–$C_4$-alkoxy radical, an optionally substituted aryl or arylalkyl radical or, independently of one another, in each case two $R_G^5$ and $R_G^6$ or $R_G^7$ and $R_G^8$ radicals together are an optionally substituted, fused-on, unsaturated or aromatic 3- to 6-membered carbocyclic or heterocyclic system which may contain up to three different or identical heteroatoms O, N, S, and $R_G^9$ is a branched or unbranched, optionally substituted $C_1$–$C_6$-alkyl or $C_1$–$C_4$-alkoxy radical or an optionally substituted aryl, hetaryl, arylalkyl or hetarylalkyl radical, B a structural element containing at least one atom which, under physiological conditions, can as hydrogen acceptor form hydrogen bonds, where the distance between at least one hydrogen acceptor atom and the structural element G along the shortest possible route along the structural element framework is from 4 to 13 atomic bonds, and the physiologically tolerated salts, prodrugs and the enantiomerically pure or diastereomerically pure and tautomeric forms.

T in structural element L means a COOH group or a radical which can be hydrolyzed to COOH. A radical which can be hydrolyzed to COOH means a radical which is converted into a COOH group after hydrolysis.

An example which may be mentioned of a radical T which can be hydrolyzed to COOH is the group

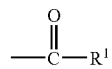

in which $R^1$ has the following meaning:
a) OM where M can be a metal cation such as an alkali metal cation such as lithium, sodium, potassium, the equivalent of an alkaline earth metal cation such as calcium, magnesium and barium or an environmentally compatible organic ammonium ion such as, for example, primary, secondary, tertiary or quaternary $C_1$–$C_4$-alkylammonium or ammonium ion, such as, for example, ONa, OK or OLi, b) a branched or unbranched, optionally halogen-substituted $C_1$–$C_8$-alkoxy radical such as, for example, methoxy, ethoxy, propoxy, 1-methylethoxy, butoxy, 1-methylpropoxy, 2-methylpropoxy, 1,1-dimethylethoxy, in particular methoxy, ethoxy, 1-methylethoxy, pentoxy, hexoxy, heptoxy, octoxy, difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy c) a branched or unbranched, optionally halogen-substituted $C_1$–$C_4$-alkylthio radical such as methylthio, ethylthio, propylthio, 1-methylethylthio, butylthio, 1-methylpropylthio, 2-methylpropylthio or 1,1-dimethylethylthio radical d) an optionally substituted —O-alkylene-aryl radical such as, for example, —O-benzyl e) $R^1$ also a radical —(O)$_m$—N($R^{18}$)($R^{19}$),
in which m is 0 or 1, and $R^{18}$ and $R^{19}$, which may be identical or different, have the following meaning:
hydrogen,
a branched or unbranched, optionally substituted $C_1$–$C_6$-alkyl radical such as, for example, methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl or the corresponding substituted radicals, preferably methyl, ethyl, propyl, butyl or i-butyl, $C_2$–$C_6$-alkenyl radical such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl or the corresponding substituted radicals, $C_2$–$C_6$-alkynyl radical such as, for example, ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl or 1-methyl-2-butynyl or the corresponding substituted radicals, $C_3$–$C_8$-cycloalkyl such as, for example, cyclopropyl, cyclobutyl, cyclopentyl, cyclohexyl and cycloheptyl, cyclooctyl or the corresponding substituted radicals, or a phenyl radical, optionally substituted one or more times, for example one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, such as, for example, 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl, 2,6-difluorophenyl, or $R^{18}$ and $R^{19}$ together form a $C_4$–$C_7$-alkylene chain which is closed to a ring, is optionally substituted, for example by $C_1$–$C_4$-alkyl, and may contain a heteroatom selected from the group of oxygen, sulfur or nitrogen, such as, for example, —(CH$_2$)$_4$—, —(CH$_2$)$_5$—, —(CH$_2$)$_6$—, —(CH$_2$)$_7$—, —(CH$_2$)$_2$—O—(CH$_2$)$_2$—, —CH$_2$—S—(CH$_2$)$_3$—, —(CH$_2$)$_2$—O—(CH$_2$)$_3$—, —NH—(CH$_2$)$_3$—, —CH$_2$—NH—(CH$_2$)$_2$—, —CH$_2$—CH=CH—CH$_2$—, —CH=CH—(CH$_2$)$_3$—, —CO—(CH$_2$)$_2$—CO— or —CO—(CH$_2$)$_3$—CO—.

Preferred T radicals are —COOH, —CO—O—$C_1$–$C_8$-alkyl or —CO—O-benzyl.

The radical —U— in the structural element L is a spacer selected from the group of —(X$_L$)$_a$—(CR$_L^1$R$_L^2$)$_b$—, —CR$_L^1$=CR$_L^2$—, ethynylene or =CR$_L^1$—. In the case of the =CR$_L^1$— radical, the structural element L is linked by a double bond to the structural element G.

X$_L$ is preferably the radical CR$_L^3$R$_L^4$, NR$_L^5$, oxygen or sulfur.

Preferred —U— radicals are the radicals =CR$_L^1$— or —(X$_L$)$_a$—(CR$_L^1$R$_L^2$)$_b$—, where X$_L$ is preferably CR$_L^3$R$_L^4$ (a=0 or 1) or oxygen (a=1).

Particularly preferred —U— radicals are the radicals —(X$_L$)$_a$—(CR$_L^1$R$_L^2$)$_b$—, where X$_L$ is preferably CR$_L^3$R$_L^4$ (a=1) or oxygen (a=1).

A halogen radical for R$_L^1$, R$_L^2$, R$_L^3$ or R$_L^4$ in structural element L means, for example, F, Cl, Br or I, preferably F.

A branched or unbranched $C_1$–$C_6$-alkyl radical for R$_L^1$, R$_L^2$, R$_L^3$ or R$_L^4$ in structural element L means, for example, methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, preferably branched or unbranched $C_1$–$C_4$-alkyl radicals such as, for example, methyl, ethyl, propyl, 1-methylethyl, butyl, 1-methylpropyl, 2-methylpropyl or 1,1-dimethylethyl, particularly preferably methyl.

A branched or unbranched $C_2$–$C_6$-alkenyl radical for R$_L^1$, R$_L^2$, R$_L^3$ or R$_L^4$ in structural element L means, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl.

A branched or unbranched $C_2$–$C_6$-alkynyl radical for R$_L^1$, R$_L^2$, R$_L^3$ or R$_L^4$ in structural element L means, for example, ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably ethynyl, 2-propynyl, 2-butynyl, 1-methyl-2-propynyl or 1-methyl-2-butynyl.

A branched or unbranched $C_3$–$C_7$-cycloalkyl radical for $R_L^1$, $R_L^2$, $R_L^3$ or $R_L^4$ in structural element L means, for example, cyclopropyl, cyclobutyl, cyclopentyl, cyclohexyl or cycloheptyl.

A branched or unbranched $C_1$–$C_4$-alkoxy radical for $R_L^1$, $R_L^2$, $R_L^3$ or $R_L^4$ in structural element L means, for example, methoxy, ethoxy, propoxy, 1-methylethoxy, butoxy, 1-methylpropoxy, 2-methylpropoxy or 1,1-dimethylethoxy.

The radicals —CO—NH($C_1$–$C_6$-alkyl) and —CO—N($C_1$–$C_6$-alkyl)$_2$ are respectively secondary and tertiary amides and are composed of the amide linkage and the appropriate $C_1$–$C_6$-alkyl radicals as described above for $R_L^1$, $R_L^2$, $R_L^3$ or $R_L^4$.

The $R_L^1$, $R_L^2$, $R_L^3$ or $R_L^4$ radicals may further be a radical $C_1$–$C_2$-alkylene-T such as, for example, methylene-T or ethylene-T, $C_2$-alkenylene-T such as, for example, ethenylene-T or $C_2$-alkynylene-T such as, for example, ethynylene-T, an aryl radical such as, for example, phenyl, 1-naphthyl or 2-naphthyl or an arylalkyl radical such as, for example, benzyl or phenethyl it being possible for the radicals to be substituted where appropriate.

It is also possible for, in each case independently of one another, two radicals $R_L^1$ and $R_L^2$ or $R_L^3$ and $R_L^4$ or, where appropriate, $R_L^1$ and $R_L^3$ together to be an optionally substituted 3- to 7-membered saturated or unsaturated carbocyclic or heterocyclic system which may contain up to three different or identical heteroatoms O, N, S.

All radicals for $R_L^1$, $R_L^2$, $R_L^3$ or $R_L^4$ may optionally be substituted. Unless the substituents are specified, independently of one another up to 5 substituents are suitable for the radicals $R_L^1$, $R_L^2$, $R_L^3$ or $R_L^4$ and all other substituted radicals in the description hereinafter, for example selected from the following group:

—$NO_2$, —$NH_2$, —OH, —CN, —COOH, —O—$CH_2$—COOH, halogen, a branched or unbranched, optionally substituted $C_1$–$C_4$-alkyl such as, for example, methyl, $CF_3$, $C_2F_5$ or $CH_2F$, —CO—O—$C_1$–$C_4$-alkyl, $C_3$–$C_6$-cycloalkyl, $C_1$–$C_4$-alkoxy, $C_1$–$C_4$-alkylthio, —NH—CO—O—$C_1$–$C_4$-alkyl, —O—$CH_2$—COO—$C_1$–$C_4$-alkyl, —NH—CO—$C_1$–$C_4$-alkyl, —CO—NH—$C_1$–$C_4$-alkyl, —NH—$SO_2$—$C_1$–$C_4$-alkyl, —$SO_2$—NH—$C_1$–$C_4$-alkyl, —N($C_1$–$C_4$-alkyl)$_2$, —NH—$C_1$–$C_4$-alkyl or —$SO_2$—$C_1$–$C_4$-alkyl radical, such as, for example, —$SO_2$—$CF_3$, an optionally substituted —NH—CO-aryl, —CO—NH-aryl, —NH—CO—O-aryl, —NH—CO—O-alkylene-aryl, —NH—$SO_2$-aryl, —$SO_2$—NH-aryl, —CO—NH-benzyl, —NH—$SO_2$-benzyl or —$SO_2$—NH-benzyl radical, an optionally substituted —$SO_2$—$NR^2R^3$ or —CO—$NR^2R^3$ radical, where the radicals $R^2$ and $R^3$ may, independently of one another, have the meaning of $R_L^5$ hereinafter, or the two radicals $R^2$ and $R^3$ together are a 3- to 6-membered, optionally substituted, saturated, unsaturated or aromatic heterocyclic system which, in addition to the ring nitrogen, may contain up to three other different or identical heteroatoms O, N, S, and optionally two radicals substituting this heterocyclic system together are a fused-on or saturated, unsaturated or aromatic carbocyclic or heterocyclic system which may contain up to three different or identical heteroatoms O, N, S, and the ring can optionally be substituted or another, optionally substituted ring can be fused onto this ring.

Unless specified, two substituents on all terminally bonded, substituted hetaryl radicals in the description may form a fused-on, 5- to 7-membered, unsaturated or aromatic carbocyclic system.

Preferred $R_L^1$, $R_L^2$, $R_L^3$ or $R_L^4$ radicals are, independently of one another, hydrogen, halogen, a branched or unbranched, optionally substituted $C_1$–$C_4$-alkyl, $C_1$–$C_4$-alkoxy or $C_3$–$C_7$-cycloalkyl radical or the —$NR_L^6R_L^7$ radical.

Particularly preferred $R_L^1$, $R_L^2$, $R_L^3$ or $R_L^4$ radicals are, independently of one another, hydrogen, fluorine or a branched or unbranched, optionally substituted $C_1$–$C_4$-alkyl radical, preferably methyl.

The $R_L^5$, $R_L^6$, $R_L^7$ radicals in the structural element L are, independently of one another, hydrogen, a branched or unbranched, optionally substituted $C_1$–$C_6$-alkyl radical, for example as described above for $R_L^1$, $C_3$–$C_7$-cycloalkyl radical, for example as described above for $R_L^1$, CO—O—$C_1$–$C_6$-alkyl, $SO_2$—$C_1$–$C_6$-alkyl or CO—$C_1$–$C_6$-alkyl radical which is composed of the group CO—O, $SO_2$ or CO and, for example, of the $C_1$–$C_6$-alkyl radicals described above for $R_L^1$, or an optionally substituted CO—O—alkylene-aryl, $SO_2$-aryl, $SO_2$-alkylene-aryl or CO-alkylene-aryl radical which is composed of the group CO—O, $SO_2$, or CO and, for example, of the aryl or arylalkyl radicals described above for $R_L^1$.

Preferred $R_L^6$ radicals in the structural element L are hydrogen, a branched or unbranched, optionally substituted $C_1$–$C_4$-alkyl, CO—O—$C_1$–$C_4$-alkyl, CO—$C_1$–$C_4$-alkyl or $SO_2$—$C_1$–$C_4$-alkyl radical or an optionally substituted CO—O-benzyl, $SO_2$-aryl, $SO_2$-alkylene-aryl or CO-aryl radical.

Preferred $R_L^7$ radicals in the structural element L are hydrogen or a branched or unbranched, optionally substituted $C_1$–$C_4$-alkyl radical.

Preferred structural elements L are composed of the preferred radicals of the structural element.

Particularly preferred structural elements L are composed of the particularly preferred radicals of the structural element.

G is a structural element of the formula $I_G$

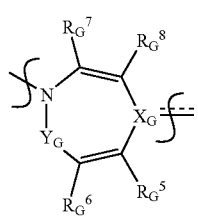

$I_G$ it being possible for the structural element G to be incorporated in both orientations. The case where $X_G$ is connected by a double bond to the next structural element applies only for the orientation in which the structural element G is connected via $X_G$ by a double bond to structural element L.

In the case of a single bond, the structural element G can be incorporated in both orientations.

In the case where structural element G is connected to structural element L or B via $X_G$ by a single bond, $X_G$ is nitrogen or $CR_G^1$.

In the case where structural element G is connected to structural element L via $X_G$ by a double bond, $X_G$ is carbon.

$Y_G$ in structural element G is CO, CS, $C=NR_G^2$ or $CR_G^3R_G^4$, preferably CO, $C=NR_G^2$ or $CR_G^3R_G^4$.

$R_G^1$ in structural element G is hydrogen, halogen such as, for example, Cl, F, Br or I, a hydroxyl group or a branched or unbranched, optionally substituted $C_1-C_6$-alkyl, preferably $C_1-C_4$-alkyl or $C_1-C_4$-alkoxy radical, for example as described above in each case for $R_L^1$.

Particularly preferred $R_G^1$ radicals are hydrogen, methoxy or ethoxy.

$R_G^2$ in structural element G is hydrogen, a hydroxyl group, a branched or unbranched, optionally substituted $C_1-C_6$-alkyl, $C_1-C_4$-alkoxy or $C_3-C_7$-cycloalkyl radical, for example as described above in each case for $R_L^1$, an optionally substituted $-O-C_3-C_7$-cycloalkyl radical which is composed of an ether group and, for example, of the $C_3-C_7$-cycloalkyl radical described above for $R_L^1$, an optionally substituted aryl or arylalkyl radical, for example as described above in each case for $R_L^1$, or an optionally substituted —O-aryl or —O-alkylene-aryl radical which is composed of a —O— group and, for example, of the aryl or arylalkyl radicals described above for $R_L^1$.

Branched or unbranched, optionally substituted $C_1-C_6$-alkyl, $C_2-C_6$-alkenyl, $C_2-C_6$-alkynyl or $C_1-C_4$-alkoxy radicals for $R_G^3$ or $R_G^4$ in structural element G mean, independently of one another, for example the corresponding radicals described above in each case for $R_L^1$.

It is also possible for the two radicals $R_G^3$ and $R_G^4$ together to form a cyclic acetal such as, for example, $-O-CH_2-CH_2-O-$ or $-O-CH_2-O-$.

A further possibility is for the two radicals $R_G^3$ and $R_G^4$ together to form an optionally substituted $C_3-C_7$-cycloalkyl radical.

Preferred $R_G^3$ or $R_G^4$ radicals are, independently of one another, hydrogen, $C_1-C_4$-alkyl or $C_1-C_4$-alkoxy.

Branched or unbranched, optionally substituted $C_1-C_6$-alkyl or $C_1-C_4$-alkoxy radicals and optionally substituted aryl or arylalkyl radicals for $R_G^5$ $R_G^6$, $R_G^7$ or $R_G^8$ in structural element G mean, independently of one another, for example the corresponding radicals described above in each case for $R_L^1$.

It is also possible for in each case two radicals $R_G^5$ and $R^{G6}$ or $R_G^7$ and $R_G^8$ independently of one another together to form an optionally substituted, fused-on, unsaturated or aromatic 3- to 6-membered carbocyclic or heterocyclic system which may contain up to three different or identical heteroatoms O, N, S.

Preferred $R_G^5$, $R_G^6$, $R_G^7$ or $R_G^8$ radicals are, independently of one another, hydrogen or optionally substituted aryl radicals, preferably phenyl or arylalkyl radicals, preferably benzyl, and in each case two radicals $R_G^5$ and $R_G^6$ or $R_G^7$ and $R_G^8$ together are an optionally substituted, fused-on, unsaturated or aromatic 3- to 6-membered carbocyclic or heterocyclic system which may contain up to three different or identical heteroatoms O, N, S.

With particularly preferred radicals for $R_G^5$, $R_G^6$, $R_G^7$ or $R_G^8$, independently of one another in each case two radicals $R_G^5$ and $R_G^6$ or $R_G^7$ and $R_G^8$ together form an optionally substituted, fused-on, unsaturated or aromatic 3- to 6-membered carbocyclic or heterocyclic system selected from one of the following doubly linked structural formulae:

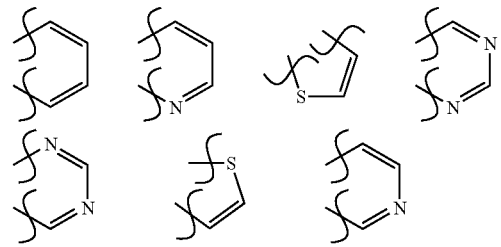

A branched or unbranched, optionally substituted $C_1-C_6$-alkyl or $C_1-C_4$-alkoxy radical and an optionally substituted aryl or arylalkyl radical for $R_G^9$ mean, for example, the corresponding radicals described above for $R_L^1$.

A hetaryl radical for $R_G^9$ means, for example, radicals such as 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl.

Substituted hetaryl radicals for $R_G^9$ mean, as described above generally for terminal, substituted hetaryl radicals, also fused-on derivatives of the abovementioned hetaryl radicals, such as, for example, indazole, indole, benzothiophene, benzofuran, indoline, benzimidazole, benzothiazole, benzoxazole, quinoline or isoquinoline radicals.

A hetarylalkyl radical for $R_G^9$ means radicals composed, for example, of the $C_1-C_6$-alkyl radicals described above and of the hetaryl radicals described above, such as, preferably, the radicals $-CH_2$-2-pyridyl, $-CH_2$-3-pyridyl, $-CH_2$-4-pyridyl, $-CH_2$-2-thienyl, $-CH_2$-3-thienyl, $-CH_2$-2-thiazolyl, $-CH_2$-4-thiazolyl, $CH_2$-5-thiazolyl, $-CH_2-CH_2$-2-pyridyl, $-CH_2-CH_2$-3-pyridyl, $-CH_2-CH_2$-4-pyridyl, $-CH_2-CH_2$-2-thienyl, $-CH_2-CH_2$-3-thienyl, $-CH_2-CH_2$-2-thiazolyl, $-CH_2-CH_2$-4-thiazolyl or $-CH_2-CH_2$-5-thiazolyl.

Preferred structural elements G are composed of the preferred radicals of the structural element.

Particularly preferred structural elements G are composed of the particularly preferred radicals of the structural element.

Structural element B means a structural element containing at least one atom which, under physiological conditions, can as hydrogen acceptor form hydrogen bonds, where the distance between at least one hydrogen acceptor atom and the structural element G along the shortest possible route along the structural element framework is from 4 to 13 atomic bonds. The design of the structural framework of the structural element B can be varied widely.

Examples of suitable atoms which, under physiological conditions, can as hydrogen acceptors form hydrogen bonds are atoms with Lewis base properties such as, for example, the heteroatoms nitrogen, oxygen or sulfur.

Physiological conditions mean a pH prevailing at the site in an organism where the ligands interact with the receptors. In the present case, the physiological conditions have a pH of, for example, 5 to 9.

In a preferred embodiment, the structural element B is a structural element of the formula $I_B$ $$A{-}E{-} \qquad I_B$$

where A and E have the following meanings:

a structural element selected from the group:

- a 5- to 7-membered monocyclic saturated, unsaturated or aromatic ring having 0 to 4 heteroatoms selected from the group of O, N or S, it being possible, in each case independently of one another, for the ring nitrogen which is present where appropriate or all carbons to be substituted, with the proviso that at least one heteroatom selected from the group of O, N or S is present in the structural element A, or

- a 9- to 14-membered polycyclic saturated, unsaturated or aromatic system having up to 6 heteroatoms selected from the group of N, O or S, it being possible, in each case independently of one another, for the ring nitrogen which is present where appropriate or all carbons to be substituted, with the proviso that at least one heteroatom selected from the group of O, N or S is present in the structural element A, or

- a radical

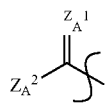

where $Z_A^1$ is oxygen, sulfur or optionally substituted nitrogen and $Z_A^2$ is optionally substituted nitrogen, oxygen or sulfur, and E a spacer structural element which connects structural element A to structural element G covalently, where the number of atomic bonds along the shortest possible route along the structural element framework E is from 4 to 12.

In a particularly preferred embodiment, the structural element A is a structural element selected from the group of structural elements of the formulae $I_A^1$ to $I_A^{18}$,

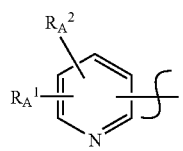  $I_A^1$

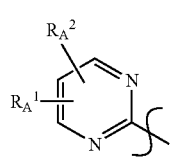  $I_A^2$

-continued

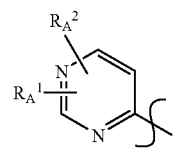  $I_A^3$

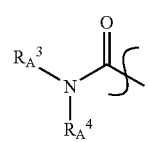  $I_A^4$

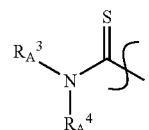  $I_A^5$

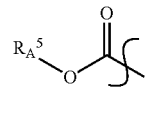  $I_A^6$

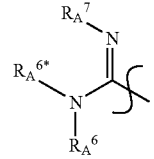  $I_A^7$

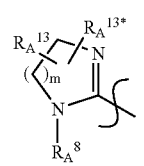  $I_A^8$

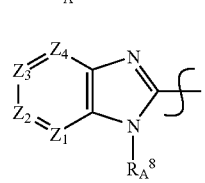  $I_A^9$

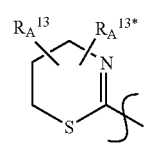  $I_A^{10}$

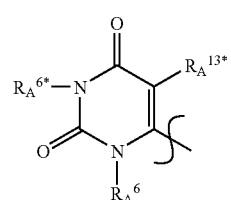  $I_A^{11}$

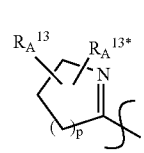  $I_A^{12}$

-continued

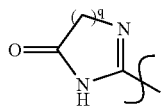
$I_A{}^{13}$

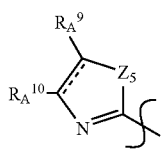
$I_A{}^{14}$

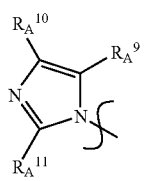
$I_A{}^{15}$

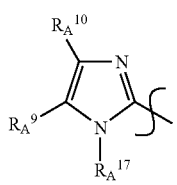
$I_A{}^{16}$

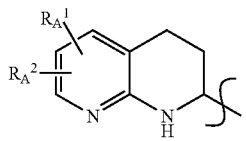
$I_A{}^{17}$

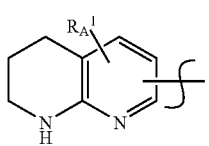
$I_A{}^{18}$ where m, p, q are, independently of one another, 1, 2 or 3, $R_A{}^1$, $R_A{}^2$ are, independently of one another, hydrogen, CN, halogen, a branched or unbranched, optionally substituted $C_1$–$C_6$-alkyl or CO—$C_1$–$C_6$-alkyl radical or an optionally substituted aryl, arylalkyl, hetaryl, hetarylalkyl or $C_3$–$C_7$-cycloalkyl radical or a radical CO—O—$R_A{}^{14}$, O—$R_A{}^{14}$, S—$R_A{}^{14}$, $NR_A{}^{15}R_A{}^{16}$, CO—$NR^{415}R_A{}^{16}$ or $SO_2NR_A{}^{15}R_A{}^{16}$ or the two $R_A{}^1$ and $R_A{}^2$ radicals together are a fused-on, optionally substituted 5- or 6-membered, unsaturated or aromatic carbocyclic or heterocyclic system which may contain up to three heteroatoms selected from the group of O, N or S, $R_A{}^{13}$, $R_A{}^{13}*$ are, independently of one another, hydrogen, CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A{}^{14}$, O—$R_A{}^{14}$, S—$R_A{}^{14}$, $NR^{415}R_A{}^{16}$ or CO—$NR_A{}^{15}R_A{}^{16}$ radical, where $R_A{}^{14}$ is hydrogen, a branched or unbranched, optionally substituted $C_1$–$C_6$-alkyl, alkylene-$C_1$–$C_4$-alkoxy, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_A{}^{15}$, $R_A{}^{16}$, are, independently of one another, hydrogen, a branched or unbranched, optionally substituted $C_1$–$C_6$-alkyl, CO—$C_1$–$C_6$-alkyl, $SO_2$—$C_1$–$C_6$-alkyl, COO—$C_1$–$C_6$-alkyl, arylalkyl, COO-alkylene-aryl, $SO_2$-alkylene-aryl or hetarylalkyl radical or an optionally substituted $C_3$–$C_7$-cycloalkyl, aryl, CO-aryl, $SO_2$-aryl, hetaryl or CO-hetaryl radical, $R_A{}^3$, $R_A{}^4$ are, independently of one another, hydrogen, —$(CH_2)_n$—$(X_A)_j$—$R_A{}^{12}$, or the two radicals together are a 3 to 8-membered, saturated, unsaturated or aromatic N heterocyclic system which may additionally contain two other identical or different heteroatoms O, N or S, it being possible for the ring optionally to be substituted or for another, optionally substituted, saturated, unsaturated or aromatic ring to be fused onto this ring, where n can be 0, 1, 2 or 3, j can be 0 or 1, $X_A$ can be —$SO_2$—, —S—, —O—, —CO—, —O—CO—, —CO—O—, —CO—N($R_A{}^{12}$)—, —N($R_A{}^{12}$)—CO—, —N($R_A{}^{12}$)—$SO_2$— or —$SO_2$—N($R_A{}^{12}$)- and $R_A{}^{12}$ can be hydrogen, a branched or unbranched, optionally substituted $C_1$–$C_6$-alkyl, $C_1$–$C_4$-alkoxy, —O-alkylene-aryl or —O-aryl radical, an amino radical with primary or, where appropriate, secondary or tertiary substitution, an optionally $C_1$–$C_4$-alkyl- or aryl-substituted $C_2$–$C_6$-alkynyl or $C_2$–$C_6$-alkenyl radical or a 3- to 6-membered, saturated or unsaturated heterocyclic system which is substituted by up to three identical or different radicals and which may contain up to three different or identical heteroatoms O, N, S, $C_3$–$C_7$-cycloalkyl, aryl or hetaryl radical, it being possible for two radicals together to be a fused-on, saturated, unsaturated or aromatic carbocyclic or heterocyclic system which may contain up to three different or identical heteroatoms O, N, S, and the ring may optionally be substituted, or another, optionally substituted, saturated, unsaturated or aromatic ring may be fused onto this ring, $R_A{}^5$ is a branched or unbranched, optionally substituted $C_1$–$C_6$-alkyl, arylalkyl, $C_3$–$C_7$-cycloalkyl or $C_1$–$C_6$-alkyl-$C_3$–$C_7$-cycloalkyl radical or an optionally substituted aryl radical, $R_A{}^6$, $R_A{}^6*$ are hydrogen, a branched or unbranched, optionally substituted $C_1$–$C_4$-alkyl, —CO—O—$C_1$–$C_4$-alkyl, arylalkyl, —CO—O-alkylene-aryl, —CO—O-allyl, —CO—$C_1$–$C_4$-alkyl, —CO-alkylene-aryl, $C_3$–$C_7$-cycloalkyl or —CO-allyl radical or the two radicals $R_A{}^6$ and $R_A{}^6*$ in the structural element $I_A{}^7$ together are an optionally substituted, saturated, unsaturated or aromatic heterocyclic system which may, in addition to the ring nitrogen, contain up to two further different or identical heteroatoms O, N, S, $R_A^7$ is hydrogen, —OH, —CN, —CONH$_2$, a branched or unbranched, optionally substituted $C_1$–$C_4$-alkyl, $C_1$–$C_4$-alkoxy, $C_3$–$C_7$-cycloalkyl or —O—CO—$C_1$–$C_4$-alkyl radical, or an optionally substituted arylalkyl, —O-alkylene-aryl, —O—CO-aryl, —O—CO-alkylene-aryl or —O—CO-allyl radical, or the two radicals $R_A^6$ and $R_A^7$ together are an optionally substituted, unsaturated or aromatic heterocyclic system which may, in addition to the ring nitrogen, contain up to two further different or identical heteroatoms O, N, S, $R_A^8$ is hydrogen, a branched or unbranched, optionally substituted $C_1$–$C_4$-alkyl, CO—$C_1$–$C_4$-alkyl, SO$_2$—$C_1$–$C_4$-alkyl or CO—O—$C_1$–$C_4$-alkyl radical or an optionally substituted aryl, CO-aryl, SO$_2$-aryl, CO—O-aryl, CO-alkylene-aryl, SO$_2$-alkylene-aryl, CO—O-alkylene-aryl or alkylene-aryl radical, $R_A^9$, $R_A^{10}$
are, independently of one another, hydrogen, —CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, NR$^{A15}R_A^{16}$ or CO—NR$_A^{15}R_A^{16}$ radical, or the two $R_A^9$ and $R_A^{10}$ radicals in the structural element $I_A^{14}$ together are a 5- to 7-membered saturated, unsaturated or aromatic carbocyclic or heterocyclic system which may contain up to three different or identical heteroatoms O, N, S and is optionally substituted by up to three identical or different radicals, $R_A^{11}$ is hydrogen, —CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, NR$_A^{15}R_A^{16}$ or CO-NR$_A^{15}R_A^{16}$ radical, $R_A^{17}$ in the structural element $I_A^{16}$ the two radicals $R_A^9$ and $R_A^{17}$ together are a 5- to 7-membered saturated, unsaturated or aromatic heterocyclic system which may, in addition to the ring nitrogen, contain up to three different or identical heteroatoms O, N, S, and is optionally substituted by up to three identical or different radicals, $Z^1$, $Z^2$, $Z^3$, $Z^4$
are, independently of one another, nitrogen, C—H, C-halogen or a branched or unbranched, optionally substituted C—$C_1$–$C_4$-alkyl or C—$C_1$–$C_4$-alkoxy radical, $Z^5$ is NR$_A^8$, oxygen or sulfur.

Halogen for $R_A^1$ or $R_A^2$ in the structural elements $I_A^1$, $I_A^2$, $I_A^3$ or $I_A^{17}$ means, independently of one another, fluorine, chlorine, bromine or iodine.

A branched or unbranched, optionally substituted $C_1$–$C_6$-alkyl radical for $R_A^1$ or $R_A^2$ means, independently of one another, for example the corresponding radicals described above for $R_L^1$, preferably methyl or trifluoromethyl.

The branched or unbranched, optionally substituted CO—$C_1$–$C_6$-alkyl radical for $R_A^1$ or $R_A^2$ in the structural elements $I_A^1$, $I_A^2$, $I_A^3$ or $I_A^{17}$ is composed, for example, of the group CO and the branched or unbranched, optionally substituted $C_1$–$C_6$-alkyl radicals described above for $R_A^1$ or $R_A^2$.

Optionally substituted aryl, arylalkyl or $C_3$–$C_7$-cycloalkyl radicals for $R_A^1$ or $R_A^2$ mean, independently of one another, for example the corresponding radicals described above for $R_L^1$.

Optionally substituted hetaryl or alkylhetaryl radicals for $R_A^1$ or $R_A^2$ in the structural elements $I_A^1$, $I_A^2$, $I_A^3$ or $I_A^{17}$ mean, independently of one another, for example the corresponding radicals described above for $R_G^9$.

The optionally substituted radicals CO—O—$R_A^{14}$, O—$R_A^{14}$, S—$R_A^{14}$, NR$^{15}R_A^{16}$, CO—NR$_A^{15}R_A^{16}$ or SO$_2$NR$_A^{15}R_A^{16}$ for $R_A^1$ or $R_A^2$ are composed, for example, of the groups CO—O, O, S, N, CO—N or SO$_2$—N and the radicals $R_A^{14}$, $R_A^{15}$ and $R_A^{16}$ which are described in detail below.

It is also possible for the two radicals $R_A^1$ and $R_A^2$ together to form a fused-on, optionally substituted, 5- or 6-membered, unsaturated or aromatic carbocyclic or heterocyclic system which may contain up to three heteroatoms selected from the group of O, N, or S.

$R_A^{13}$ and $R_A^{13*}$ are, independently of one another, hydrogen, CN, halogen such as, for example, fluorine, chlorine, bromine or iodine, a branched or unbranched, optionally substituted $C_1$–$C_6$-alkyl radical as described above, for example, for $R_A^1$ or $R_A^2$, preferably methyl or trifluoromethyl or an optionally substituted aryl, arylalkyl, hetaryl or $C_3$–$C_7$-cycloalkyl radical or a CO—O—$R_A^{14}$, O—$R_A^{14}$, S—$R_A^{14}$, NR$_A^{15}R_A^{16}$ or CO—NR$_A^{15}R_A^{16}$ radical as described in each case above for $R_A^1$ or $R_A^2$.

A branched or unbranched, optionally substituted $C_1$–$C_6$-alkyl, $C_3$–$C_7$-cycloalkyl, $C_2$–$C_6$-alkenyl or $C_2$–$C_6$-alkynyl radical for $R_A^{14}$ in structural element A means, for example, the corresponding radicals described above for $R_L^1$.

A branched or unbranched, optionally substituted alkylene-cycloalkyl radical or alkylene-$C_1$–$C_4$-alkoxy radical for $R_A^{14}$ in structural element A means, for example, radicals which are composed of the branched or unbranched, optionally substituted $C_1$–$C_6$-alkyl radicals described above for $R^{L1}$ and of the optionally substituted $C_3$–$C_7$-cycloalkyl radicals or $C_1$–$C_4$-alkoxy radicals.

Optionally substituted aryl, arylalkyl, hetaryl or alkylhetaryl radicals for $R_A^{14}$ in structural element A mean, for example, the corresponding radicals described above for $R_A^1$ or $R_A^2$.

A branched or unbranched, optionally substituted $C_1$–$C_6$-alkyl or arylalkyl radical or an optionally substituted $C_3$–$C_7$-cycloalkyl, aryl, hetaryl or hetarylalkyl radical for $R_A^{15}$ or $R^{A16}$ means, independently of one another, for example the corresponding radicals described above for $R_A^{14}$.

The branched or unbranched, optionally substituted CO—$C_1$–$C_6$-alkyl, SO$_2$—$C_1$–$C_6$-alkyl, COO —$C_1$–$C_6$-alkyl, COO-alkylene-aryl or SO$_2$-alkylene-aryl radicals or the optionally substituted CO-aryl, SO$_2$-aryl or CO-hetaryl radicals for $R_A^{15}$ or $R_A^{16}$ are composed, for example, of the corresponding groups —CO—, —SO$_2$—, —COO— and the corresponding branched or unbranched, optionally substituted $C_1$–$C_6$-alkyl or arylalkyl radicals described above or the corresponding optionally substituted aryl or hetaryl radicals.

A —(CH$_2$)$_n$—(X$_A$)$_j$—$R_A^{12}$ radical for $R_A^3$ or $R_A^4$ means, independently of one another, a radical composed of the corresponding radicals —(CH$_2$)$_n$—, (X$_A$)$_i$ and $R_A^{12}$. In these cases, n can be 0, 1, 2 or 3 and j can be 0 or 1.

$X_A$ is a doubly linked radical selected from the group of —SO$_2$—, —S—, —O—, —CO—, —O—CO—, —CO—O—, —CO—N(R$_A^{12}$)—, —N(R$_A^{12}$)—CO—, —N(R$_A^{12}$)—SO$_2$— and —SO$_2$—N(R$_A^{12}$)—.

$R_A^{12}$ is hydrogen, a branched or unbranched, optionally substituted $C_1$–$C_6$-alkyl or $C_1$–$C_4$-alkoxy as described above for $R_L^1$, an optionally substituted —O-alkylene-aryl or —O-aryl radical, where the arylalkyl and aryl radicals have, for example, the meaning described above for $R_L^1$ and may optionally be substituted, an amino radical with primary or, where appropriate, secondary or tertiary substitution, such as, for example, —NH$_2$, —NH($C_1$–$C_6$-alkyl) or —N($C_1$–$C_6$-alkyl)$_2$ or, in the case of a terminal, singly bonded radical $R_A^{12}$, also for example the corresponding cyclic amines such as, for example, N-pyrrolidinyl, N-piperidinyl, N-hexahydroazepinyl, N-morpholinyl or N-piperazinyl, and in the case where heterocycles carry free amine protons, such as, for example, N-piperazinyl, the free amine protons can be replaced by conventional amine protective groups such as, for example, methyl, benzyl, boc (tert-butoxycarbonyl), z (benzyloxycarbonyl), tosyl, —SO$_2$—$C_1$–$C_4$-alkyl, —SO$_2$-phenyl or —SO$_2$-benzyl, an optionally $C_1$–$C_4$-alkyl- or aryl-substituted $C_2$–$C_6$-alkynyl or $C_2$–$C_6$-alkenyl radical as described above, for example, for $R_L^1$, or a 3- to 6-membered, saturated or unsaturated heterocyclic system which is substituted by up to three identical or different radicals and which may contain up to three different or identical heteroatoms O, N, S, such as, for example, 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 1,3,4-thiadiazol-2-yl, 1,3,4-oxadiazol-2-yl, 3-isoxazolyl, 4-isoxazolyl, 5-isoxazolyl, triazinyl.

The various radicals may form a fused-on system as generally described above.

$C_3$–$C_7$-cycloalkyl, aryl or hetaryl radical as described above, for example, for $R_A^{13}$, it being possible for two radicals together to be a fused-on, saturated, unsaturated or aromatic carbocyclic or heterocyclic system which may contain up to three different or identical heteroatoms O, N, S, and the ring may optionally be substituted, or another, optionally substituted, saturated, unsaturated or aromatic ring may be fused onto this ring.

$R_A^3$ and $R_A^4$ may also together form a 3- to 8-membered, saturated, unsaturated or aromatic N heterocyclic system which may additionally contain two other, identical or different heteroatoms O, N or S, it being possible for the ring optionally to be substituted or for another, optionally substituted, saturated, unsaturated or aromatic ring to be fused onto this ring.

$R_A^5$ is a branched or unbranched, optionally substituted $C_1$–$C_6$-alkyl, arylalkyl or $C_3$–$C_7$-cycloalkyl radical as described above, for example, for $R_L^1$, or a $C_1$–$C_6$-alkyl-$C_3$–$C_7$-cycloalkyl radical which is composed, for example, of the corresponding radicals described above.

$R_A^6$ and $R_A^{6*}$ are, independently of one another, hydrogen, a branched or unbranched, optionally substituted $C_1$–$C_4$-alkylradical such as, for example, optionally substituted methyl, ethyl, propyl, 1-methylethyl, butyl, 1-methylpropyl, 2-methylpropyl or 1,1-dimethylethyl, —CO—O—$C_1$–$C_4$-alkyl or —CO—$C_1$–$C_4$-alkyl radical such as, for example, composed of the group —CO—O— or —CO— and the $C_1$–$C_4$-alkyl radicals described above, arylalkyl radical as described above for $R_L^1$, —CO—O-alkylene-aryl or —CO-alkylene-aryl radical such as, for example, composed of the group —CO—O— or —CO— and the arylalkyl radicals described above, —CO—O-allyl or —CO-allyl radical, or $C_3$–$C_7$-cycloalkyl radical as described above, for example, for $R_L^1$.

It is also possible for the two radicals $R_A^6$ and $R_A^{6*}$ in structural element $I_A^7$ together to form an optionally substituted, saturated, unsaturated or aromatic heterocyclic system which, in addition to the ring nitrogen, may contain up to two other different or identical heteroatoms O, N, S.

$R_A^7$ is hydrogen, —OH, —CN, —CONH$_2$, a branched or unbranched, optionally substituted $C_1$–$C_4$-alkyl radical, for example as described above for $R_A^6$, $C_1$–$C_4$-alkoxy, arylalkyl or $C_3$–$C_7$-cycloalkyl radical, for example as described above for $R_L^1$, a branched or unbranched, optionally substituted —O—CO—$C_1$–$C_4$-alkyl radical which is composed of the group —O—CO— and, for example, of the above-mentioned $C_1$–$C_4$-alkyl radicals, or an optionally substituted —O-alkylene-aryl, —O—CO-aryl, —O—CO-alkylene-aryl or —O—CO-allyl radical which is composed of the groups —O— or —O—CO—and, for example, of the corresponding radicals described above for $R_L^1$.

It is also possible for the two radicals $R_A^6$ and $R_A^7$ together to form an optionally substituted, unsaturated or aromatic heterocyclic system which, in addition to the ring nitrogen, may contain up to two other different or identical heteroatoms O, N, S.

A branched or unbranched, optionally substituted $C_1$–$C_4$-alkyl radical or an optionally substituted aryl or arylalkyl radical for $R_A^8$ in structural element A means, for example, the corresponding radicals described above for $R_A^{15}$, where the CO—$C_1$–$C_4$-alkyl, SO$_2$—$C_1$–$C_4$-alkyl, CO—O—$C_1$–$C_4$-alkyl, CO-aryl, SO$_2$-aryl, CO—O—aryl, CO-alkylene-aryl, SO$_2$-alkylene-aryl or CO—O-alkylene-aryl radicals are composed, in analogy to the other composed radicals, of the group CO, SO$_2$ or COO and, for example, of the corresponding $C_1$–$C_4$-alkyl, aryl or arylalkyl radicals described above for $R_A^{15}$, and these radicals may optionally be substituted.

Halogen for $R_A^9$ or $R_A^{10}$ means, independently of one another, fluorine, chlorine, bromine or iodine.

A branched or unbranched, optionally substituted $C_1$–$C_6$-alkyl radical or an optionally substituted aryl, arylalkyl, hetaryl or $C_3$–$C_7$-cycloalkyl radical in each case for $R_A^9$ or $R_A^{10}$ mean, independently of one another, for example the corresponding radicals described above for $R_A^{14}$, preferably methyl or trifluoromethyl.

A CO—O—$R_A^{14}$, O—$R_A^{14}$, S—$R_A^{14}$, NR$_A^{15}$R$_A^{16}$ or CO—NR$_A^{15}$R$_A^{16}$ radical in each case for $R_A^9$ or $R_A^{10}$ means, independently of one another, for example the corresponding radicals described above for $R_A^{13}$.

It is also possible for the two radicals $R_A^9$ and $R_A^{10}$ together in the structural element $I_A^{14}$ to form a 5- to 7-membered saturated, unsaturated or aromatic carbocyclic or heterocyclic system which may contain up to three different or identical heteroatoms O, N, S and is optionally substituted by up to three identical or different radicals.

Substituents mean in this case in particular halogen, CN, a branched or unbranched, optionally substituted $C_1$–$C_4$-alkyl radical such as, for example, methyl or trifluoromethyl or the radicals O—$R_A^{14}$, S—$R_A^{14}$, $NR_A^{15}R_A^{16}$, CO—$NR^{A15}R_A^{16}$ or —$((R_A^8)HN)C=N-R_A^7$.

Halogen for $R_A^{11}$ means, for example, fluorine, chlorine, bromine or iodine.

A branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, $NR_A^{15}R_A^{16}$ or CO—$NR_A^{15}R_A^{16}$ radical for $R_A^{11}$ means, for example, the corresponding radicals described above for $R_A^9$.

It is also possible for the two radicals $R_A^9$ and $R_A^{17}$ in the structural element $I_A^{16}$ together to form a 5- to 7-membered saturated, unsaturated or aromatic heterocyclic system which may, in addition to the ring nitrogen, contain up to three different or identical heteroatoms O, N, S and is optionally substituted by up to three identical or different radicals.

$Z^1, Z^2, Z^3, Z^4$ are, independently of one another, nitrogen, C—H, C-halogen such as, for example, C—F, C—Cl, C—Br or C—I or a branched or unbranched, optionally substituted C—$C_1$–$C_4$-alkyl radical which is composed of a carbon radical and, for example, a $C_1$–$C_4$-alkyl radical described above for $R_A^6$, or a branched or unbranched, optionally substituted C—$C_1$–$C_4$-alkoxy radical which is composed of a carbon radical and, for example, a $C_1$–$C_4$-alkoxy radical described above for $R_A^7$.

$Z^5$ is oxygen, sulfur or an $NR_A^8$ radical.

Preferred structural elements A are composed of the preferred radicals of the structural element.

Particularly preferred structural elements A are composed of the particularly preferred radicals of the structural element.

In a preferred embodiment, the spacer structural element E means a structural element which consists of a branched or unbranched, optionally substituted and heteroatom-containing aliphatic $C_2$–$C_{30}$-hydrocarbon radical and/or of a 4- to 20-membered, optionally substituted and heteroatom-containing, aliphatic or aromatic mono- or polycyclic hydrocarbon radical.

In a particularly preferred embodiment, the spacer structural element E is composed of two to four partial structural elements selected from the group of $E^1$ and $E^2$ together, the partial structural elements being linked in any sequence, and $E^1$ and $E^2$ having the following meanings:

$E^1$ a partial structural element of the formula $I_{E1}$

$I_{E1}$ and $E^2$ a partial structural element of the formula $I_{E2}$

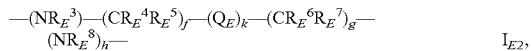

$I_{E2}$, where c, d, f, g
are, independently of one another, 0, 1 or 2, e, h, i, k, l,
are, independently of one another, 0 or 1, $X_E, Q_E$
are, independently of one another, CO, CO—$NR_E^9$, S, SO, $SO_2$, $SO_2NR_E^9$, CS, CS—$NR_E^9$, CS—O, CO—O, O—CO, O, ethynyl, $CR_E^{10}$—O—$CR_E^{11}$, $CR_E^{10}R_E^{11}$, C(=$CR_E^{10}R_E^{11}$), $CR_E^{10}$=$CR_E^{11}$, $CR_E^{10}(OR_E^{12})$—$CR_E^{11}$, $CR_E^{10}$—$CR_E^{11}(OR_E^{12})$ or an optionally substituted 4- to 11-membered mono- or polycyclic aliphatic or aromatic hydrocarbon which may contain up to 6 double bonds and up to 6 heteroatoms selected from the group of N, O, S, $Y_E$ is —CO—, —$NR_E^9$—CO—, —SO—, —$SO_2$—, —$NR_E^9$—$SO_2$—, —CS—, —$NR_E^9$—CS—, —O—CS— or —O—CO—

$R_E^1, R_E^2, R_E^4, R_E^5, R_E^6, R_E^7$
are, independently of one another, hydrogen, halogen, a hydroxyl group, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical, a —$(CH_2)_w$—$R_E^{13}$ radical, an optionally substituted $C_3$–$C_7$-cycloalkyl, aryl, arylalkyl, hetaryl, hetarylalkyl, O-aryl or O-alkylene-aryl radical, or, independently of one another, in each case two radicals $R_E^1$ and $R_E^2$ or $R_E^4$ and $R_E^5$ or $R_E^6$ and $R_E^7$ together are a 3- to 7-membered, optionally substituted, saturated or unsaturated carbocyclic system, where w is 0, 1, 2, 3 or 4, $R_E^3, R_E^8, R_E^9$
are, independently of one another, hydrogen, a branched or unbranched, optionally substituted $C_1$–$C_6$-alkyl, CO—$C_1$–$C_6$-alkyl, CO—O—$C_1$–$C_6$-alkyl or $SO_2$—$C_1$–$C_6$-alkyl radical or an optionally substituted $C_3$–$C_7$-cycloalkyl, CO—O-alkylene-aryl, CO-alkylene-aryl, CO-aryl, $SO_2$-aryl, CO-hetaryl or $SO_2$-alkylene-aryl radical, $R_E^{10}, R_E^{11}$
are, independently of one another, hydrogen, a hydroxyl group, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_E^{12}$ is hydrogen, a branched or unbranched, optionally substituted $C_1$–$C_6$-alkyl, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_E^{13}$ is hydrogen, a hydroxyl group, a branched or unbranched, optionally substituted $C_1$–$C_6$-alkyl, $C_1$–$C_4$-alkoxy, -arylalkyl, —O-alkylene-aryl or —O-aryl radical, an amino radical with primary or, where appropriate, secondary or tertiary substitution, an optionally $C_1$–$C_4$-alkyl- or aryl-substituted $C_2$–$C_6$-alkynyl or $C_2$–$C_6$-alkenyl radical, a $C_5$–$C_{12}$-bicycloalkyl, $C_6$–$C_{18}$-tricycloalkyl radical, a CO—O—$R^{A14}$ radical, or a 3- to 6-membered, saturated or unsaturated heterocyclic system which is substituted by up to three identical or different radicals and which may contain up to three different or identical heteroatoms O, N, S, $C_3$–$C_7$-cycloalkyl, aryl or hetaryl radical, it being possible for two radicals together to be a fused-on, saturated, unsaturated or aromatic carbocyclic or heterocyclic system which may contain up to three different or identical heteroatoms O, N, S, and the ring may optionally be substituted or another, optionally substituted, saturated, unsaturated or aromatic ring may be fused onto this ring.

In an even more preferred embodiment, the spacer structural element E used is a structural element of the formula $I_{E1E2}$ $$—E_2—E_1—  \qquad I_{E1E2}$$

An optionally substituted 4- to 11-membered mono- or polycyclic aliphatic or aromatic hydrocarbon which may contain up to 6 double bonds and up to 6 heteroatoms selected from the group of N, O, S for $Q_E$ and $X_E$ mean, independently of one another, preferably optionally substituted aryl such as, for example, optionally substituted phenyl or naphthyl, optionally substituted hetaryl such as, for example, the radicals

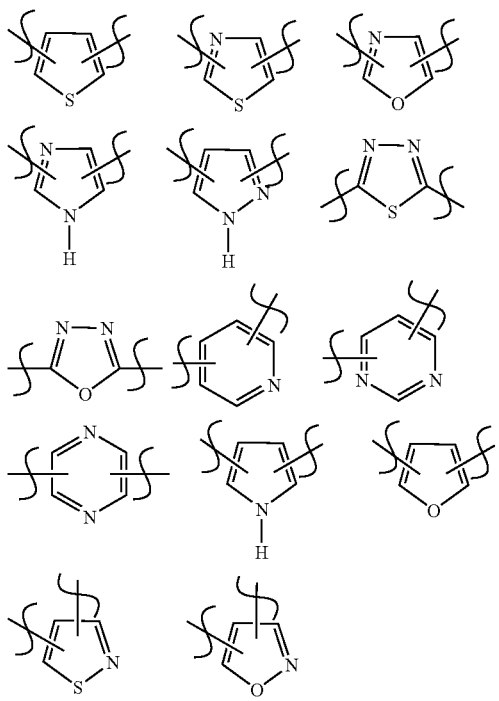

and their substituted derivatives, or radicals of the formulae $I_E^1$ to $I_E^{11}$

 $I_E^1$

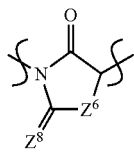 $I_E^2$

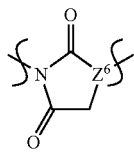 $I_E^3$

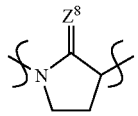 $I_E^4$

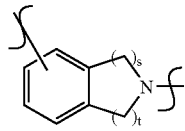 $I_E^5$

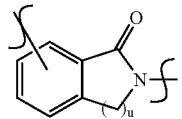 $I_E^6$

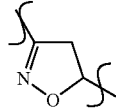 $I_E^7$

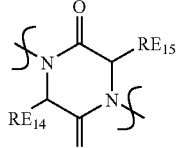 $I_E^8$

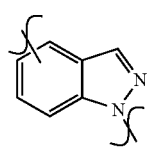 $I_E^9$

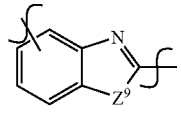 $I_E^{10}$

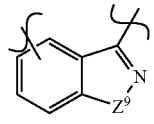 $I_E^{11}$ it being possible for the radicals to be incorporated in both orientations.

$Z^6$ and $Z^7$ are, independently of one another, CH or nitrogen.

$Z^8$ is oxygen, sulfur or NH.

$Z^9$ is oxygen, sulfur or $NR_E^{16}$.

r and t are, independently of one another, 0, 1, 2 or 3.

s and u are, independently of one another, 0, 1 or 2.

$R_E^{14}$ and $R_E^{15}$ are, independently of one another, hydrogen, —NO$_2$, —NH$_2$, —CN, —COOH, a hydroxyl group, halogen, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical or an optionally substituted cycloalkyl, aryl, arylalkyl, hetaryl or hetarylalkyl radical as described above in each case.

$R_E^{16}$ means, independently of one another, hydrogen, a branched or unbranched, optionally substituted $C_1$–$C_6$-alkyl, $C_1$–$C_6$-alkoxyalkyl, $C_3$–$C_{12}$-alkynyl, CO—$C_1$–$C_6$-alkyl, CO—O—$C_1$–$C_6$-alkyl or $SO_2$—$C_1$–$C_6$-alkyl radical or an optionally substituted $C_3$–$C_7$-cycloalkyl, aryl, arylalkyl, CO—O—alkylene-aryl, CO-alkylene-aryl, CO-aryl, $SO_2$-aryl, hetaryl, CO-hetaryl or $SO_2$-alkylene-aryl radical, preferably hydrogen or a branched or unbranched, optionally substituted $C_1$–$C_6$-alkyl radical.

Preferred radicals for $Q_E$ are the radicals CO, CO—$NR_E^9$, S, SO, $SO_2$, $SO_2NR_E^9$, CS, CS—$NR_E^9$, CS—O, CO—O, O—CO, o, ethynyl, $CR_E^{10}$—O—$CR_E^{11}$, $CR_E^{10}R_E^{11}$, C(=$CR_E^{10}R_E^{11}$), $CR_E^{10}$=$CR_E^{11}$, $R_E^{10}(OR_E^{12})$—$CR_E^{11}$, $CR_E^{10}$—$CR_E^{11}(OR_E^{12})$, substituted aryl or hetaryl as described above, or the radicals of the formulae $I_E^1$ to $I_E^{11}$.

Particularly preferred radicals for $Q_E$ are the radicals CO, CO—$NR_E^9$, S, SO, $SO_2$, $SO_2NR_E^9$, CS, CS—$NR_E^9$, CS—O, CO—O, O—CO, O, ethynyl, $CR_E^{10}$—O—$CR_E^{11}$, $CR_E^{10}R_E^{11}$, C(=$CR_E^{10}R_E^{11}$), $CR_E^{10}$=$CR_E^{11}$, $CR_E^{10}(OR_E^{12})$—$CR_E^{11}$, $CR_E^{10}$—$CR_E^{11}(OR_E^{12})$, substituted aryl or hetaryl as described above, or the radicals of the formulae $I_E^1$, $I_E^4$, $I_E^6$, $I_E^7$, $I_E^9$ or $I_E^{10}$.

Preferred radicals for $X_E$ are the radicals CO, CO—$NR_E^9$, S, $SO_2NR_E^9$, CS, CS—$NR_E^9$, CO—O, O—CO, O, ethynyl, $CR_E^{10}$—O—$CR_E^{11}$, $CR_E^{10}R_E^{11}$ or $CR_E^{10}$=$CR_E^{11}$, particularly preferably CO, CO—$NR_E^9$, $SO_2NR_E^9$, O, ethynyl, $CR_E^{10}$—O—$CR_E^{11}$ or $CR_E^{10}R_E^{11}$.

Preferred radicals for $R_E^1$ are hydrogen, fluorine, chlorine or a —$(CH_2)_w$—$R_E^{13}$ radical, where w is 0, 1, 2, 3 or 4.

Preferred radicals for $R_E^2$ are hydrogen, halogen, particularly preferably chlorine or fluorine, a hydroxyl group or a branched or unbranched, optionally substituted $C_1$–$C_6$-alkyl or $C_1$–$C_4$-alkoxy radical, particularly preferably methyl or ethyl.

In a further preferred embodiment, the two radicals $R_E^1$ and $R_E^2$ together form a 3- to 7-membered, optionally substituted, saturated, unsaturated or aromatic carbocyclic system.

The preferred and particularly preferred radicals for $R_E^4$ and $R_E^6$ and for $R_E^5$ and $R_E^7$ are, independently of one another, in each case the corresponding radicals which are the same as mentioned above for $R_E^1$ and $R_E^2$.

It is once again possible, in a preferred embodiment, for the radicals $R_E^4$ and $R_E^5$ or $R_E^6$ and $R_E^7$ together to form a 3- to 7-membered, optionally substituted carbocyclic system in this case.

Preferred radicals for $R_E^3$ are hydrogen or a branched or unbranched, optionally substituted $C_1$–$C_6$-alkyl radical, particularly preferably methyl.

Preferred radicals for $R_E^8$ and $R_E^9$ are, independently of one another, hydrogen, a branched or unbranched, optionally substituted $C_1$–$C_4$-alkyl, $C_3$–$C_7$-cycloalkyl, CO—$C_1$–$C_4$-alkyl, CO—O—alkylene-aryl, particularly preferably CO—O—benzyl, CO-alkylene-aryl, particularly preferably CO-phenyl, CO—O—$C_1$–$C_4$-alkyl, $SO_2$—$C_1$–$C_4$-alkyl, $SO_2$-aryl, particularly preferably tosyl or $SO_2$-alkylene-aryl radical.

Preferred radicals for $R_E^{10}$ and $R_E^{11}$ are, independently of one another, hydrogen, a hydroxyl group, a branched or unbranched, optionally substituted $C_1$–$C_6$-alkyl, particularly preferably $C_1$–$C_4$-alkyl, or $C_1$–$C_4$-alkoxy radical or an optionally substituted aryl, arylalkyl, hetaryl or hetarylalkyl radical.

Preferred radicals for $R_E^{12}$ are, independently of one another, hydrogen, a branched or unbranched, optionally substituted $C_1$–$C_6$-alkyl radical or an optionally substituted arylalkyl or hetarylalkyl radical.

A branched or unbranched $C_1$–$C_6$-alkyl radical for $R_E^{13}$ means, for example, methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, preferably methyl, ethyl, propyl, butyl, isopropyl, sec-butyl and tert-butyl.

A branched or unbranched $C_1$–$C_4$-alkoxy radical for $R_E^{13}$ means, for example, methoxy, ethoxy, propoxy, 1-methylethoxy, butoxy, 1-methylpropoxy, 2-methylpropoxy or 1,1-dimethylethoxy, in particular methoxy, ethoxy or 1-methylethoxy.

Examples of —O-alkylene-aryl or —O-aryl radicals are —O-phenyl, —O-1-naphthyl, —O-2-naphthyl or —O-benzyl.

The $C_1$–$C_6$-alkyl and $C_1$–$C_4$-alkoxy radicals of $R_E^{13}$ may be substituted by up to five identical or different substituents as described at the outset.

Substituted —O-alkylene-aryl or —O-aryl radicals mean, for example, the abovementioned —O-alkylene-aryl or —O-aryl radicals, it being possible for the aryl moiety to be substituted by up to three identical or different substituents as described at the outset.

An amino radical with primary or, where appropriate, secondary or tertiary substitution for $R_E^{13}$ in structural element L means a primary amino radical —$NH_2$, a secondary amino radical —$NH(R_E^{131})$ or a tertiary amino radical —$N(R_E^{131})(R_E^{132})$, where $R_E^{131}$ and $R_E^{132}$ can be, independently of one another, $C_1$–$C_4$-alkyl or $C_3$–$C_6$-cycloalkyl as mentioned above, optionally substituted aryl, preferably phenyl, arylalkyl, preferably benzyl, —CO—$C_1$–$C_4$-alkyl, preferably —CO—$CH_3$ or —CO-aryl, preferably —CO-phenyl.

Cyclic amino radicals result in the case where $R_E^{13}$ is one of the heterocycles described below, which is bonded via the ring nitrogen.

An optionally $C_1$–$C_4$-alkyl- or aryl-substituted $C_2$–$C_6$-alkynyl or $C_2$–$C_6$-alkenyl radical for $R_E^{13}$ means, for example, $C_2$–$C_6$-alkynyl radicals such as, for example, ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl or ethynyl or $C_2$–$C_6$-alkenyl radical, such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2- butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl or vinyl, each of which may be substituted by optionally substituted $C_1$–$C_4$-alkyl radicals or aryl radicals as mentioned above, preferably phenyl, such as, preferably, phenylethynyl or phenylethenyl.

A $C_5$–$C_{12}$-bicycloalkyl radical for $R_E^{13}$ means, for example, indanyl, norbornyl or camphyl, and a $C_6$–$C_{18}$-tricycloalkyl radical means, for example, adamantyl.

The CO—O—$R_A^{14}$ radical is composed, as mentioned above several times, of the group CO—O and the $R_A^{14}$ radical described above for structural element A.

A 3- to 6-membered, saturated or unsaturated heterocyclic system which is substituted by up to three identical or different radicals and may contain up to three different or identical heteroatoms O, N, S, or $C_3$–$C_8$-cycloalkyl, aryl or heteroaryl radical, it being possible for two radicals together to be a fused-on, 3- to 7-membered, saturated, unsaturated or aromatic carbocyclic or heterocyclic system which may contain up to three different or identical heteroatoms O, N, S, and the ring can optionally be substituted, or another, optionally substituted, saturated, unsaturated or aromatic ring may be fused onto this ring, for $R_E^{13}$ means, for example, 3- to 6-membered, saturated or unsaturated heterocycles which may contain up to three different or identical heteroatoms O, N, S, such as N-pyrrolidinyl, N-piperidinyl, N-hexahydroazepinyl, N-morpholinyl or N-piperazinyl, and in the case of heterocycles which have free amine protons, such as, for example, N-piperazinyl, the free amine protons may be replaced by conventional amine protective groups, such as, for example, methyl, benzyl, boc (tert-butoxycarbonyl), Z (benzyloxycarbonyl), tosyl, —$SO_2$—$C_1$–$C_4$-alkyl, —$SO_2$-phenyl or —$SO_2$-benzyl, $C_3$–$C_7$-cycloalkyl radicals as described above for $R_L^1$, aryl radicals such as, for example, phenyl, 1-naphthyl or 2-naphthyl or hetaryl radicals such as, for example, 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 1,3,4-thiadiazol-2-yl, 1,3,4-oxadiazol-2-yl, 3-isoxazolyl, 4-isoxazolyl, 5-isoxazolyl or triazinyl, preferably 2-pyridyl, 3-pyridyl, 4-pyridyl, 2-furyl, 3-furyl, 2-thienyl, 3-thienyl, 2-thiazolyl, 4-thiazolyl or 5-thiazolyl, it being possible for the heterocyclic, $C_3$–$C_7$-cycloalkyl, aryl and heteroaryl radicals optionally to be substituted by up to three identical or different radicals.

Preferred substituents of the heterocyclic, $C_3$–$C_8$-cycloalkyl, aryl and hetaryl radicals for $R_E^{13}$ are $C_1$–$C_4$-alkyl, —COOH, —COOMe, —$CF_3$, —CN, $C_1$–$C_4$-alkoxy, —$SCH_3$, —O—$CH_2$—COOH, -phenyl, —$SO_2CH_3$, —$NO_2$, —OH, —$NH_2$, —N-pyrrolidinyl, —N-piperidinyl, —N-morpholinyl, —N-piperazinyl, —NH—$C_1$–$C_4$-alkyl, —N($C_1$–$C_4$-alkyl)$_2$, F, Cl, Br or I.

With the hetaryl radicals it is also possible for two radicals together to form, as described above generally, a fused-on system.

Preferred substituents of the heterocyclic, $C_3$–$C_8$-cycloalkyl, aryl and hetaryl radicals for $R_E^{13}$ in which two radicals together are a fused-on, saturated, unsaturated or aromatic carbocyclic or heterocyclic system which may contain up to three different or identical heteroatoms O, N, S, and the ring may optionally be substituted or another, optionally substituted ring may be fused onto this ring, are the following doubly linked structural elements:

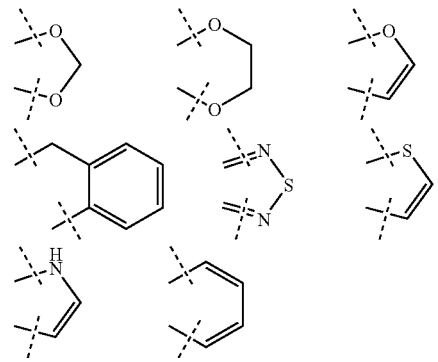

Examples of the resulting fused cyclic systems for $R_E^{13}$ are, for example, the corresponding dioxolanyls, benzopyrrolyls, benzofuryls, benzothienyls or fluorenyls.

Preferred structural elements E are composed of the preferred radicals for structural element E.

Preferred structural elements B are composed of the preferred structural elements A and E.

The compounds of the formula I and the intermediates for their preparation may have one or more asymmetric substituted carbon atoms. The compounds may be in the form of pure enantiomers or pure diastereomers or a mixture thereof. The use of an enantiomerically pure compound as active ingredient is preferred.

The compounds of the formula I may also be in the form of physiologically tolerated salts.

The compounds of the formula I may also be in the form of prodrugs where the compounds of the formula I are released under physiological conditions. Reference may be made in this connection by way of example to group T in structural element L, which group contains some groups which can be hydrolyzed under physiological conditions to the free carboxyl group. Also suitable are derivatized structural elements B or A which release the structural element B or A under physiological conditions.

In preferred compounds of the formula I, in each case one of the three structural elements B, G or L has the preferred range, while the remaining structural elements may vary widely.

In particularly preferred compounds of the formula I, in each case two of the three structural elements B, G or L have the preferred range, while the remaining structural elements may vary widely.

In very particularly preferred compounds of the formula I, in each case all three structural elements B, G or L have the preferred range, while the remaining structural element may vary widely.

Preferred compounds of the formula I have, for example, the preferred structural element G, while the structural elements B and L may vary widely.

In particularly preferred compounds of the formula I, for example, B is replaced by the structural element A—E—, and the compounds have, for example, the preferred structural element G and the preferred structural element A, while the structural elements E and L may vary widely.

Further particularly preferred compounds have, for example, the preferred structural element G and the preferred structural element A, while the structural elements E and L may vary widely.

Very preferred compounds of the formula I in which A—E— represents B— are listed in the following table, where "compound" represents the number of an individualized compound of the formula I, and the meaning of the abbreviations of the structural elements is explained after the table.

| Compound | Structural elements A-E-G-L |
|---|---|
| 1 | 2pmhs-am2-pheac-es |
| 2 | 2pmhs-dibema2-phec-gs |
| 3 | 2pmhs-edia2-phec-es |
| 4 | 2py-25thima2-pheaz-es |
| 5 | 2py-25thima2-phec-es |
| 6 | 2py-35thima2-pheaz-es |
| 7 | 2py-35thima2-phec-es |
| 8 | 2py-42thiaz2-pheaz-es |
| 9 | 2py-42thiaz2-phec-es |
| 10 | 2py-aaf-pheaz-es |
| 11 | 2py-aaf-phec-es |
| 12 | 2py-am2-8mephec-es |
| 13 | 2py-am2-8mephec-gs |
| 14 | 2py-am2-8mephec-ps |
| 15 | 2py-am2-deophec-es |
| 16 | 2py-am2-deophec-gs |
| 17 | 2py-am2-deophec-ps |
| 18 | 2py-am2-pheaz-es |
| 19 | 2py-am2-pheaz-ps |
| 20 | 2py-am2-phec-es |
| 21 | 2py-am2-phec-gs |
| 22 | 2py-am2-phec-ps |
| 23 | 2py-am2-thioph-es |
| 24 | 2py-am2-thioph-gs |
| 25 | 2py-am2-thioph-ps |
| 26 | 2py-aof-pheaz-es |
| 27 | 2py-aof-phec-es |
| 28 | 2py-buta-pheaz-es |
| 29 | 2py-buta-phec-es |
| 30 | 2py-chex2-pheaz-es |
| 31 | 2py-chex2-phec-es |
| 32 | 2py-dibema2-23dimephec-es |
| 33 | 2py-dibema2-27dimeophec-es |
| 34 | 2py-dibema2-2mephec-es |
| 35 | 2py-dibema2-49dimeophec-es |
| 36 | 2py-dibema2-5claz-es |
| 37 | 2py-dibema2-69dimeophec-es |
| 38 | 2py-dibema2-69dimephec-es |
| 39 | 2py-dibema2-78diclphec-es |
| 40 | 2py-dibema2-78dimeophec-es |
| 41 | 2py-dibema2-8mephec-es |
| 42 | 2py-dibema2-8mephec-gs |
| 43 | 2py-dibema2-8mephec-ps |
| 44 | 2py-dibema2-8mepyaz-es |
| 45 | 2py-dibema2-9clphec-es |
| 46 | 2py-dibema2-benz-es |
| 47 | 2py-dibema2-cl2phec-es |
| 48 | 2py-dibema2-deophec-es |
| 49 | 2py-dibema2-deophec-gs |
| 50 | 2py-dibema2-deophec-ps |
| 51 | 2py-dibema2-deothioph-es |
| 52 | 2py-dibema2-dimepy-es |
| 53 | 2py-dibema2-dimepyaz-es |
| 54 | 2py-dibema2-dimethio-es |
| 55 | 2py-dibema2-dmaphec-es |
| 56 | 2py-dibema2-imon-es |
| 57 | 2py-dibema2-meoaz-es |
| 58 | 2py-dibema2-meophe-es |
| 59 | 2py-dibema2-meophe-nes |
| 60 | 2py-dibema2-meophe-f2es |
| 61 | 2py-dibema2-mephe-gs |
| 62 | 2py-dibema2-pheaz-es |
| 63 | 2py-dibema2-pheaz-ps |
| 64 | 2py-dibema2-phec-es |
| 65 | 2py-dibema2-phec-gs |
| 66 | 2py-dibema2-phec-ps |
| 67 | 2py-dibema2-phec-pms |
| 68 | 2py-dibema2-phec-ms |
| 69 | 2py-dibema2-phec-mals |
| 70 | 2py-dibema2-phedb-as |
| 71 | 2py-dibema2-phepyra-es |
| 72 | 2py-dibema2-pyphc-es |
| 73 | 2py-dibema2-sulfo-es |
| 74 | 2py-dibema2-thiomet-es |
| 75 | 2py-dibema2-thioph-es |
| 76 | 2py-dibema2-thioph-gs |
| 77 | 2py-dibema2-thioph-ps |
| 78 | 2py-dibema2-thioph2-es |
| 79 | 2py-dibema2-thiophaz-es |
| 80 | 2py-edia2-8mephec-es |
| 81 | 2py-edia2-8mephec-gs |
| 82 | 2py-edia2-8mephec-ps |
| 83 | 2py-edia2-deophec-es |
| 84 | 2py-edia2-deophec-gs |
| 85 | 2py-edia2-deophec-ps |
| 86 | 2py-edia2-pheaz-es |
| 87 | 2py-edia2-pheaz-ps |
| 88 | 2py-edia2-phec-es |
| 89 | 2py-edia2-phec-gs |
| 90 | 2py-edia2-phec-ps |
| 91 | 2py-edia2-phec-mals |
| 92 | 2py-edia2-thioph-es |
| 93 | 2py-edia2-thioph-gs |
| 94 | 2py-edia2-thioph-ps |
| 95 | 2py-edia2-23dimephec-es |
| 96 | 2py-edia2-27dimeophec-es |
| 97 | 2py-edia2-2mephec-es |
| 98 | 2py-edia2-49dimeophec-es |
| 99 | 2py-edia2-5claz-es |
| 100 | 2py-edia2-69dimeophec-es |
| 101 | 2py-edia2-69dimephec-es |
| 102 | 2py-edia2-78diclphec-es |
| 103 | 2py-edia2-78dimeophec-es |
| 104 | 2py-edia2-8mepyaz-es |
| 105 | 2py-edia2-9clphec-es |
| 106 | 2py-edia2-benz-es |
| 107 | 2py-edia2-cl2phec-es |
| 108 | 2py-edia2-deothioph-es |
| 109 | 2py-edia2-dimepy-es |
| 110 | 2py-edia2-dimepyaz-es |
| 111 | 2py-edia2-dimethio-es |
| 112 | 2py-edia2-dmaphec-es |
| 113 | 2py-edia2-imon-es |
| 114 | 2py-edia2-meoaz-es |
| 115 | 2py-edia2-meophe-es |
| 116 | 2py-edia2-meophe-nes |
| 117 | 2py-edia2-meophe-f2es |
| 118 | 2py-edia2-mephe-gs |
| 119 | 2py-edia2-phec-pms |
| 120 | 2py-edia2-phec-ms |
| 121 | 2py-edia2-phedb-as |
| 122 | 2py-edia2-phepyra-es |
| 123 | 2py-edia2-pyphc-es |
| 124 | 2py-edia2-sulfo-es |
| 125 | 2py-edia2-thiomet-es |
| 126 | 2py-edia2-thioph2-es |
| 127 | 2py-edia2-thiophaz-es |
| 128 | 2py-edia2-6pyme-pheaz-es |
| 129 | 2py-edia2-6pyme-phec-es |
| 130 | 2py-edia3-pheaz-es |
| 131 | 2py-edia3-phec-es |
| 132 | 2py-edia3-6pyme-pheaz-es |
| 133 | 2py-edia3-6pyme-phec-es |
| 134 | 2py-edia4-2oxaz-pheaz-es |
| 135 | 2py-edia4-2oxaz-phec-es |

-continued

| Compound | Structural elements A-E-G-L |
|---|---|
| 136 | 2py-edia4-2thiaz-pheaz-es |
| 137 | 2py-edia4-2thiaz-phec-es |
| 138 | 2py-ediammebz-pheaz-es |
| 139 | 2py-ediammebz-phec-es |
| 140 | 2py-ediapmebz-pheaz-es |
| 141 | 2py-ediapmebz-phec-es |
| 142 | 2py-hexa-pheaz-es |
| 143 | 2py-hexa-phec-es |
| 144 | 2py-inda2-pheaz-es |
| 145 | 2py-inda2-phec-es |
| 146 | 2py-me25thima2-pheaz-es |
| 147 | 2py-me25thima2-phec-es |
| 148 | 2py-me35thima2-pheaz-es |
| 149 | 2py-me35thima2-phec-es |
| 150 | 2py-me42thiaz2-pheaz-es |
| 151 | 2py-me42thiaz2-phec-es |
| 152 | 2py-mea26pyme-pheaz-es |
| 153 | 2py-mea26pyme-phec-es |
| 154 | 2py-mea3-pheaz-es |
| 155 | 2py-mea3-phec-es |
| 156 | 2py-mea36pyme-pheaz-es |
| 157 | 2py-mea36pyme-phec-es |
| 158 | 2py-mea42oxaz-pheaz-es |
| 159 | 2py-mea42oxaz-phec-es |
| 160 | 2py-mea42thiaz-pheaz-es |
| 161 | 2py-mea42thiaz-phec-es |
| 162 | 2py-meammebz-pheaz-es |
| 163 | 2py-meammebz-phec-es |
| 164 | 2py-meapmebz-pheaz-es |
| 165 | 2py-meapmebz-phec-es |
| 166 | 2py-mepipe2-pheaz-es |
| 167 | 2py-mepipe2-phec-es |
| 168 | 2py-mepyma2-pheaz-es |
| 169 | 2py-mepyma2-phec-es |
| 170 | 2py-penta-8mephec-es |
| 171 | 2py-penta-8mephec-gs |
| 172 | 2py-penta-8mephec-ps |
| 173 | 2py-penta-deophec-es |
| 174 | 2py-penta-deophec-gs |
| 175 | 2py-penta-deophec-ps |
| 176 | 2py-penta-pheaz-es |
| 177 | 2py-penta-pheaz-ps |
| 178 | 2py-penta-phec-es |
| 179 | 2py-penta-phec-gs |
| 180 | 2py-penta-phec-ps |
| 181 | 2py-penta-thioph-es |
| 182 | 2py-penta-thioph-gs |
| 183 | 2py-penta-thioph-ps |
| 184 | 2py-pipa2-pheaz-es |
| 185 | 2py-pipa2-phec-es |
| 186 | 2py-pipeme2-pheaz-es |
| 187 | 2py-pipeme2-phec-es |
| 188 | 2py-pyma2-pheaz-es |
| 189 | 2py-pyma2-phec-es |
| 190 | 3pmhs-am2-pheac-es |
| 191 | 3pmhs-dibema2-phec-gs |
| 192 | 3pmhs-edia2-phec-es |
| 193 | 4pmhs-am2-pheac-es |
| 194 | 4pmhs-dibema2-phec-gs |
| 195 | 4pmhs-edia2-phec-es |
| 196 | agua-am2-pheac-es |
| 197 | agua-dibema2-phec-gs |
| 198 | agua-edia2-phec-es |
| 199 | am2py-am2-8mephec-ps |
| 200 | am2py-am2-8mephec-gs |
| 201 | am2py-am2-8mephec-es |
| 202 | am2py-am2-pheac-es |
| 203 | am2py-am2-pheaz-ps |
| 204 | am2py-am2-pheaz-gs |
| 205 | am2py-am2-pheaz-es |
| 206 | am2py-am2-phec-ps |
| 207 | am2py-am2-phec-gs |
| 208 | am2py-am2-phec-es |
| 209 | am2py-am2-phec-es |
| 210 | am2py-am2-phec-gs |
| 211 | am2py-am2-thioph-ps |
| 212 | am2py-am2-thioph-gs |
| 213 | am2py-am2-thioph-es |
| 214 | am2py-mea42thiaz-8mephec-ps |
| 215 | am2py-mea42thiaz-8mephec-gs |
| 216 | am2py-mea42thiaz-8mephec-es |
| 217 | am2py-mea42thiaz-pheaz-ps |
| 218 | am2py-mea42thiaz-pheaz-gs |
| 219 | am2py-mea42thiaz-pheaz-es |
| 220 | am2py-mea42thiaz-phec-ps |
| 221 | am2py-mea42thiaz-phec-gs |
| 222 | am2py-mea42thiaz-phec-es |
| 223 | am2py-mea42thiaz-thioph-ps |
| 224 | am2py-mea42thiaz-thioph-gs |
| 225 | am2py-mea42thiaz-thioph-es |
| 226 | am4py-am2-pheac-es |
| 227 | am4py-dibema2-phec-gs |
| 228 | am4py-edia2-phec-es |
| 229 | amhyd-am2-pheac-es |
| 230 | amhyd-am2-phec-es |
| 231 | amhyd-am2-phec-gs |
| 232 | amim-am2-pheac-es |
| 233 | amim-am2-phec-es |
| 234 | amim-am2-phec-gs |
| 235 | amthiz-am2-pheac-es |
| 236 | amthiz-dibema2-phec-gs |
| 237 | amthiz-edia2-phec-es |
| 238 | amtriz-am2-pheac-es |
| 239 | amtriz-dibema2-phec-gs |
| 240 | amtriz-edia2-phec-es |
| 241 | bgua-am2-pheac-es |
| 242 | bgua-dibema2-phec-gs |
| 243 | bgua-edia2-phec-es |
| 244 | bhs-25thima2-phec-gs |
| 245 | bhs-35thima2-phec-gs |
| 246 | bhs-42thiaz2-phec-gs |
| 247 | bhs-aaf-phec-gs |
| 248 | bhs-am2-8mephec-es |
| 249 | bhs-am2-8mephec-gs |
| 250 | bhs-am2-8mephec-ps |
| 251 | bhs-am2-deophec-es |
| 252 | bhs-am2-deophec-gs |
| 253 | bhs-am2-deophec-ps |
| 254 | bhs-am2-pheaz-es |
| 255 | bhs-am2-pheaz-ps |
| 256 | bhs-am2-phec-es |
| 257 | bhs-am2-phec-gs |
| 258 | bhs-am2-phec-ps |
| 259 | bhs-am2-thioph-es |
| 260 | bhs-am2-thioph-gs |
| 261 | bhs-am2-thioph-ps |
| 262 | bhs-aof-phec-gs |
| 263 | bhs-buta-phec-gs |
| 264 | bhs-chex2-phec-gs |
| 265 | bhs-dibema2-23dimephec-es |
| 266 | bhs-dibema2-27dimeophec-es |
| 267 | bhs-dibema2-2mephec-es |
| 268 | bhs-dibema2-49dimeophec-es |
| 269 | bhs-dibema2-5claz-es |
| 270 | bhs-dibema2-69dimeophec-es |
| 271 | bhs-dibema2-69dimephec-es |
| 272 | bhs-dibema2-78diclphec-es |
| 273 | bhs-dibema2-78dimeophec-es |
| 274 | bhs-dibema2-8mephec-es |
| 275 | bhs-dibema2-8mephec-gs |
| 276 | bhs-dibema2-8mephec-es |
| 277 | bhs-dibema2-8mepyaz-es |
| 278 | bhs-dibema2-9clphec-es |
| 279 | bhs-dibema2-benz-es |
| 280 | bhs-dibema2-cl2phec-es |
| 281 | bhs-dibema2-deophec-es |
| 282 | bhs-dibema2-deophec-gs |
| 283 | bhs-dibema2-deophec-ps |
| 284 | bhs-dibema2-deothioph-es |
| 285 | bhs-dibema2-dimepy-es |
| 286 | bhs-dibema2-dimepyaz-es |
| 287 | bhs-dibema2-dimethio-es |
| 288 | bhs-dibema2-dmaphec-es |
| 289 | bhs-dibema2-imones |

-continued

| Compound | Structural elements A-E-G-L |
|---|---|
| 290 | bhs-dibema2-meoaz-es |
| 291 | bhs-dibema2-meophe-es |
| 292 | bhs-dibema2-meophe-nes |
| 293 | bhs-dibema2-meophe-f2es |
| 294 | bhs-dibema2-mephe-gs |
| 295 | bhs-dibema2-pheaz-es |
| 296 | bhs-dibema2-pheaz-ps |
| 297 | bhs-dibema2-phec-es |
| 298 | bhs-dibema2-phec-gs |
| 299 | bhs-dibema2-phec-ps |
| 300 | bhs-dibema2-phec-pms |
| 301 | bhs-dibema2-phec-ms |
| 302 | bhs-dibema2-phec-mals |
| 303 | bhs-dibema2-phedb-as |
| 304 | bhs-dibema2-phepyra-es |
| 305 | bhs-dibema2-pyphc-es |
| 306 | bhs-dibema2-sulfo-es |
| 307 | bhs-dibema2-thiomet-es |
| 308 | bhs-dibema2-thioph-es |
| 309 | bhs-dibema2-thioph-gs |
| 310 | bhs-dibema2-thioph-ps |
| 311 | bhs-dibema2-thioph2-es |
| 312 | bhs-dibema2-thiophaz-es |
| 313 | bhs-edia2-8mephec-es |
| 314 | bhs-edia2-8mephec-gs |
| 315 | bhs-edia2-8mephec-ps |
| 316 | bhs-edia2-deophec-es |
| 317 | bhs-edia2-deophec-gs |
| 318 | bhs-edia2-deophec-ps |
| 319 | bhs-edia2-pheaz-es |
| 320 | bhs-edia2-pheaz-ps |
| 321 | bhs-edia2-phec-es |
| 322 | bhs-edia2-phec-gs |
| 323 | bhs-edia2-phec-ps |
| 324 | bhs-edia2-thioph-es |
| 325 | bhs-edia2-thioph-gs |
| 326 | bhs-edia2-thioph-ps |
| 327 | bhs-edia2-6pyme-phec-gs |
| 328 | bhs-edia3-phec-gs |
| 329 | bhs-edia3-6pyme-phec-gs |
| 330 | bhs-edia42oxaz-phec-gs |
| 331 | bhs-edia42thiaz-phec-gs |
| 332 | bhs-ediammebz-phec-gs |
| 333 | bhs-ediapmebz-phec-gs |
| 334 | bhs-hexa-phec-gs |
| 335 | bhs-inda2-phec-gs |
| 336 | bhs-me25thima2-phec-gs |
| 337 | bhs-me35thima2-phec-gs |
| 338 | bhs-me42thiaz2-phec-gs |
| 339 | bhs-mea26pyme-phec-gs |
| 340 | bhs-mea3phec-gs |
| 341 | bhs-mea36pyme-phec-gs |
| 342 | bhs-mea42oxaz-phec-gs |
| 343 | bhs-mea42thiaz-phec-gs |
| 344 | bhs-meammebz-phec-gs |
| 345 | bhs-meapmebz-phec-gs |
| 346 | bhs-mepipe2-phec-gs |
| 347 | bhs-mepyma2-phec-gs |
| 348 | bhs-penta-8mephec-es |
| 349 | bhs-penta-8mephec-gs |
| 350 | bhs-penta-8mephec-ps |
| 351 | bhs-penta-deophec-es |
| 352 | bhs-penta-deophec-gs |
| 353 | bhs-penta-deophec-ps |
| 354 | bhs-penta-pheaz-es |
| 355 | bhs-penta-pheaz-ps |
| 356 | bhs-penta-phec-es |
| 357 | bhs-penta-phec-gs |
| 358 | bhs-penta-phec-ps |
| 359 | bhs-penta-thioph-es |
| 360 | bhs-penta-thioph-gs |
| 361 | bhs-penta-thioph-ps |
| 362 | bhs-pipa2-phec-gs |
| 363 | bhs-pipeme2-phec-gs |
| 364 | bhs-pyma2-phec-gs |
| 365 | bim-25thima2-pheaz-es |
| 366 | bim-35thima2-pheaz-es |

-continued

| Compound | Structural elements A-E-G-L |
|---|---|
| 367 | bim-42thiaz2-pheaz-es |
| 368 | bim-aaf-pheaz-es |
| 369 | bim-am2-23dimephec-gs |
| 370 | bim-am2-27dimeophec-gs |
| 371 | bim-am2-2mephec-gs |
| 372 | bim-am2-49dimeophec-gs |
| 373 | bim-am2-69dimeophec-gs |
| 374 | bim-am2-69dimephec-gs |
| 375 | bim-am2-78diclphec-gs |
| 376 | bim-am2-78dimeophec-gs |
| 377 | bim-am2-8mephec-es |
| 378 | bim-am2-8mephec-gs |
| 379 | bim-am2-8mephec-ps |
| 380 | bim-am2-9clphec-gs |
| 381 | bim-am2-cl2phec-gs |
| 382 | bim-am2-deophec-es |
| 383 | bim-am2-deophec-gs |
| 384 | bim-am2-deophec-ps |
| 385 | bim-am2-deothioph-gs |
| 386 | bim-am2-dimepy-gs |
| 387 | bim-am2-dimethio-gs |
| 388 | bim-am2-dmaphec-gs |
| 389 | bim-am2-imon-gs |
| 390 | bim-am2-meophe-nes |
| 391 | bim-am2-meophe-f2es |
| 392 | bim-am2-mephe-gs |
| 393 | bim-am2-pheaz-es |
| 394 | bim-am2-pheaz-ps |
| 395 | bim-am2-phec-es |
| 396 | bim-am2-phec-gs |
| 397 | bim-am2-phec-ps |
| 398 | bim-am2-phec-pms |
| 399 | bim-am2-phec-ms |
| 400 | bim-am2-phec-mals |
| 401 | bim-am2-phedb-as |
| 402 | bim-am2-phepyra-gs |
| 403 | bim-am2-pyphc-gs |
| 404 | bim-am2-sulfo-gs |
| 405 | bim-am2-thiomet-gs |
| 406 | bim-am2thioph-es |
| 407 | bim-am2-thioph-gs |
| 408 | bim-am2-thioph-ps |
| 409 | bim-am2-thioph2-gs |
| 410 | bim-aof-pheaz-es |
| 411 | bim-buta-pheaz-es |
| 412 | bim-chex2-pheaz-es |
| 413 | bim-dibema2-8mephec-es |
| 414 | bim-dibema2-8mephec-gs |
| 415 | bim-dibema2-8mephec-ps |
| 416 | bim-dibema2-deophec-es |
| 417 | bim-dibema2-deophec-gs |
| 418 | bim-dibema2-deophec-ps |
| 419 | bim-dibema2-pheaz-es |
| 420 | bim-dibema2-pheaz-ps |
| 421 | bim-dibema2-phec-es |
| 422 | bim-dibema2-phec-gs |
| 423 | bim-dibema2-phec-ps |
| 424 | bim-dibema2-thioph-es |
| 425 | bim-dibema2-thioph-gs |
| 426 | bim-dibema2-thioph-ps |
| 427 | bim-edia2-8mephec-es |
| 428 | bim-edia2-8mephec-gs |
| 429 | bim-edia2-8mephec-ps |
| 430 | bim-edia2-deophec-es |
| 431 | bim-edia2-deophec-gs |
| 432 | bim-edia2-deophec-ps |
| 433 | bim-edia2-pheaz-es |
| 434 | bim-edia2-pheaz-ps |
| 435 | bim-edia2-phec-es |
| 436 | bim-edia2-phec-gs |
| 437 | bim-edia2-phec-ps |
| 438 | bim-edia2-thioph-es |
| 439 | bim-edia2-thioph-gs |
| 440 | bim-edia2-thioph-ps |
| 441 | bim-edia26pyme-pheaz-es |
| 442 | bim-edia3-pheaz-es |
| 443 | bim-edia36pyme-pheaz-es |

-continued

| Compound | Structural elements A-E-G-L |
|---|---|
| 444 | bim-edia42oxaz-pheaz-es |
| 445 | bim-edia42thiaz-pheaz-es |
| 446 | bim-ediammebz-pheaz-es |
| 447 | bim-ediapmebz-pheaz-es |
| 448 | bim-hexa-pheaz-es |
| 449 | bim-inda2-pheaz-es |
| 450 | bim-me25thima2-pheaz-es |
| 451 | bim-me35thima2-pheaz-es |
| 452 | bim-me42thiaz2-pheaz-es |
| 453 | bim-mea26pyme-pheaz-es |
| 454 | bim-mea3-pheaz-es |
| 455 | bim-mea36pyme-pheaz-es |
| 456 | bim-mea42oxaz-pheaz-es |
| 457 | bim-mea42thiaz-pheaz-es |
| 458 | bim-meammebz-pheaz-es |
| 459 | bim-meapmebz-pheaz-es |
| 460 | bim-mepipe2-pheaz-es |
| 461 | bim-mepyma2-pheaz-es |
| 462 | bim-penta-8mephec-es |
| 463 | bim-penta-8mephec-gs |
| 464 | bim-penta-8mephec-ps |
| 465 | bim-penta-deophec-es |
| 466 | bim-penta-deophec-gs |
| 467 | bim-penta-deophec-ps |
| 468 | bim-penta-pheaz-es |
| 469 | bim-penta-pheaz-ps |
| 470 | bim-penta-phec-es |
| 471 | bim-penta-phec-gs |
| 472 | bim-penta-phec-ps |
| 473 | bim-penta-thioph-es |
| 474 | bim-penta-thioph-gs |
| 475 | bim-penta-thioph-ps |
| 476 | bim-pipa2-pheaz-es |
| 477 | bim-pipeme2-pheaz-es |
| 478 | bim-pyma2-pheaz-es |
| 479 | dhim-am2-pheac-es |
| 480 | dhim-dibema2-phec-gs |
| 481 | dhim-edia2-phec-es |
| 482 | dhpyrr-am2-pheac-es |
| 483 | dhpyrr-dibema2-phec-gs |
| 484 | dhpyrr-edia2-phec-es |
| 485 | dhthi-am2-pheac-es |
| 486 | dhthi-dibema2-phec-gs |
| 487 | dhthi-edia2-phec-es |
| 488 | dimethpym-am2-pheac-es |
| 489 | dimethpym-dibema2-phec-gs |
| 490 | dimethpym-edia2-phec-es |
| 491 | gua-am2-pheac-es |
| 492 | gua-dibema2-phec-gs |
| 493 | gua-edia2-phec-es |
| 494 | hs-am2-pheac-es |
| 495 | hs-dibema2-phec-gs |
| 496 | hs-edia2-phec-es |
| 497 | hts-am2-pheac-es |
| 498 | hts-dibema2-phec-gs |
| 499 | hts-edia2-phec-es |
| 500 | hyd-am2-pheac-es |
| 501 | hyd-dibema2-phec-gs |
| 502 | hyd-edia2-phec-es |
| 503 | ibhs-am2-pheac-es |
| 504 | ibhs-dibema2-phec-gs |
| 505 | ibhs-edia2-phec-es |
| 506 | im-am2-pheac-es |
| 507 | im-dibema2-phec-gs |
| 508 | im-edia2-phec-es |
| 509 | imhs-am2-pheac-es |
| 510 | imhs-dibema2-phec-gs |
| 511 | imhs-edia2-phec-es |
| 512 | impy-am2-8mephec-es |
| 513 | impy-am2-8mephec-gs |
| 514 | impy-am2-8mephec-ps |
| 515 | impy-am2-deophec-es |
| 516 | impy-am2-deophec-gs |
| 517 | impy-am2-deophec-ps |
| 518 | impy-am2-pheaz-es |
| 519 | impy-am2-pheaz-ps |
| 520 | impy-am2-phec-es |

-continued

| Compound | Structural elements A-E-G-L |
|---|---|
| 521 | impy-am2-phec-gs |
| 522 | impy-am2-phec-ps |
| 523 | impy-am2-thioph-es |
| 524 | impy-am2-thioph-gs |
| 525 | impy-am2-thioph-ps |
| 526 | impy-dibema2-8mephec-es |
| 527 | impy-dibema2-8mephec-gs |
| 528 | impy-dibema2-8mephec-ps |
| 529 | impy-dibema2-deophec-es |
| 530 | impy-dibema2-deophec-gs |
| 531 | impy-dibema2-deophec-ps |
| 532 | impy-dibema2-pheaz-es |
| 533 | impy-dibema2-pheaz-ps |
| 534 | impy-dibema2-phec-es |
| 535 | impy-dibema2-phec-gs |
| 536 | impy-dibema2-phec-ps |
| 537 | impy-dibema2-thioph-es |
| 538 | impy-dibema2-thioph-gs |
| 539 | impy-dibema2-thioph-ps |
| 540 | impy-edia2-8mephec-es |
| 541 | impy-edia2-8mephec-gs |
| 542 | impy-edia2-8mephec-ps |
| 543 | impy-edia2-deophec-es |
| 544 | impy-edia2-deophec-gs |
| 545 | impy-edia2-deophec-ps |
| 546 | impy-edia2-pheaz-es |
| 547 | impy-edia2-pheaz-ps |
| 548 | impy-edia2-phec-es |
| 549 | impy-edia2-phec-gs |
| 550 | impy-edia2-phec-ps |
| 551 | impy-edia2-thioph-es |
| 552 | impy-edia2-thioph-gs |
| 553 | impy-edia2-thioph-ps |
| 554 | impy-penta-8mephec-es |
| 555 | impy-penta-8mephec-gs |
| 556 | impy-penta-8mephec-ps |
| 557 | impy-penta-deophec-es |
| 558 | impy-penta-deophec-gs |
| 559 | impy-penta-deophec-ps |
| 560 | impy-penta-pheaz-es |
| 561 | impy-penta-pheaz-ps |
| 562 | impy-penta-phec-es |
| 563 | impy-penta-phec-gs |
| 564 | impy-penta-phec-ps |
| 565 | impy-penta-thioph-es |
| 566 | impy-penta-thioph-gs |
| 567 | impy-penta-thioph-ps |
| 568 | mam2py-am2-pheac-es |
| 569 | mam2py-dibema2-phec-gs |
| 570 | mam2py-edia2-phec-es |
| 571 | nmhs-am2-pheac-es |
| 572 | nmhs-dibema2-phec-gs |
| 573 | nmhs-edia2-pheces |
| 574 | pippy-am2-pheac-es |
| 575 | pippy-am2-phec-es |
| 576 | pippy-am2-phec-gs |
| 577 | piraz-am2-pheac-es |
| 578 | piraz-am2-phec-es |
| 579 | piraz-am2-phec-gs |
| 580 | ppy-am2-pheac-es |
| 581 | ppy-dibema2-phec-gs |
| 582 | ppy-edia2-phec-es |
| 583 | sabhs-am2-pheac-es |
| 584 | sabhs-dibema2-phec-gs |
| 585 | sabhs-edia2-phec-es |
| 586 | thazep-am2-pheac-es |
| 587 | thazep-dibema2-phec-gs |
| 588 | thazep-edia2-phec-es |
| 589 | thiz-am2-pheac-es |
| 590 | thiz-dibema2-phec-gs |
| 591 | thiz-edia2-phec-es |
| 592 | thpy-am2-pheac-es |
| 593 | thpy-dibema2-phec-gs |
| 594 | thpy-edia2-phec-es |
| 595 | thpym-am2-pheac-es |
| 596 | thpym-dibema2-phec-gs |
| 597 | thpym-edia2-phec-es |

-continued

| Compound | Structural elements A-E-G-L |
|---|---|
| 598 | ur-am2-pheac-es |
| 599 | ur-dibema2-phec-gs |
| 600 | ur-edia2-phec-es |

In the right-hand column of the above table, each line represents a compound. The abbreviations in the right-hand column in each case represent, separated by a hyphen, a structural element A, E, G and L, where the abbreviations have the following meanings:

| A = | Abbreviation |
|---|---|
| 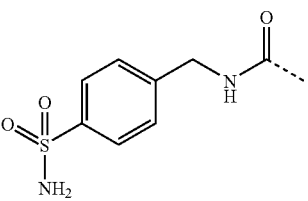 | 2py |
| 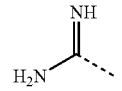 | thpym |
| 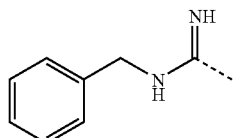 | dhim |
| 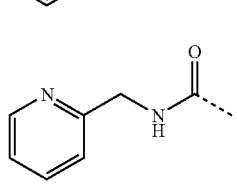 | nmhs |
|  | bim |
| 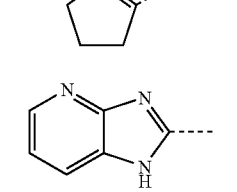 | 4pmhs |
| 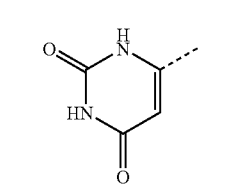 | imhs |
| 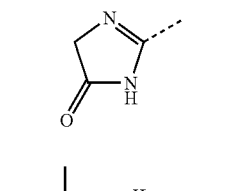 | hs |
| 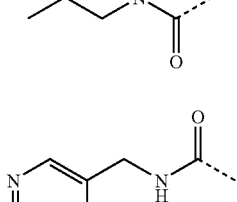 | bhs |

-continued

| A = | Abbreviation |
|---|---|
| 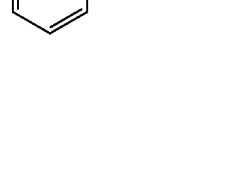 | sabhs |
| | gua |
| | bgua |
| | 2pmhs |
| | dhpyrr |
| | impy |
| | ur |
| | hyd |
| | ibhs |
| | 3pmhs |

-continued

| A = | Abbreviation |
|---|---|
| (structure) | agua |
| (structure) | dhthi |
| (structure) | dimethpym |
| (structure) | thazep |
| (structure) | hts |
| (structure) | mam2py |
| (structure) | ppy |
| (structure) | thpy |
| (structure) | im |
| (structure) | am2py |
| (structure) | amthiz |
| (structure) | pippy |

-continued

| A = | Abbreviation |
|---|---|
| (structure) | am4py |
| (structure) | amim |
| (structure) | piraz |
| (structure) | thiz |
| (structure) | amhyd |
| (structure) | amtriz |

| E = | Abbreviation |
|---|---|
| (structure) | edia2 |
| (structure) | mepipe2 |
| (structure) | pyma2 |
| (structure) | am2 |
| (structure) | pipa2 |

-continued
| E = | Abbreviation |
|---|---|
| 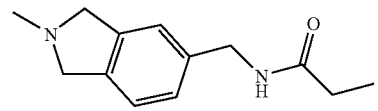 | inda2 |
| 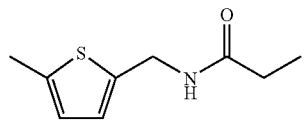 | 25thima2 |
| 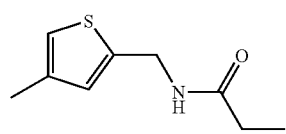 | 35thima2 |
| 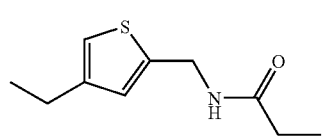 | me35thima2 |
| 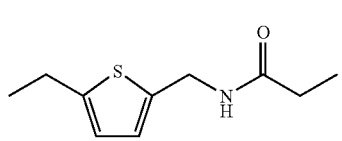 | me25thima2 |
| 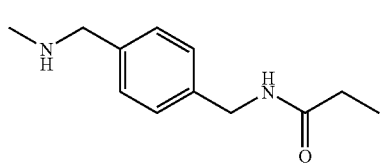 | dibema2 |
| 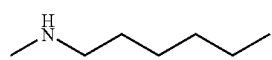 | penta |
| 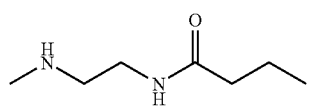 | edia3 |
| 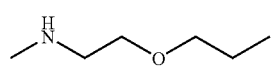 | aof |
| 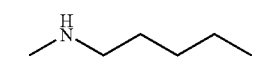 | buta |
| 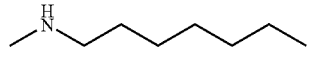 | hexa |
| 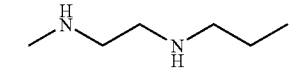 | aaf |
| 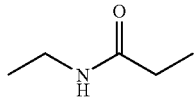 | mea2 |
-continued
| E = | Abbreviation |
|---|---|
| 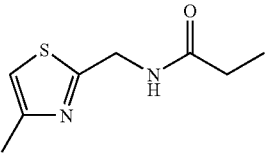 | 42thiaz2 |
| 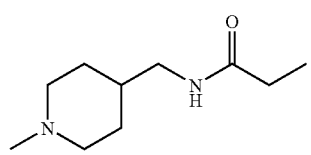 | pipeme2 |
| 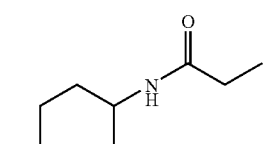 | chex2 |
| 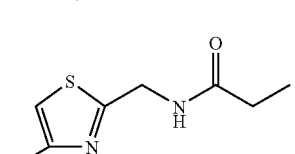 | me42thiaz2 |
| 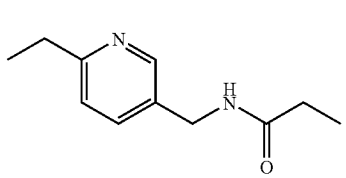 | mepyma2 |
| 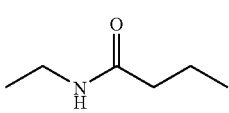 | mea3 |
| 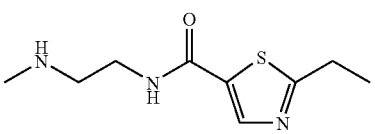 | edia42thiaz |
| 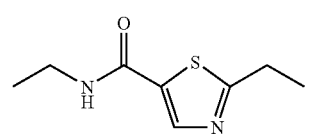 | mea42thiaz |
| 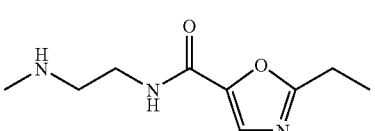 | edia42oxaz |
| 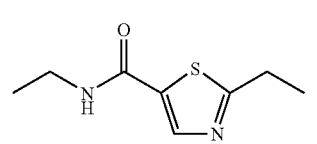 | mea42oxaz |

| E = | Abbreviation | G = | Abbreviation |
|---|---|---|---|
| 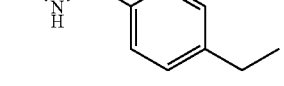 | ediapmebz | 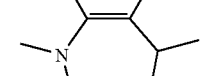 | 2mephec |
| 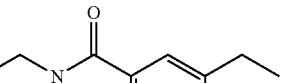 | ediammebz | 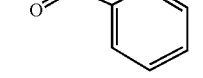 | 8mephec |
| 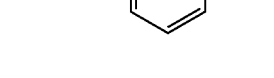 | meapmebz | | |
| 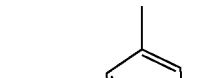 | meammebz |  | meophe |
| 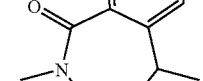 | edia26pyme | | |
|  | edia36pyme | 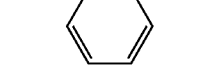 | 23dimephec |
| 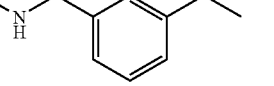 | mea26pyme | 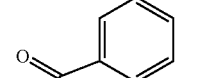 | 9clphec |
| 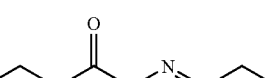 | mea36pyme | | |

-continued
| G = | Abbreviation |
|---|---|
| 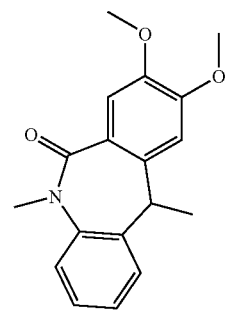 | 78dimeophec |
| 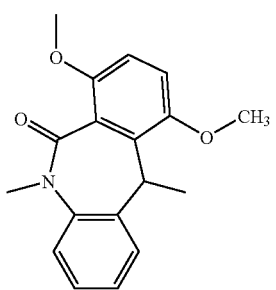 | 69dimeophec |
| 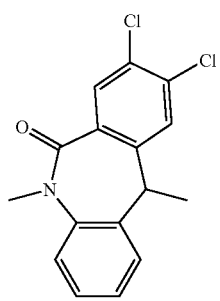 | 78diclphec |
| 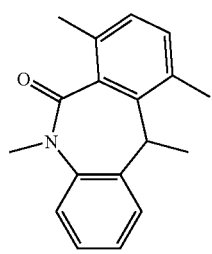 | 69dimephec |
| 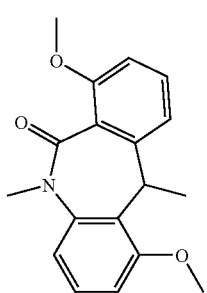 | 49dimeophec |
-continued
| G = | Abbreviation |
|---|---|
| 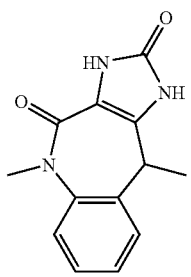 | imon |
| 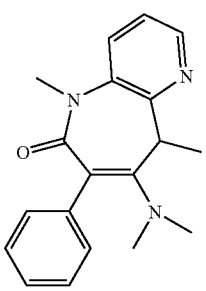 | dimepy |
| 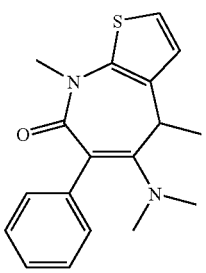 | dimethio |
| 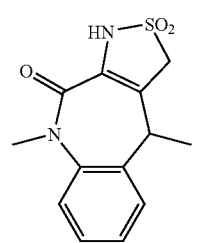 | sulfo |
| 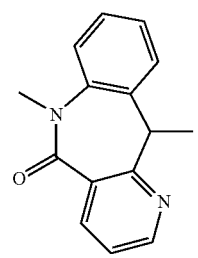 | pyphc |
| 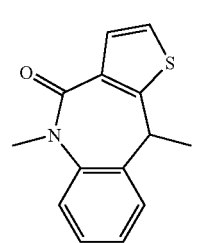 | thioph |

-continued

| G = | Abbreviation |
|---|---|
| | pheaz |
| | thiomet |
| | phepyra |
| | benz |
| | phec |

-continued

| G = | Abbreviation |
|---|---|
| | dimepyaz |
| | 8mepyaz |
| | meoaz |
| | phedb |
| | 5claz |

-continued

| G = | Abbreviation |
|---|---|
| (structure) | thiophaz |
| (structure) | mephe |
| (structure) | cl2phec |
| (structure) | 27dimeophec |
| (structure) | deophec |
| (structure) | thioph2 |

-continued

| G = | Abbreviation |
|---|---|
| (structure) | deothioph |
| (structure) | dmaphec |

| L = | Abbreviation |
|---|---|
| (structure) | es |
| (structure) | ps |
| (structure) | gs |
| (structure) | ms |
| (structure) | pms |
| (structure) | nes |

-continued

| L = | Abbreviation |
|---|---|
| 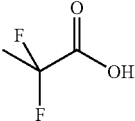 | f2es |
| 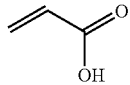 | as |
| 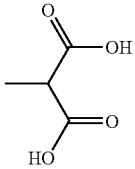 | mals |

Compounds of the general formula I and the starting materials used to prepare them can generally be prepared by methods of organic chemistry known to the skilled worker as described in standard works such as, for example, Houben-Weyl, "Methoden der Organischen Chemie", Thieme-Verlag, Stuttgart, or March "Advanced Organic Chemistry", 4th Edition, Wiley & Sons. Further preparation methods are also described in R. Larock, "Comprehensive organic Transformations", weinheim 1989, in particular the preparation of alkenes, alkynes, halides, amines, ethers, alcohols, phenols, aldehydes, ketones, nitriles, carboxylic acids, esters, amides and acid chlorides.

The general synthesis of compounds of the formula I where A—E— represents B is described in schemes 1–7. Unless otherwise indicated, all the starting materials and reagents can be bought or can be prepared by conventional methods from precursors which can be bought.

Scheme 1 describes the synthesis of compounds of the formula I in general.

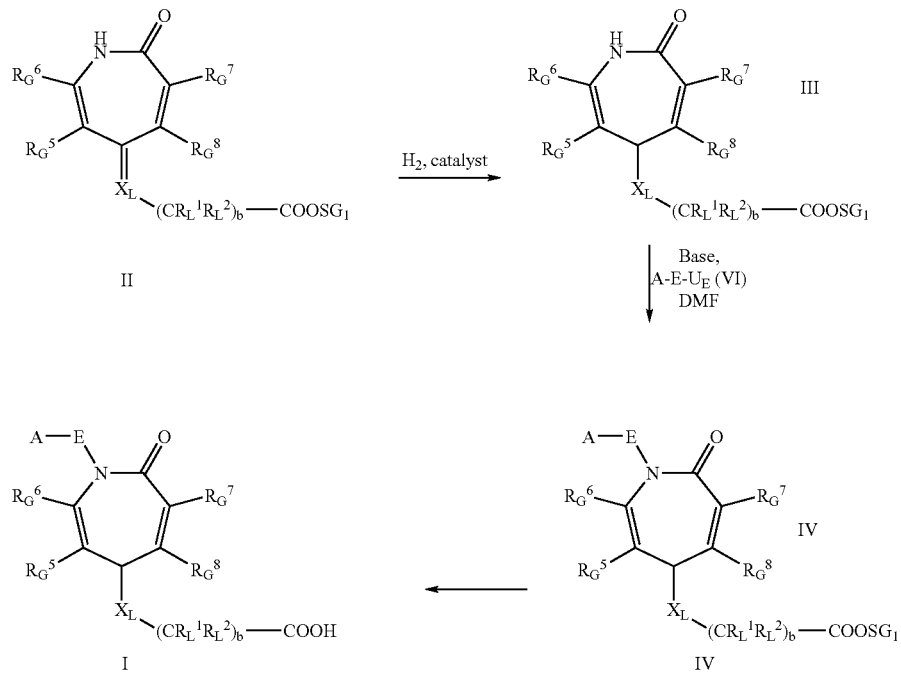

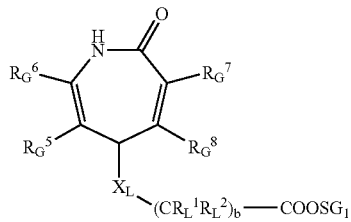 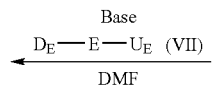 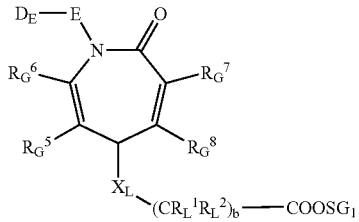

III    V

Building blocks of type II (for $X_L$ equal to CH) are known and can be prepared by known methods starting from appropriately substituted or fused 1H-azepine-2,5-diones as described by way of example e.g. in J. Med. Chem. 1986, 29, 1877–1888 or DE 1568217. 1H-Azepine-2,5-diones used to prepare compounds of type I can either be bought or be prepared as described in the following publications:

5H-Dibenzo[b,e]azepine-6,11-dione and substituted variants according to J. Med. Chem. 1965, 8, 74 or Gazz. Chim. Ital. 1953, 83, 533 and 1954, 84, 1135;

5H-pyrido[3,2-c][1]benzazepine-5,11(6H)-dione according to Liebigs Ann. Chem. 1989, 469–476;

4H-thieno[3,2-c][1]benzazepine-4,10 (5H)-dione according to Eur. J. Med. Chem. Ther. 1981, 16, 391–398.

The conversion to III is carried out by hydrogenating the double bond under standard conditions. It is also possible for this to make use of variants which are known per se but which are not mentioned here. The hydrogenation is preferably carried out in the presence of a noble metal catalyst such as, for example, Pd on active carbon, Pt, $PtO_2$, Rh on $Al_2O_3$ in an inert solvent at a temperature of 0–150° C. under a pressure of 1–200 bar; addition of an acid such as, for example, acetic acid or hydrochloric acid may be advantageous. Hydrogenation in the presence of 5–10% Pd on active carbon is particularly preferred.

Solvents which can be used are all conventional inert solvents such as, for example, hydrocarbons such as hexane, heptane, petroleum ether, toluene, benzene or xylene; chlorinated hydrocarbons such as trichloroethylene, 1,2-dichloroethane, carbon tetrachloride, chloroform, dichloromethane; alcohols such as methanol, ethanol, isopropanol, n-propanol, n-butanol or tert-butanol; ethers such as diethyl ether, methyl tert-butyl ether, diisopropyl ether, tetrahydrofuran, dioxane; glycol ethers such as ethylene glycol monomethyl ether or monoethyl ether, ethylene glycol dimethyl ether; ketones such as acetone, butanone; amides such as dimethylformamide (DMF), dimethylacetamide or acetamide; sulfoxides such as dimethyl sulfoxide, sulfolane; pyridine, N-methylpyrrolidone, 1,3-dimethyltetrahydro-2 (1H)-pyrimidinone (DMPU), 1,3-dimethyl-2-imidazolidinone, water or mixtures of said solvents.

Compounds of type IV are prepared by reaction with compounds of the general formula A—E—$U_E$ (VI), where the $U_E$ radical is a conventional leaving group, for example halogen such as chlorine, bromine, iodine or an optionally halogen-, alkyl- or haloalkyl-substituted aryl- or alkylsulfonyloxy radical such as, for example, toluenesulfonyloxy, trifluoromethanesulfonyloxy and methylsulfonyloxy or another equivalent leaving group.

The reaction preferably takes place in an inert solvent with the addition of a suitable base, i.e. a base which deprotonates the intermediate III, at a temperature in the range from –40° C. to the boiling point of the appropriate solvent.

The base which can be used is an alkali metal or alkaline earth metal hydride such as sodium hydride, potassium hydride or calcium hydride, a carbonate such as alkali metal carbonate, for example sodium or potassium carbonate, an alkali metal or alkaline earth metal hydroxide such as sodium or potassium hydroxide, an alcoholate such as, for example, sodium methanolate, potassium tert-butanolate, an organometallic compound such as butyllithium or alkali metal amides such as lithium diisopropylamide, lithium, sodium or potassium bis(trimethylsilyl)amide.

Elimination of the protective group SG1 under standard conditions (see below) results in the compounds of the general formula I. Where SG1 is equal to $C_1$–$C_4$-alkyl or benzyl, the compounds of the general formula IV correspond directly to the compounds of type I.

As an alternative to this synthetic strategy, compounds of type I can also be prepared via V as intermediate, in which case the reaction conditions used are those known to the skilled worker and described in standard works. Compound V is prepared by reacting compounds of type III with compounds of the general formula $D_E$—E—$U_E$ (VII) under the reaction conditions already described for preparing IV. $U_E$ is a suitable leaving group as described above, and DE is CN or a protected amino or acid function of the general formula $NSG_3$ or $COOSG_2$. The fragments $D_E$—E and A—E are synthesized—depending on the actual structure of E— by eliminating the protective groups and coupling on the remaining fragments by standard methods, for example amide coupling. The introduction of A then takes place in analogy to the reactions described in schemes 3–7.

Compounds of type I in which $X_G$ is N can be prepared as shown in scheme 2.

Scheme 2

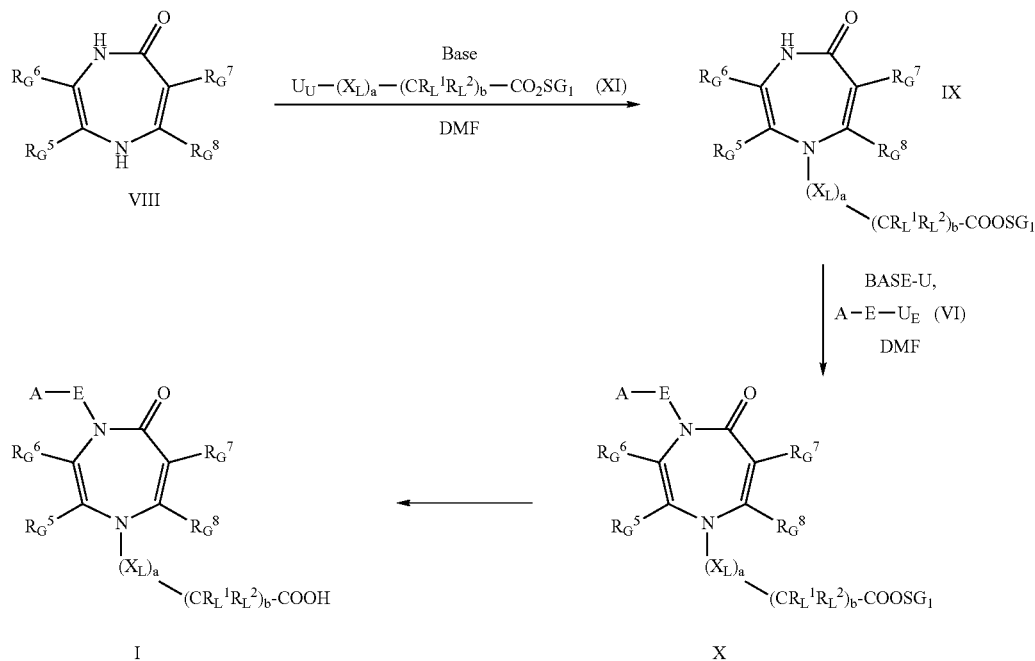

The synthesis starts from compounds of type VIII which are either known or accessible to the skilled worker by known methods as described, for example, in Pharmazie 45 (8), 1990, 555–559. Alkylation with a compound of the general formula XI ($U_U$=conventional leaving group as described above for $U_E$) under the reaction conditions described for preparing substances of type IV results in IX. The subsequent reactions to I via X take place in analogy to Scheme 1.

The coupling of the individual fragments and the elimination of the protective groups can take place by known processes (see Larock, "Comprehensive organic Transformations"; protective groups: Greene and Wuts, T., "Protective Groups in Organic Synthesis", New York 1991), and in the case of amide linkages also analogously to the methods of peptide synthesis as described in standard works, for example in Bodanszky "The Practice of Peptide Synthesis", 2nd Edition, Springer-Verlag 1994, and Bodanszky "Principles of Peptide Synthesis", Springer-Verlag 1984. A general review of the conventional methods for peptide synthesis and a listing of suitable reagents can moreover be found in NOVABIOCHEM 1999 "Catalog and Peptide Synthesis Handbook".

Said amide couplings can be carried out with the aid of conventional coupling reagents using suitably protected amino and carboxylic acid derivatives. Another method comprises the use of preactivated carboxylic acid derivatives, preferably of carbonyl halides, symmetrical or mixed anhydrides or so-called active esters, which are normally used to acylate amines. These activated carboxylic acid derivatives can also be prepared in situ. The couplings can usually be carried out in inert solvents in the presence of an acid-binding agent, preferably an organic base such as, for example, triethylamine, pyridine, diisopropylethylamine, N-methylmorpholine, quinoline; it may also be beneficial to add an alkali metal or alkaline earth metal hydroxide, carbonate or bicarbonate or another weak acid salt of the alkali metals or alkaline earth metals, preferably of potassium, sodium, calcium or cesium.

The reaction time is between minutes and 14 days, and the reaction temperature is between –40° C. and 140° C., preferably between –20° C. and 100° C., depending on the conditions used.

Examples of suitable inert solvents are hydrocarbons such as hexane, heptane, petroleum ether, toluene, benzene or xylene; chlorinated hydrocarbons such as trichloroethylene, 1,2-dichloroethane, tetrachloromethane, chloroform, dichloromethane; alcohols such as methanol, ethanol, isopropanol, n-propanol, n-butanol or tert-butanol; ethers such as diethyl ether, methyl tert-butyl ether, diisopropyl ether, tetrahydrofuran, dioxane; glycol ethers such as ethylene glycol monomethyl ether or monoethyl ether, ethylene glycol dimethyl ether; ketones such as acetone, butanone; amides such as dimethylformamide (DMF), dimethylacetamide or acetamide; nitriles such as acetonitrile; sulfoxides such as dimethyl sulfoxide, sulfolane; N-methylpyrrolidone, 1,3-dimethyltetrahydro-2 (1H)-pyrimidinone (DMPU), 1,3-dimethyl-2-imidazolidinone, nitro compounds such as nitromethane or nitrobenzene; esters such as ethyl acetate; water; or mixtures of said solvents.

The protective groups SG which can be used are all conventional protective groups known to the skilled worker from peptide synthesis, as are also described in the above-mentioned standard works.

Elimination of the protective groups in the compounds of the formula IV, V, VI and VII likewise takes place under conditions known to the skilled worker and described, for example, by Greene and Wuts in "Protective Groups in Organic Synthesis", 2nd Edition, Wiley & Sons, 1991.

Protective groups such as $SG_3$ are so-called N-terminal amino protective groups; those preferred for this are Boc, Fmoc, benzyloxycarbonyl (Z), acetyl or Mtr.

SG$_1$ and SG$_2$ are so-called C-terminal hydroxyl protective groups, and these are preferably C$_1$–C$_4$-alkyl such as, for example, methyl, ethyl, tert-butyl or else benzyl or trityl, or else polymer-bound protective groups in the form of the commercially available polystyrene resins such as, for example, 2-chlorotrityl chloride-resin or Wang resin (supplied by Bachem, Novabiochem).

Acid-labile protective groups (for example Boc, tert-butyl, Mtr, trityl) can be eliminated—depending on the protective group used—with organic acids such as trifluoroacetic acid (TFA), trichloroacetic acid, perchloric acid, trifluoroethanol; but also inorganic acids such as hydrochloric acid or sulfuric acid, sulfonic acids such as benzene- or p-toluenesulfonic acid, with the acids generally being employed in excess. In the case of trityl it may be advantageous to add thiols such as, for example, thioanisole or thiophenol. The presence of an additional inert solvent is possible but not always necessary. Suitable and preferred inert solvents are organic solvents, for example carboxylic acids such as acetic acid; ethers such as THF or dioxane; amides such as DMF or dimethylacetamide; halogenated hydrocarbons such as dichloromethane; alcohols such as methanol, isopropanol; or water. Mixtures of said solvents are also suitable.

The temperature for these reactions is between 10° C. and 50° C., preferably in the range between 0° C. and 30° C.

Base-labile protective groups such as fmoc are cleaved by treatment with organic amines such as dimethylamine, diethylamine, morpholine, piperidine as 5–50% solutions in CH$_2$Cl$_2$ or DMF. The temperature for these reactions is between 10° C. and 50° C., preferably in the range between 0° C. and 30° C.

Acid-protective groups such as methyl or ethyl are preferably cleaved by basic hydrolysis in an inert solvent. The bases preferably used are alkali metal or alkaline earth metal hydroxides, preferably NaOH, KOH or LiOH;

the solvents used are all conventional inert solvents such as, for example, hydrocarbons such as hexane, heptane, petroleum ether, toluene, benzene or xylene; chlorinated hydrocarbons such as trichloroethylene, 1,2-dichloroethane, tetrachloromethane, chloroform, dichloromethane; alcohols such as methanol, ethanol, isopropanol, n-propanol, n-butanol or tert-butanol; ethers such as diethyl ether, methyl tert-butyl ether, diisopropyl ether, tetrahydrofuran, dioxane; glycol ethers such as ethylene glycol monomethyl ether or monoethyl ether, ethylene glycol dimethyl ether; ketones such as acetone, butanone; amides such as dimethylformamide (DMF), dimethylacetamide or acetamide; nitriles such as acetonitrile; sulfoxides such as dimethyl sulfoxide, sulfolane; N-methylpyrrolidone, 1,3-dimethyltetrahydro-2 (1H)-pyrimidinone (DMPU), 1,3-dimethyl-2-imidazolidinone; nitro compounds such as nitromethane or nitrobenzene; water or mixtures of said solvents. Addition of a phase-transfer catalyst may be advantageous, depending on the solvent or mixture thereof used. The temperature for these reactions is generally between −10° C. and 100° C.

Protective groups which can be eliminated by hydrogenolysis, such as benzyloxycarbonyl (Z) or benzyl can be eliminated, for example, by hydrogenolysis in the presence of a catalyst (for example a noble metal catalyst on active carbon as support). Suitable solvents are those indicated above, in particular alcohols such as methanol, ethanol; amides such as DMF or dimethylacetamide; esters such as ethyl acetate. The hydrogenolysis is usually carried out under a pressure of from 1 to 200 bar and at temperatures between 0° C. and 100° C.; addition of an acid such as, for example, acetic acid or hydrochloric acid may be advantageous. 5 to 10% Pd on active carbon is preferably used as catalyst.

The synthesis of building blocks of type E generally takes place by methods known to the skilled worker; the building blocks used can either be bought or be obtained by methods known from the literature. The synthesis of some of these building blocks is described by way of example in the experimental section.

In the case where the fragments Q$_E$ and X$_E$ present in the compounds of type V and VI are a hetaryl radical, the radical E can be synthesized via compounds of type VI-VII starting from aminohetaryl carboxylic acids, aminohetaryl carboxylic esters or nitriles by described methods known to the skilled worker. A large number of preparation methods are described in detail in Houben-Weyls "Methoden der organischen Chemie" (Vol. E6: Furans, thiophenes, pyrroles, indoles, benzothiophenes, -furans, -pyrroles; Vol. E7: Quinolines, pyridines, Vol. E8: Isoxazoles, oxazoles, thiazoles, pyrazoles, imidazoles and benzo-fused representatives thereof, and oxadiazoles, thiadiazoles and triazoles; Vol. E9: Pyridazines, pyrimidines, triazines, azepines and the benzo-fused representatives thereof, and purines). The linkage of these fragments to E can also take place via the amino or acid function, depending on the structure of E, by methods known to the skilled worker.

Appropriate hetaryl derivatives can either be bought or be prepared in analogy to the following publications:

5-(Aminomethyl)-2-pyridinecarbonitrile according to WO 95/25426, 5-(Aminomethyl)-3-thiophenecarbonitrile according to WO 98/06741, 5-(Aminomethyl)-2-thiophenecarbonitrile in WO 95/23609, 2-(Aminomethyl)-1,3-thiazole-4-carbonitrile in analogy to WO 98/06741, 3-Oxo-5-isoindolinecarboxylic acid according to WO 97/37655, 3-Amino-2-pyrrolidone according to WO 98/44797, Spirocycles such as 8-(aminomethyl)-2-oxa-3-azaspiro[4,5]dec-3-en-4-yl acetate and 7-(aminomethyl)-2-oxa-3-azaspiro[4.4]non-3-en-4-yl acetate according to WO 97/33887,

[5-(2-Aminoalkyl)-4,5-dihydro-3-isoxazolyl]carboxylic acid and acetate, [3-(2-aminoalkyl)-4,5-dihydro-5-isoxazolyl]carboxylic acid and acetate according to WO 96/37492, 1-(3-Aminoalkyl)-1H-indazole-5-carboxylic acid according to WO 97/23480;

Ethyl 2-amino-1,3-thiazole-5-carboxylate in Kushner et al., J. Org. Chem. 1948, 13, 834ff;

Methyl 2-amino-4-pyridinecarboxylate in Podany et al., J. Org. Chem. 1986, 51, 2988–2994;

Methyl 5-amino-3-pyridinecarboxylate in Hawkins et al., J. Org. Chem. 1949, 14, 328–332;

Methyl 4-amino-2-pyrimidinecarboxylate in DE 2848912,

Methyl 6-amino-4-pyrimidinecarboxylate in Zh. Org. Khim. 1981, 17, 312–317;

Ethyl 5-amino-1,3-thiazole-2-carboxylate in Adams et al., J. Chem. Soc. 1956, 1870–1873;

Methyl 4-(aminomethyl)-2-thiophenecarboxylate in Peschke et al., Bioorg. Med. Chem. Lett. 1997, 7, 1969–1972;

2-Amino-1,3-oxazole-4-carboxylic acid in Foulis et al., J. Med. Chem. 1971, 14, 1075–1077;

Methyl 4-aminopyridine-2-carboxylate in Mostier et al., J. Org. Chem. 1955, 20, 283–285;

Methyl 2-aminopyrimidine-3-carboxylate in Liebigs Ann. Chem. 1965, 209–211;

5-Amino-1,3,4-thiadiazole-5-carboxylic acid in Liebigs Ann. Chem. 1963, 3;

5-Amino-1,3,4-triazole-5-carboxylic acid in U.S. Pat. No. 3,023,210;

4-Aminopyrrole-2-carboxylic acid in J. Med. Chem. 1983, 26, 1042;

1-Methyl-3-aminopyrazole-5-carboxylic acid in Acta Chem. Scand. 1990, 44, 74;

1-Methyl-5-aminopyrazole-3-carboxylic acid in Lee et al., J. Org. Chem. 1989, 54, 428.

Conversion of compounds of the general formula XI and XII

(XI)

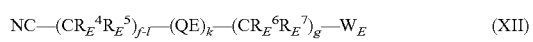

(XII)

into compounds of the general formula:

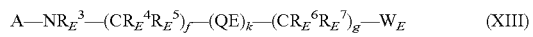

(XIII)

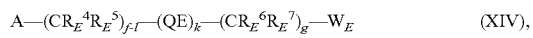

(XIV), where $W_E$ is $COOSG_2$ or $NSG_3$, can take place by methods known to the skilled worker and described, for example, in WO 97/08145. These building blocks can then be converted either directly—in the case of the corresponding free amines and carboxylic acids—or after elimination of the protective groups—into compounds of the general formula I (scheme 1).

However, it is also possible in principle for A to be introduced, as described in scheme 1, into compounds of type V, in which case the stated reaction conditions can be used, just as can variants not described here.

In schemes 3–7, a number of methods for introducing A are described by way of example, using in each case reaction conditions known and suitable for the particular reactions. It is moreover possible to make use of variants which are known per se but which are not mentioned here.

Scheme 3

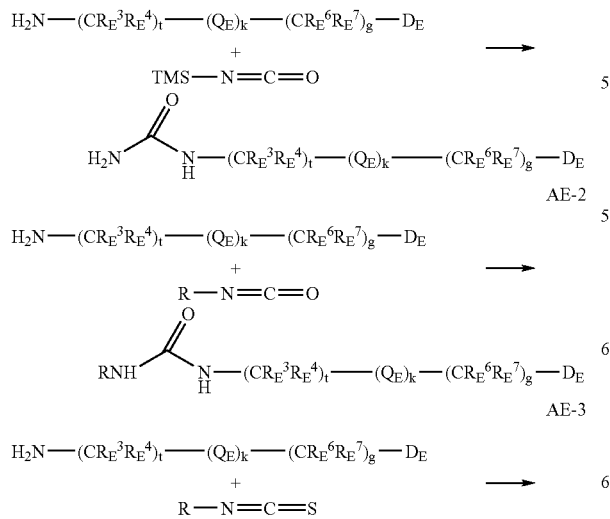

Ureas or thioureas (AE-1 to AE-3) can be prepared by conventional methods of organic chemistry, for example by reacting an isocyanate or an isothiocyanate with an amine, where appropriate in an inert solvent with heating (Houben-Weyl, Vol. VIII, 157 et seq.) (scheme 3).

Scheme 4 shows by way of example the preparation of compounds of type AE-4 as described, for example, by Blakemoore et al. in Eur. J. Med. Chem. 1987 (22) 2, 91–100, or by Misra et al. in Bioorg. Med. Chem. Lett. 1994, 4 (18), 2165–2170.

Scheme 4

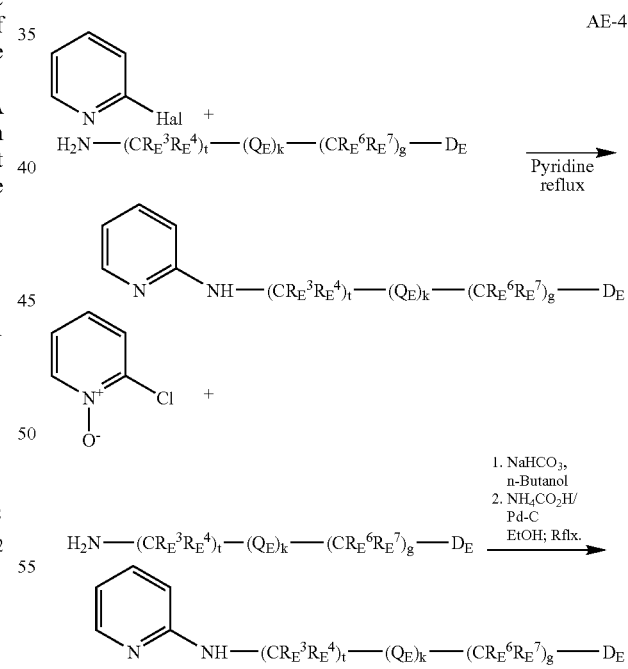

Unsubstituted or cyclic guanidine derivatives of the general formula AE-5 and AE-6 can be prepared using reagents which can be bought or obtained simply, as described, for example, in Synlett 1990, 745, J. Org. Chem. 1992, 57, 2497, Bioorg. Med. Chem. 1996, 6, 1185–1208; Bioorg. Med. Chem. 1998, 1185, or Synth. Comm. 1998, 28, 741–746.

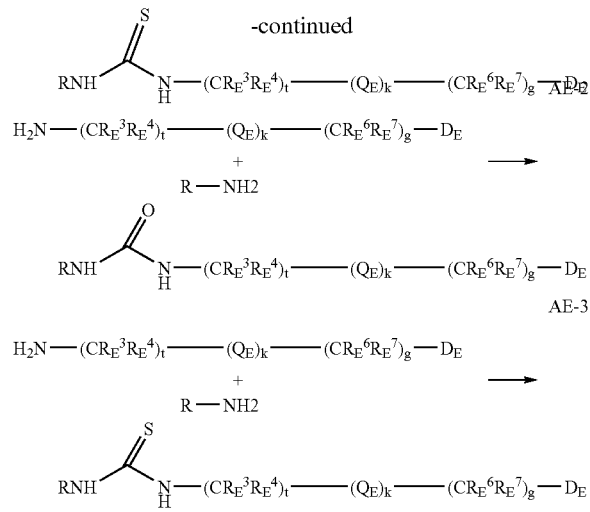

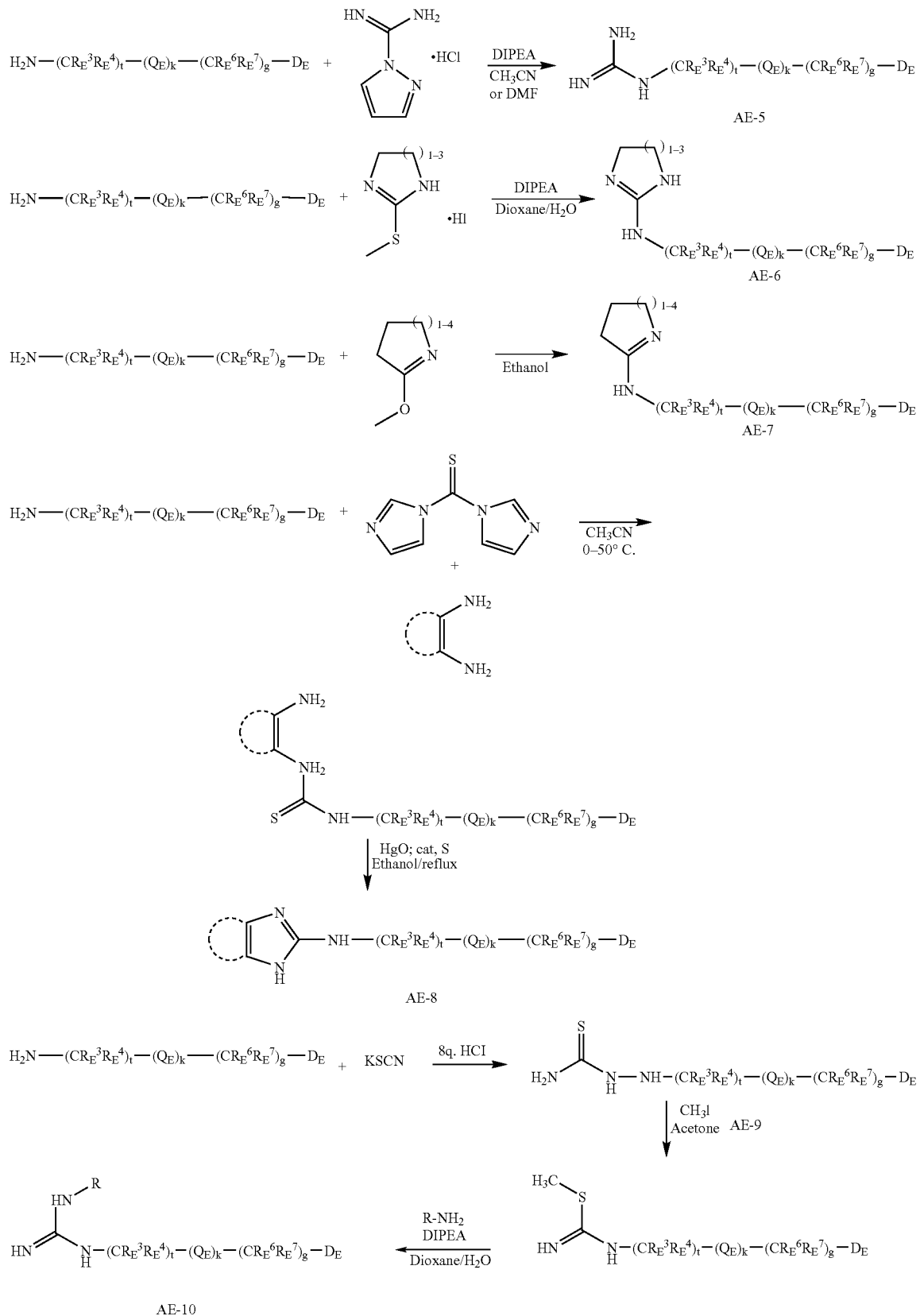

-continued

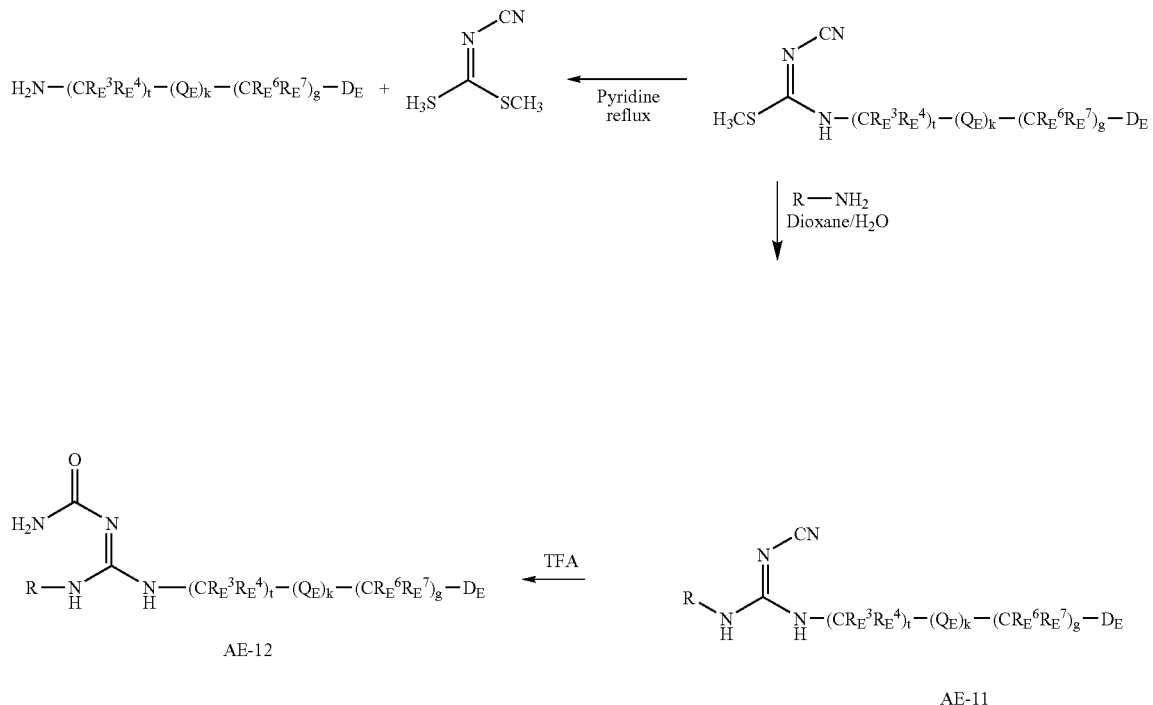

AE-12

AE-11

Preparation of compounds of the general formula AE-7 can take place in analogy to U.S. Pat. No. 3,202,660, and compounds of the formula AE-9, AE-10, AE-11 and AE-12 in analogy to WO 97/08145. Compounds of the formula AE-8 can be prepared, as shown in Scheme 6, for example by the methods described by Perkins et al., Tetrahedron Lett. 1999, 40, 1103–1106. Scheme 6 summarizes the synthesis of said compounds:

Scheme 6

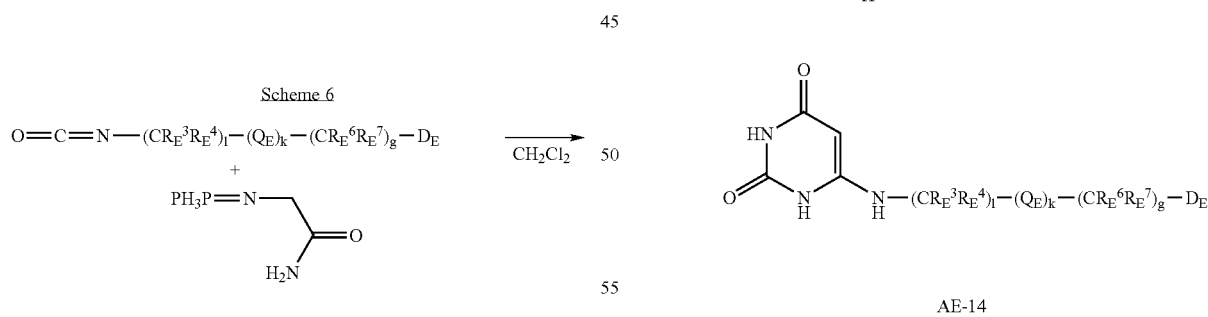

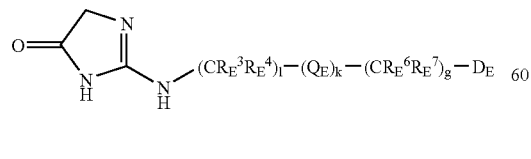

AE-13

-continued

AE-14

Compounds of the general formula AE-13 can be prepared in analogy to Froeyen et al., Phosphorus Sulfur Silicon Relat. Elem. 1991, 63, 283–293, AE-14 in analogy to Yoneda et al., Heterocycles 1998, 15 N°-1, Spec. Issue, 341–344 (scheme 7). The preparation of corresponding compounds can also take place in analogy to WO 97/36859.

Compounds of the general formula AE-15 can be prepared as in Synthesis 1981, 963–965 or Synth. Comm. 1997, 27 (15), 2701–2707, AE-16 in analogy to J. Org. Chem. 1991, 56 (6), 2260–2262 (scheme 7).

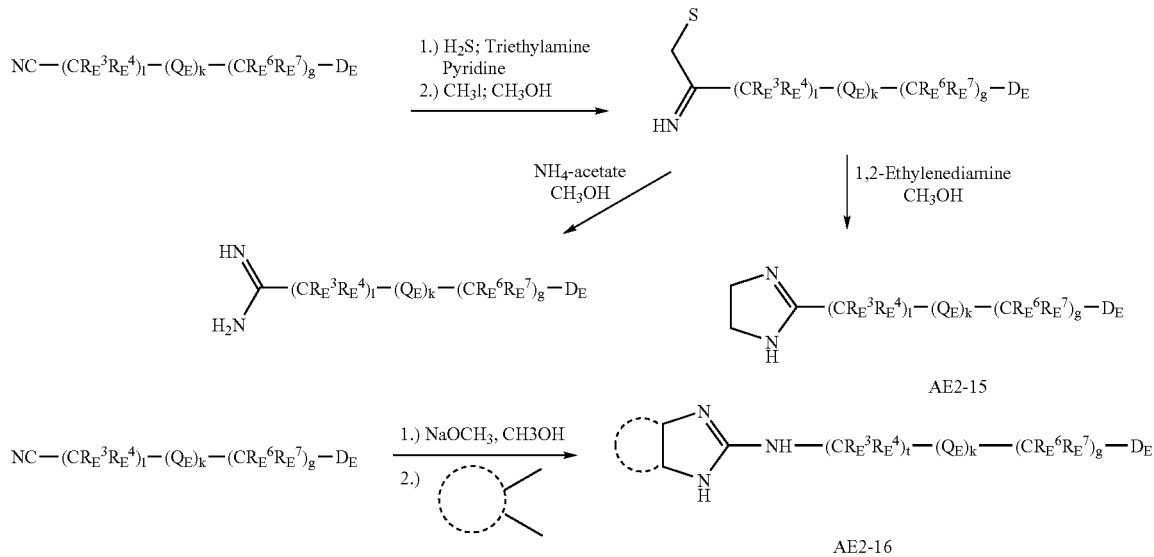

Scheme 7

The invention further relates to the use of the structural element of the formula $I_{GL}$ $$—G—L \qquad I_{GL}$$

for preparing compounds which bind to integrin receptors.

The invention further relates to drugs comprising the structural element of the formula $I_{GL}$.

The invention further relates to pharmaceutical preparations for oral and parenteral use containing at least one compound of the formula I in addition to conventional pharmaceutical excipients.

The compounds according to the invention can be administered orally or parenterally (subcutaneously, intravenously, intramuscularly, intraperitoneally) in a conventional way. Administration can also take place with vapors or sprays through the nasopharyngeal space.

The dosage depends on the age, condition and weight of the patient and on the mode of administration. As a rule, the daily dose of active ingredient is between about 0.5 and 50 mg/kg of body weight on oral administration and between about 0.1 and 10 mg/kg of body weight on parenteral administration.

The novel compounds can be used in conventional solid or liquid pharmaceutical forms, for example as uncoated or (film-)coated tablets, capsules, powders, granules, suppositories, solutions, ointments, creams or sprays. These are produced in a conventional way. The active ingredients can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The administration forms obtained in this way normally contain from 0.1 to 90% by weight of active ingredient.

The invention further relates to the use of the compounds of the formula I for producing drugs for the treatment of diseases. The compounds of the formula I can be used for treating human and animal diseases. The compounds of the formula I bind to integrin receptors. They are therefore suitable preferably as integrin receptor ligands and for producing drugs for treating diseases in which an integrin receptor is involved.

They can preferably be used to produce drugs for treating diseases in which, for example, there is excessive interaction between integrins and their natural ligands.

The compounds of the formula I preferentially bind to the $\alpha_v\beta_3$ integrin receptor and can thus be used particularly preferably as ligands of the $\alpha_v\beta_3$ integrin receptor and for treating diseases in which the $\alpha_v\beta_3$ integrin receptor is involved.

They can preferably be used to produce drugs for treating diseases in which, for example, there is excessive interaction between the $\alpha_v\beta_3$ integrin receptor and its natural ligands.

The compounds of the formula I are preferably used for influencing metabolic processes or regulatory mechanisms underlying particular diseases, such as, for example, inhibition of angiogenesis or for treating the following diseases:

cardiovascular diseases such as atherosclerosis, restenosis after vessel injury, and angioplasty (neointima formation, smooth muscle cell migration and proliferation), acute kidney failure, angiogenesis-associated microangiopathies such as, for example, diabetic retinopathy or rheumatoid arthritis, blood platelet-mediated vascular occlusion, arterial thrombosis, stroke, reperfusion damage after myocardial infarct or stroke, cancers such as, for example, in tumor metastasis or tumor growth (tumor-induced angiogenesis), osteoporosis (bone resorption after proliferation, chemotaxis and adhesion of osteoclasts to bone matrix), high blood pressure, psoriasis, hyperparathyroidism, Paget's disease, malignant hypercalcemia, metastatic osteolytic lesions, inflammation, wound healing, cardiac insufficiency, CHF, and for antiviral, antiparasitic or antibacterial therapy and prophylaxis (adhesion and internalization).

The following examples illustrate the invention but the selection of these examples is non-limiting.

I. SYNTHETIC EXAMPLES

I.A Precursors

Preparation of the Building Blocks

Methyl (E,Z)-[5-(2-tert-butoxy-2-oxoethyl)-6-oxo-5,6-dihydro-11H-dibenzo[b,e]azepin-11-ylidene]acetate (1)

A solution of methyl (E,Z)-(6-oxo-5,6-dihydro-11H-dibenzo[b,e])-azepin-11-ylidene)acetate (27 g, 96.7 mmol) in 100 ml of DMF was added dropwise to a suspension of 4.7 g of NaH (60%; oil removed with n-pentane) in 400 ml of DMF at 0° C. and stirred for about min for complete formation of the anion. Then tert-butyl bromoacetate (18.9 g, 96.7 mmol) was added and the mixture was stirred at 0° C. for about 1.5 h. For workup, aqueous $NH_4Cl$ solution was added to the mixture and, after concentration, the residue was taken up in $CH_2Cl_2$ and washed with saturated NaCl solution. Drying and concentration of the $CH_2Cl_2$ phase afforded 40.5 g of solid which was then stirred with pentane and dried at 30° C. in vacuo.

31.6 g; ESI-MS [M−tBu+H$^+$]=338;
$^1$H-NMR (DMSO-d6, 200 MHz) E/Z mixture: δ (ppm) 7.65–7.1 (m, 8H), 6.3/6.25 (s, 1H), 4.5 (m, 2H), 3.6 (s, 3H), 1.35 (s, 9H).

Methyl [5-(2-tert-butoxy-2-oxoethyl)-6-oxo-6,11-dihydro-5-H-dibenzo-[b,e]azepin-11-yl]acetate (2)

Methyl (E,Z)-[5-(2-tert-butoxy-2-oxoethyl)-6-oxo-5,6-dihydro-11-H-dibenzo[b,e]azepin-11-ylidene]acetate 1 (41 g, 104.2 mmol) was taken up in 1 l of 1:1 $CH_3OH$/ethyl acetate and, after addition of 3.1 g of catalyst (10% Pd on carbon), the mixture was hydrogenated at 50° C. under a pressure of 120 bar for 21 h. Filtration through Celite, washing with $CH_3OH$ and evaporation of the combined phases afforded 41.1 g of the hydrogenation product as a white foam.

ESI-MS [M−tBu+H$^+$]=340.05;
$^1$H-NMR (DMSO-d6, 270 MHz) diastereomer mixture: δ (ppm) 7.70–7.1 (m, 8H), 4.8–4.6 (m, 3H), 3.65/3.35 (s, 3H), 3.05 (m, 2H), 1.5/1.45 (s, 9H).

11-(2-Methoxy-2-oxoethyl)-6-oxo-6,11-dihydro-5H-dibenzo[b,e]-azepin-5-yl acetate (3)

Methyl [5-(2-tert-butoxy-2-oxoethyl)-6-oxo-6,11-dihydro-5H-dibenzo[b,e]azepin-11-yl]acetate 2 (30.5 g, 77.5 mmol) was taken up in 100 ml of $CH_2Cl_2$ and, at 0° C., 150 ml of TFA were added, and the mixture was stirred at 0° C. for about 1 h and then at RT. After the reaction was complete, the mixture was evaporated, and mixed with toluene 2× and again evaporated. 33.6 g of a yellowish oil were obtained as crude product; crystallization from acetone afforded 14.8 g of white solid.

ESI-MS [M+H$^+$]=340;
$^1$H-NMR (DMSO-d6, 400 MHz) diastereomer mixture: δ (ppm) 7.7–7.05 (m, 8H), 4.85–4.6 (m, 2H), 4.45 (m, 1H), 3.6/3.45 (s, 3H), 3.3 (m, 1H), 3.1/3,05 (dd, 1H).

tert-Butyl (6-oxo-6,11-dihydro-5H-dibenzo[b,e]azepin-11-yl) acetate (4)

a) Methyl (E,Z)-(6-oxo-5,6-dihydro-11H-dibenzo[b,e]azepin-11-ylidene)acetate (62 g, 279.2 mmol) was hydrogenated in 1.8 l of dioxane with 3.2 g of Pd (10% on carbon) at 60° C. and 130 bar for 60 h. Filtration through Celite and concentration of the filtrate afforded 62.3 g of white solid, which was then stirred with n-pentane.

58.7 g; ESI-MS [M+H$^+$]=282;

b) Methyl-(6-oxo-5,6-dihydro-1H-dibenzo[b,e]azepin-11-yl)-acetate (25 g, 88.7 mmol) was dissolved in 145 ml of 4:1 dioxane/$H_2O$ and, after addition of 4.98 g of KOH, heated to reflux. A further 2.5 g of KOH were added after 2 h. After the reaction was complete, the reaction mixture was concentrated and, after addition of $H_2O$ and adjustment to pH 2 with 2N HCl, extracted 2× with $CH_2Cl_2$. The combined organic phases were washed with saturated NaCl solution, dried ($MgSO_4$) and concentrated. The crude product obtained in this way was stirred with n-pentane and dried.

21.5 g, ESI-MS [M+H$^+$]=268.05 c) (6-Oxo-6,11-dihydro-5H-dibenzo[b,e]azepin-11-yl)acetic acid (18.8 g; 70.34 mmol) was suspended in 80 ml of benzene and heated to reflux. Over a period of 1 h, 5.3 eq. of dimethylformamide di-tert-butyl acetal (75.9 g) were added dropwise. After the reaction was complete, the mixture was evaporated, and the residue was taken up in $CH_2Cl_2$, washed with $NaHCO_3$ and saturated NaCl solution, dried and concentrated. The brown solid obtained in this way was purified by stirring with methyl tert-butyl ether.

26.9 g; ESI-MS [M−tBu+H+]=268.05;
$^1$H-NMR (270 MHz, DMSO-d6): d (ppm) 10.55 (s, 1H), 7.8–7.0 (m, 8H), 4.35 (m, 1H), 2.75 (d, 2H), 1.2 (s, 9H).

Ethyl 3-[11-(2-tert-butoxy-2-oxoethyl)-6-oxo-6,11-dihydro-5H-dibenzo[b,e]azepin-5-yl]propanoate (5)

tert-Butyl (6-oxo-6,11-dihydro-5H-dibenzo[b,e]azepin-11-yl)acetate 4 (2 g, 6.18 mmol) was dissolved in 25 ml of dry DMF and, at 10° C., 2.1 eq. of KOtBu (1.5 g) were added, and the mixture was stirred for about 20 min. Then, at RT 2.5 g of ethyl bromopropionate were added dropwise and, after stirring at RT for 1 h, further KOtBu (0.2 g) and ethyl bromopropionate (0.8 g) were added. After a further 2 h, the mixture was diluted with $CH_2Cl_2$, washed with $H_2O$, dried and concentrated. Chromatography on silica gel ($CH_2Cl_2CH_3OH$ 1 to 25%) afforded 1.2 g of the required product and 2.0 g of nonreacted precursor.

ESI-MS [M+H+]=424.15

3-[11-(2-tert-Butoxy-2-oxoethyl)-6-oxo-6,11-dihydro-5H-dibenzo[b,e]azepin-5-yl]propanoic acid (6)

Ethyl 3-[11-(2-tert-butoxy-2-oxoethyl)-6-oxo-6,11-dihydro-5-H-dibenzo[b,e]azepin-5-yl]propanoate 5 (2.55 g, 6.02 mmol) was dissolved in 15 ml of 2:1 dioxane/$H_2O$ and, after addition of 0.17 g of LiOH, stirred at RT. After the reaction was complete, the mixture was acidified with 2N HCl and, after addition of $CH_2Cl_2$, washed with saturated NaCl solution, dried and concentrated.

2.35 g; ESI-MS [M−tBu+H+]=340.15;

¹H-NMR (DMSO-d6, 200 MHz) diastereomer mixture: d (ppm) 7.75–7.05 (m, 8H), 4.8–3.8 (m, 3H), 3.5–3.1 (m, overlapped by H₂O), 2.75 (m, 2H, 1.3/1.2 (s, 9H).

tert-Butyl [6-(4,5-dihydro-1H-imidazol-2-yl)-3-pyridinyl]methyl-carbamate (trifluoroacetate) (7)

a) tert-butyl (6-cyanopyridin-3-yl)methylcarbamate (5.0 g; 21.43 mmol) in 300 ml of CH₃OH were mixed with 3.55 g of sodium methanolate. After 1 h at RT, 2.6 g of ethylenediamine (hydrochloride) were added and stirred overnight. The reaction mixture was evaporated and the resulting residue was stirred with a mixture of 100 ml of CH₂Cl₂ and 1 ml of CH₃OH. Insoluble solids were filtered off with suction, the filtrate was concentrated, and the residue was taken up in H₂O and again washed with CH₂Cl₂. Evaporation of the aqueous phase afforded 5.3 g of a white solid; ESI-MS [M+H⁺]=277.25.

b) 0.9 g of the Boc-protected amine in 20 ml of CH₂Cl₂ were mixed with 10 ml of TFA and stirred at 0° C. for 2 h. Evaporation of the reaction mixture afforded 1.75 g of a yellowish oil which was immediately employed further.

The amine required for further reaction was obtained by eliminating the Boc group with TFA (under standard conditions); the isolated TFA salts were then employed directly in the appropriate couplings.

tert-Butyl 1H-benzimidazol-2-ylmethylcarbamate (8)

3.32 g of a 30% NaOCH₃ solution were added to tert-butyl cyanomethylcarbamate (3 g; 19.21 mmol) in 20 ml of CH₃OH, and the mixture was stirred at room temperature for 1 h. After addition of 3.4 g of 1,2-phenylenediamine bishydrochloride, the reaction mixture was stirred further overnight and then added to 100 ml of H₂O, and the resulting solid was filtered off and dried in vacuo.

3.45 g; ESI-MS [M+H+]=248.15;

¹H-NMR (270 MHz; DMSO-d6) d (ppm) 12.60 (s, 1H), 7.30–7.15 (m 3H), 7.05 (m 2H), 4.15 (d, 2H), 1.29 (s, 9H).

The amine required for further reaction was obtained by eliminating the Boc group with TFA (under standard conditions); the isolated TFA salts were then employed directly in the appropriate couplings.

tert-Butyl 3H-imidazo[4,5-b]pyridin-2-ylmethylcarbamate (9)

A mixture of tert-butyl cyanomethylcarbamate (1.61 g; 10 mmol), 2,3-diaminopyridine (0.56 g; 5 mmol), N-acetylcysteine (1.68 g; 10 mmol) in 10 ml of CH₃OH was heated at 50° C. for 89 h. It was then concentrated, and the residue was taken up in a little CH₃OH and filtered through an acidic ion exchanger (acetate on polymeric support). Renewed concentration and chromatography on silica gel (CH₂Cl₂/CH₃OH 5%) afforded 1.09 g of the required product;

ESI-MS [M+H⁺]=249.15

¹H-NMR (270 MHz; DMSO-d6) d (ppm) 8.30 (m, 1H), 7.90 (m, 1H), 7.45 (m, broad, 1H), 7.20 (m 1H), 4.40 (d, 2H), 1.0 (s, 9H).

The amine required for further reaction was obtained by eliminating the Boc group with TFA (under standard conditions); the isolated TFA salts were then employed directly in the appropriate couplings.

[1-(2-Pyridinyl)-4-piperidinyl]methanamine (10)

a) 1-tert-Butyloxycarbonyl-4-(aminomethyl)piperidine (14 g; 65.33 mmol; prepared as described by Prugh et al., Synthetic Communications 22 (16), 2361–2365 (1992)) was dissolved in 50 ml of THF and, at 5° C., N-methylmorpholine (6.6 g) and benzyl chloroformate (12.6 g) were added, and the mixture was stirred for about 2 h. It was then concentrated, and the residue was taken up in CH₂Cl₂, washed with saturated NaCl solution, dried and filtered. The residue after concentration was 23.5 g of a yellow oil which was crystallized from methyl tert-butyl ether.

18 g; ESI-MS [M+H+]=293.15 b) 25 ml of TFA were added to 1-tert-butyloxycarbonyl-4-({[benzyloxy)carbonyl]amino}-methyl)piperidine 10a (15 g; 43.05 mmol) in 125 ml of CH₂Cl₂ at 0° C., and the mixture was stirred at 10° C. for 20 min and then at RT. Concentration of the mixture and crystallization of the resulting residue from diethyl ether afforded 14.5 g of the free amine as TFA salt (ESI-MS [M+H⁺]=249.25; melting point: 109–110° C.).

5 g of the TFA salt and 2.79 g of ethyldiisopropylamine (DIPEA) in 15 ml of 2-fluoropyridine were heated to reflux. After the reaction was complete, the mixture was concentrated, and the residue was taken up in ethyl acetate and washed 4× with H₂O and saturated NaCl solution. Drying, filtration and concentration afforded 4.49 g of a pale brown oil, which was crystallized from n-pentane.

4.02 g; ESI-MS [M+H⁺]=362.15 c) 3.9 g of (10b) in 150 ml of CH₃OH were hydrogenated with 0.2 g of Pd (10% on carbon) under standard conditions. Filtration of the reaction mixture through Celite and concentration afforded 2.3 g;

ESI-MS [M+H+]=192.15;

¹H-NMR (270 MHz; DMSO-d6) d (ppm) 8.1 (m, 1H), 7.5 (m, 1H), 6.8 (m, 1H), 6.55 (m, 1H), 4.3 (m, 2H), 2.7 (m 2H), 2.45 (m, 2H), 1.75 (m 2H), 1.5 (m 1H), 1.05 (m 2H).

1-tert-Butyloxycarbonyl-4-[(2-pyridinylamino)methyl]piperidine (11)

1-tert-Butyloxycarbonyl-4-(aminomethyl)piperidine (3 g; 14 mmol) and 10 ml of 2-fluoropyridine were heated to reflux for 4 h. Concentration and stirring of the crude product in n-pentane afforded 3 g of a white solid, melting point: 126–130° C.;

ESI-MS [M+H+]=292.15.

The amine required for further reaction was obtained by eliminating the Boc group with TFA (under standard conditions); the isolated TFA salts were then employed directly in the appropriate couplings.

N-[4-(Aminomethyl)benzyl]-2-pyridinamine (12)

a) 20 g of 2-aminopyridine were dissolved in 100 ml of CH₃OH and, after adjustment to pH 6 with isopropanolic HCl, 36 g of p-cyanobenzaldehyde were added. 9.35 g of sodium cyanoborohydride were added in portions over the course of 1 h and the mixture was stirred overnight. For workup, the suspension was concentrated, and the residue was taken up in 100 ml of water and adjusted to pH >10 with KOH. The aqueous phase was saturated with NaCl and extracted 3× with diethyl ether. The ether phase was filtered to remove a precipitate and then washed 3× with FeSO$_4$ solution, dried and concentrated. Purification of the residue by chromatography on silica gel (heptane/ethyl acetate 1:1) afforded 28.15 g of 4-[(2-pyridinylamino)methyl]benzonitrile.

b) 10 g of 4-[(2-pyridinylamino)methyl]benzonitrile were dissolved in 280 ml of ammoniacal methanol and, after addition of 10 g of Raney nickel, hydrogenated for 24 h. The residue after filtration and concentration was chromatographed on silica gel (ethyl acetate/ethanol 1:3).

5.18 g, ESI-MS: [M+H+]=214.

tert-Butyl [4-(1H-benzimidazol-2-yl)-1,3-thiazol-2-yl]methyl-carbamate (13)

In analogy to the preparation of 8, 1.89 g of a 30% NaOCH$_3$ solution were added to tert-butyl (4-cyano-1,3-thiazol-2-yl)methylcarbamate (2.5 g; 10.45 mmol) in 25 ml of CH$_3$OH, and the mixture was stirred at room temperature for 2 h. Addition of 1.9 g of 1,2-phenylenediamine bishydrochloride was followed by stirring overnight, and then the reaction mixture was added to 100 ml of H$_2$O, and the solid resulting after filtration was dried in vacuo.

3.0 g; ESI-MS: [M+H+]=331.15, $^1$H-NMR (400 MHz; DMSO-d6) d (ppm) 8.25 (s, 1H), 7.95 (m, 1H), 7.65 (m, 1H), 7.55 (m, 1H), 7.2 (m, 2H), 4.55 (m, 2H), 1.45 (s, 9H).

The amine required for further reaction was obtained by eliminating the Boc group with TFA (under standard conditions); the isolated TFA salts were then employed directly in the appropriate couplings.

Di(tert-butyl) 4-(1H-benzimidazol-2-yl)benzylimidodicarbonate (14)

Di(tert-butyl) 4-cyanobenzylimidodicarbonate (10 g; 30.1 mmol) was dissolved in 200 ml of pyridine and, after addition of 45 ml of triethylamine, H$_2$S was passed in at 0° C. for 1.5 h and the mixture was kept at RT overnight. The reaction mixture was concentrated in vacuo and coevaporated with toluene twice. Stirring of the resulting residue in diethyl ether afforded 8.5 g of white solid.

The thioamide (6 g; 16.37 mmol) was suspended in 40 ml of CH$_2$Cl$_2$ and, after addition of 22.3 g of CH$_3$I, stirred at RT overnight. The mixture was then evaporated, taken up in 20 ml of CH$_3$OH and, after addition of 1,2-phenylenediamine (1.95 g; 18.01 mmol), again stirred at RT overnight. Concentration of the mixture afforded 6.9 g of yellow solid.

ESI-MS [M+H+]=424.25;

The amine required for further reaction was obtained by eliminating the Boc group with TFA (under standard conditions); the isolated TFA salts were then employed directly in the appropriate couplings.

[5-(2-Methoxy-2-oxoethyl)-11-oxo-5,11-dihydro-10H-dibenzo[b,e][1,4]diazepin-10-yl]acetic acid (37)

a) A mixture of 5,10-dihydro-11H-dibenzo[b,e][1,4]diazepin-11-one (10 g; 47.6 mmol; preparation as described in Pharmazie 45, 1990, 555–559), 100 g of methyl bromoacetate, 0.5 g of KI and 180 ml of DMF was heated at 60° C. for 110 h. Concentration of the crude product on silica gel (CH$_2$Cl$_2$/CH$_3$OH 3→5%) and crystallization of the resulting oil from ethyl acetate afforded 7.1 g of gray solid; ESI-MS [M+H+]=283

$^1$H-NMR (400 MHz; DMSO-d$_6$): δ (ppm) 10.3 (s, 1H), 7.65 (d, 2H), 7.45 (m, 2H), 7.05–7.2 (m, 4H), 4.75 (d, 2H), 3.6 (s, 3H).

b) A solution of methyl (11-oxo-10,11-dihydro-5H-dibenzo[b,e]-[1,4]diazepin-5-yl)acetate 37a (7 g; 24.8 mmol) in 40 ml of DMF was added dropwise to a suspension of 1.3 g of NaH (60%; oil removed with n-pentane) in 10 ml of DMF at 5° C., and the mixture was stirred for about 30 min to complete formation of the anion. Then tert-butyl bromoacetate (5.4 g, 27.7 mmol) was added dry and the mixture was stirred at 10° C. for about 2 h. For workup, the mixture was mixed with H$_2$O, diluted with CH$_2$Cl$_2$ and washed with saturated NaCl solution. Drying and concentration of the CH$_2$Cl$_2$ phase afforded a black oil, which was purified by chromatography on silica gel (CH$_2$Cl$_2$/CH$_3$OH 2→10%);

7.8 g; ESI-MS [M−tBu+H+]=341 c) tert-Butyl [5-(2-methoxy-2-oxoethyl)-11-oxo-5,11-dihydro-10H-dibenzo[b,e][1,4]diazepin-10-yl]acetate 37b (7.8 g; 19.67 mmol) in 15 ml of CH$_2$Cl$_2$ was mixed with 10 ml of TFA and stirred at RT for 2 h. Concentration of the mixture and drying afforded 7.4 g of brown solid; ESI-MS [M+H+]=341

N-[4-(Aminomethyl)-1,3-thiazol-2-yl]-N'-benzylurea (hydrochloride) (38)

a) A solution of 123 g of pyridinium bromide perbromide in 600 ml of THF was slowly added dropwise to 2-(2-oxopropyl)-1H-isoindole-1,3 (2H)-dione (70 g; 0.345 mol) in 600 ml of THF, and the mixture was then stirred for about 3 h. For workup, the precipitated solids were filtered off, and the mother liquor was concentrated, taken up in ethyl acetate and thoroughly washed with aqueous bisulfite solution. Drying and concentration afforded 150 g of a yellow oil, which was stirred with methyl tert-butyl ether.

63.4 g; m.p.: 142 to 143° C.; ESI-MS [M+H+]=283.95 b) 2-(3-Bromo-2-oxopropyl)-1H-isoindole-1,3 (2H)-dione 38a (6 g; 21.27 mmol) and thiourea (2 g; 26.27 mmol) were stirred in 70 ml of THF at RT for about 2 h. The resulting precipitate was filtered off with suction and dried.

5 g; ESI-MS [M+H+]=260.05 c) 2-[(2-Amino-1,3-thiazol-4-yl)methyl]-1H-isoindole-1,3 (2H)-dione hydrobromide 38b (4.5 g; 13.23 mmol), benzyl isocyanate (1.8 g, 13.52 mmol) and 1.7 g of DIPEA were heated to reflux in 50 ml of toluene. After the reaction was complete, the mixture was evaporated, and the residue was taken up in CH$_2$Cl$_2$ and washed with 1 N HCl, saturated NaHCO$_3$ and NaCl solutions. Drying and concentration afforded 4.7 g of orange solid, which was recrystallized from CH$_3$OH.

3.0 g; ESI-MS [M+H+]=393.05

$^1$H-NMR (360 MHz, DMSO) δ ppm: 10.65 (s, 1H), 7.9 (m, 4H), 7.25 (m, 5H), 6.85 (s, 1H), 4.7 (s, 2H), 4.35 (d, 2H), d) N-Benzyl-N'-{4-[(1,3-dioxo-1,3-dihydro-2H-isoindol-2-yl)-methyl]-1,3-thiazol-2-yl}urea 38c (3 g; 7.64 mmol) was suspended in 50 ml of CH$_3$OH and, after addition of 2 g of hydrazine hydrate, stirred at RT for 2 h. The resulting solids were filtered off, and the resulting mother liquor was evaporated and stirred with 0.5 N HCl. Renewed filtration and evaporation of the mother liquor led to a concentration of the required product, and thus this purification step was repeated 3×.

0.78 g; ESI-MS [M+H$^+$]=263.05

[4-(Aminomethyl)-1,3-thiazol-2-yl]guanidine (bishydrochloride) (39)

a) 2-(3-Bromo-2-oxopropyl)-1H-isoindole-1,3 (2H)-dione 38a (10 g; 35.45 mmol) and 2-iminothiobiuret (4.6 g; 38.99 mmol) were stirred in 150 ml of THF at RT for about 2 d. The resulting precipitate was filtered off with suction and dried; 11.4 g; ESI-MS [M+H$^+$]=302.15.

b) 5 g of 39a were treated with hydrazine hydrate in CH$_3$OH in analogy to 38d. Stirring of the resulting crude product with 0.5 N HCl and subsequently with ethanol afforded 3.16 g; ESI-MS [M+H$^+$]=172.05.

N-[4-(Aminomethyl)benzyl]-N'-benzylurea (40)

340 mg (2.5 mmol) of diamino-p-xylene were introduced into 15 ml of acetonitrile and cooled to 0 to 5° C. and, over the course of 5 min, 0.29 ml of benzyl isocyanate was added and the mixture was then stirred at RT for 16 h. The resulting suspension was added to water, and the precipitate was filtered off with suction, washed with water and dried (402 mg). ESI-MS [M+H$^+$]=270.

N-[3-(Aminomethyl)phenyl]-N'-benzylurea (hydrochloride) (41)

a) 4.7 g (25 mmol) of m-nitrobenzylamine were added to 250 ml of CH$_2$Cl$_2$ and, after addition of 1.36 ml of DIPEA, the mixture was refluxed until the benzylamine had dissolved. The solution was cooled to 0° C., and di-tert-butyl carbonate (1.1 eq.) was added dropwise. The mixture was then stirred at RT for 16 h, and subsequently the solution was extracted with water and saturated NaHCO$_3$ solution. The organic phase was dried and concentrated, and the resulting residue was crystallized from 30 ml of diethyl ether (5.07 g).

b) 4.69 g of the above nitro compound were dissolved in 50 ml of ethanol and hydrogenated with 460 mg of 5% Pd on active carbon under atmospheric pressure. The reaction was complete after 2 h. The filtrate after filtration was concentrated, and the remaining oil was immediately reacted further (3.80 g).

c) The oil was dissolved in 100 ml of THF, and 3.66 ml of DIPEA and then dropwise 2.60 g of benzyl isocyanate were added to the solution. The mixture was stirred at RT for 16 h, then under reflux for 6 h and then at RT for a further 16 h. It was concentrated and crystallized from 30 ml of ethyl acetate, and the resulting precipitate was filtered off with suction and dried; 4.90 g; ESI-MS [carbamic acid fragment+H$^+$]=300.

d) The Boc compound was dissolved in 20 ml of THF, and 5 ml of HCl in diethyl ether (saturated at 0° C.) were added. After 1 h, a further 15 ml of HCl in diethyl ether were added and the mixture was stirred for 16 h. The precipitate which had formed was filtered off with suction, washed with THF and diethyl ether and dried (3.72 g). ESI-MS [M+H$^+$]=256.

3-Amino-N-(1H-imidazol-2-yl)propanamide (42)

a) Z-β-alanine (10 g; 44.8 mmol) was dissolved in 200 ml of DMF, and 15.86 g (3.5 eq) of N-methylmorpholine and 5.9 g (0.5 eq) of 2-aminoimidazole sulfate were added. At −10° C., 7.87 g (1.3 eq) of HOBt and 11.16 g (1.3 eq) of N'-(dimethylaminopropyl)-N-ethylcarbodiimide were added, and the mixture was stirred for 1 h while warming to RT and then for 18 h. 150 ml of diethyl ether were added, whereupon a white solid precipitated and was filtered off with suction. The residue was washed with cold diethyl ether and suspended in ethyl acetate, and 1 N HCl was added until the reaction was acidic. The aqueous solution was extracted 1× with ethyl acetate, and then the aqueous phase was adjusted to a basic pH with 10% NaOH at 4° C. The resulting precipitate was filtered off with suction and washed with water. 5.4 g; ESI-MS [M+H$^+$]=289.05.)

b) 5.3 g of the Z compound 42a were suspended in 250 ml of ethanol, and 530 mg of 10% Pd on active carbon were added. The mixture was hydrogenated with H$_2$ at RT for 18 h and then diluted with CH$_3$OH, and the suspension was boiled to dissolve the product precipitate. Filtration and concentration of the solution afforded 1.5 g; ESI-MS [M+H$^+$]=155.05.

4-(Aminomethyl)-N-benzylpiperidine-1-carboxamide (43)

a) Benzyl 4-(aminomethyl)-1-piperidinecarboxylate (trifluoroacetate) (4 g; 11.04 mmol; preparation as described in 10b) was suspended in 60 ml of toluene and heated with 1.43 g of DIPEA and benzyl isocyanate (1.62 g, 12.14 mmol) to reflux for 4 h. After evaporation of the reaction mixture, the residue was taken up in CH$_2$Cl$_2$ and extracted 2× each with 1 N HCl and saturated NaCl solutions, and the organic phase was dried and concentrated. 4.2 g; ESI-MS [M+H$^+$]=382.25.

b) 4 g of benzylurea 43a were dissolved in a 3:1 ethyl acetate/CH$_3$OH mixture with heating and, after addition of 0.2 g of 10% Pd on active carbon, hydrogenated under standard conditions at 35 to 40° C. After the reaction was complete, the mixture was filtered through Celite and evaporated.

2.8 g; ESI-MS [M+H$^+$]=248.15.
$^1$H-NMR (400 MHz, DMSO) δ ppm: 7.4–7.15 (m, 11H), 7.05 (t, 1H), 5.08 (s, 2H), 4.25 (d, 2H), 3.95 (d, 2H), 2.8 and 2.65 (each m, 2H), 1.6 (m, 3H), 0.95 (m, 2H).

[4-(1H-Benzimidazol-2-yl)-thien-2-yl]methanamine (trifluoroacetate) (44)

The tert-butyl-(4-cyanothien-2-yl)methylcarbamate used as precursor was prepared by standard methods from 5-(aminomethyl)-3-thiophenecarbonitrile (WO 98/06741).

a) 3.6 g of a 30% NaOCH$_3$ solution were added to tert-butyl (4-cyanothien-2-yl)methylcarbamate (5 g; 20.98 mmol) in 70 ml of CH$_3$OH and the mixture was stirred at room temperature for 2 h. Addition of 3.6 g of 1,2-phenylenediamine bishydrochloride was followed by stirring overnight, and then the reaction mixture was added to 50 ml of H$_2$O and extracted with CH$_2$Cl$_2$. Drying and concentration of the organic phase afforded 4.3 g of a yellow solid, which was purified by chromatography on silica gel (CH$_2$Cl$_2$/CH$_3$OH 1→10%).

1.6 g; ESI-MS: [M+H$^+$]=333.15.

b) 1.5 g of the Boc compound 44a were dissolved in 10 ml of CH$_2$Cl$_2$ and, after addition of 15 ml of TFA at 0° C., stirred at room temperature for 2 h. Evaporation of the reaction mixture and stirring with n-pentane afforded 1.5 g of the amine as trifluoroacetate.

[5-(1H-Benzimidazol-2-yl)thien-2-yl]methanamine (45)

Preparation took place in analogy to 44 starting from 5-(aminomethyl)thiophene-2-carbonitrile (preparation as described in WO 95/23609). The crude product obtained after TFA cleavage was dissolved in water and extracted 2× with diethyl ether, and the aqueous phase was adjusted to pH 10–11 and then extracted 2× with ethyl acetate. The aqueous phase was saturated with NaCl and again extracted with ethyl acetate. The combined organic phases were dried and concentrated (6.3 g); ESI-MS [M+H$^+$]=230.1.

2-(Piperidin-4-ylamino)pyridine (46)

a) Ethyl 4-amino-1-piperidinecarboxylat (6 g, 34.8 mmol) and 25 g of 2-fluoropyridine were refluxed for 48 h. The solid formed after cooling was filtered off with suction, stirred with n-pentane and dried; 6.26 g of yellow powder; ESI-MS [M+H$^+$]=250.15.

b) 6 g of ethyl 4-(pyridin-2-ylamino)piperidine-1-carboxylate 46a were refluxed in 30 ml of 47% HBr for 6 h. Evaporation of the mixture, stirring of the resulting crude product with ethyl acetate/CH$_3$OH (9:1) and renewed drying afforded 7.1 g of white solid; ESI-MS [M+H$^+$]=178.15.

N-[4-(Aminomethyl)phenyl]-1H-benzimidazole-2-amine (hydrochloride) (47)

a) 20 g of tert-butyl 4-aminobenzylcarbamate (89.97 mmol)—dissolved in 100 ml of CH$_3$CN—were added dropwise to a solution of 24.5 g of thiocarbonyldiimidazole and 1.56 g of imidazole in 600 ml of CH$_3$CN at 0° C., and the mixture was stirred at RT overnight. Then 19.5 g of 1,2-phenylenediamine were added and the mixture was again stirred at RT for 2 h. For work up, the reaction mixture was evaporated in vacuo, and the residue was taken up in CH$_2$Cl$_2$, washed 7× with 10% citric acid solution and 2× with saturated NaCl solution, dried over Na$_2$SO$_4$, filtered and concentrated. The crude product obtained in this way (31.78 g; brown foam) was immediately reacted without further purification; ESI-MS [M+H$^+$]=373.15.

$^1$H-NMR (360 MHz, DMSO) δ ppm: 9.5 and 9.05 (each s, 1H), 7.45 (d, 2H), 7.35 (m, 1H), 7.20 (d, 1H), 7.15, 6.95, 6.75, 6.60 (each m, 1H), 4.85 (s, 2H), 4.10 (d, 2H), 1.35 (s, 9H).

b) The crude product 47a was dissolved together with 36.7 g of HgO (yellow) and 0.4 g of sulfur in 750 ml of ethanol and refluxed for 2 h. The reaction mixture was then filtered twice through Celite and evaporated to dryness; 20.7 g,

ESI-MS [M+H$^+$]=339.15.

c) 7 g of the crude product 47b were introduced into 70 ml of CH$_2$Cl$_2$ and, after addition of 35 ml of HCl in diethyl ether (saturated at 0° C.), stirred at RT for 2 h. The resulting precipitate was filtered off with suction, washed with CH$_2$Cl$_2$ and dried.

6.7 g of brown amorphous solid; ESI-MS [M+H$^+$]=239.15

$^1$H-NMR (360 MHz, DMSO) δ ppm: 11.6 (s broad, 1H), 8.4 (s broad, 3H), 8.25 (s broad, 1H), 7.65 and 7.55 (each d, 2H), 7.45 and 7.3 (each m, 2H), 4.19 (m, 2H).

N$^1$-(1H-Benzimidazol-2-yl)pentane-1,5-diamine (hydrochloride) (48)

Preparation took place in analogy to the synthesis of 47 starting from 7 g of N-Boc-1,5-diaminopentane hydrochloride (29.3 mmol). After reaction in analogy to 47a, 10.3 g of N-Boc-5-{[(2-aminoanilino)carbothioyl]amino}pentan-1-amine were obtained; ESI-MS [M+H$^+$]=353.25. Cyclodesulfurization and subsequent elimination of the Boc group with TFA afforded an oily crude product, which was taken up in CH$_3$OH and converted into the corresponding hydrochloride with 250 ml of ethereal HCl (saturated at 0° C.). Stirring of the resulting solids with a CH$_3$OH/methyl tert-butyl ether mixture afforded 1.8 g of a reddish amorphous solid.

$^1$H-NMR (360 MHz, DMSO) δ ppm: 9.30 (t, 1H), 8.15 (s broad, 3H), 7.40 and 7.25 (each m, 2H), 3.35 (m, 2H overlapped by H$_2$O peak), 2.80 (m, 2H), 1.65 (m, 4H), 1.45 (m, 2H).

N$^1$—(1H-Benzimidazol-2-yl)butane-1,4-diamine (trifluoroacetate) (49)

Preparation took place in analogy to the preparation of compound 47 starting from 9.87 g of N-Boc-1,4-diaminobutane (52.3 mmol). After reaction in analogy to 49a, 17.08 g of N-Boc-4-{[(2-aminoanilino)carbothioyl]amino}butan-1-amine were obtained; ESI-MS [M+H$^+$]=338.99.

Subsequent cyclodesulfurization and Boc elimination with TFA afforded a brown solid, which was stirred several times with n-pentane and then recrystallized from a CH$_3$OH/methyl tert-butyl ether mixture; 14.35 g, ESI-MS [M+H$^+$]=205.15.

$^1$H-NMR (360 MHz, DMSO) δ ppm: 9.20 (t, 1H), 7.80 (s broad, 3H), 7.35 and 7.20 (each m, 2H), 3.40 (m, 2H partially overlapped by H$_2$O peak), 2.80 (m, 2H), 1.65 (m, 4H).

N-(Piperidin-4-ylmethyl)-1H-benzimidazol-2-amine (trifluoro-acetate) (50)

a) A solution of tert-butyloxycarbonyl-4-(aminomethyl)-1-piperidine (5.39 g; 25 mmol) in 25 ml of CH$_3$CN was added dropwise to 6.75 g of thiocarbonyldiimidazole and 0.5 g of imidazole in 100 ml of CH$_3$CN at 0° C., and the mixture was stirred at RT for 3 h. Then 1,2-phenylenediamine (5.5 g; 50.86 mmol) was added and the mixture was heated at 60° C. for about 1 h. The solid resulting on cooling was filtered off with suction and dried.

6.79 g; ESI-MS [M+H$^+$−$^t$Bu]=309.15.

b) tert-Butoxycarbonyl-4-({[(2-aminoanilino)carbothioyl]-amino}methyl)1-piperidine 50a (5 g; 13.72 mmol), 5.94 g of HgO (yellow) and 0.6 g of sulfur in 150 ml of ethanol were refluxed for 1 h. The mixture was filtered 2× through Celite and evaporated, and the resulting crude product was purified by chromatography on silica gel (CH$_2$Cl$_2$/CH$_3$OH 5→25%).

2.65 g; ESI-MS [M+H$^+$]=331.25.

$^1$H-NMR (360 MHz, DMSO) δ ppm: 7.15 and 6.9 (each m, 2H), 3.95 (d, 2H), 3.2 (m 2H), 2.7 (br m; 2H), 1.8 (m, 1H), 1.7 (m, 2H), 1.35 (s, 9H), 1.05 (m, 2H).

c) tert-Butyloxycarbonyl-4-[(1H-benzimidazol-2-ylamino)methyl]-1-piperidine 50b (2.65 g; 8.02 mmol) were treated with 10 ml of TFA under standard conditions. Concentration and stirring of the crude product with n-pentane afforded 2.3 g; ESI-MS [M+H$^+$]=231.15.

$^1$H-NMR (360 MHz, DMSO) δ ppm: 13.25 (s, 1H), 9.35 (m, 1H), 8.8 and 8.5 (each br s, 1H), 7.4 and 7.20 (each m, 2H), 3.3 (m, 4H), 2.85 (m, 2H), 1.9 (m, 3H), 1.35 (m, 2H).

N-[4-(Aminomethyl)-1,3-thiazol-2-yl]pyridin-2-amine (bishydrochloride) (51)

a) 2-Aminopyridine (11 g; 116.9 mmol) and benzyl isothiocyanate (21 g; 128.7 mmol) were refluxed in 250 ml of acetone for 3 h. The mixture was then evaporated and the resulting residue was stirred first with acetone/n-pentane and then only with n-pentane.
21.4 g; ESI-MS [M+H$^+$]=258.05.
b) N-Benzoyl-N'-pyridin-2-ylthiourea 51a (5 g; 19.43 mmol) was introduced into 100 ml of an acetone/CH$_3$OH mixture. 1.34 g of K$_2$CO$_3$ in 5 ml of H$_2$O were added and the mixture was refluxed for 2 h. For workup, the precipitate which had formed was filtered off, the mother liquor was evaporated, and the resulting residue was added to H$_2$O. Extraction with CH$_2$Cl$_2$, drying and evaporation of the organic phases afforded 5.4 g;
ESI-MS [M+H$^+$]=154.05.
$^1$H-NMR (270 MHz, DMSO-d$_6$) δ ppm: 10.65 (s, 1H), 10.55 (s, 1H), 8.9 (s, 1H), 8.25, 7.75, 7.20, 7.10 (each m, 1H).
c) N-Pyridin-2-ylthiourea 51b (5 g; 35.9 mmol) and 2-(3-bromo-2-oxopropyl)-1H-isoindole-1,3 (2H)-dione (9.1 g; 32.26 mmol) were stirred in 500 ml of THF at RT for 2 h. The precipitate which had formed was filtered off and dried. 12.3 g of white solid; ESI-MS [M+H$^+$]=337.05.
d) Elimination of the phthaloyl group was carried out analogously starting from 2-{[2-(pyridin-2-ylamino)-1,3-thiazol-4-yl]methyl}-1H-isoindole-1,3(2H)-dione 51c (10 g; 23.96 mmol) with 7 g of hydrazine hydrate in 250 ml of CH$_3$OH. Subsequent workup afforded 4.15 g of yellow solids; ESI-MS [M+H$^+$]=207.05.

N-[5-(Aminomethyl)-1,3-thiazol-2-yl]pyridin-2-amine (bishydrochloride) (52)

Preparation took place in analogy to 51 using 2-chloro-3-(1,3-dioxo-1,3-dihydro-2H-isoindol-2-yl)propanal (preparation described in *THL* 39 (1998), 8085–8088). After cleavage of the phthaloyl group with hydrazine hydrate under standard conditions and stirring the crude product with CH$_2$Cl$_2$, 1.12 g of yellow solids were obtained; ESI-MS [M+H$^+$]=207.05.

N-[5-(Aminomethyl)-1,3-thiazol-2-yl]guanidine (dihydrochloride) (53)

a) 31 g (130 mmol) of 2-chloro-3-(1,3-dioxo-1,3-dihydro-2H-iso-indol-2-yl)propanal (preparation described in *THL* 39 (1998), 8085–8088) and 15.4 g of amidinothiourea were heated in 200 ml of n-butanol at 110° C. for 75', and then the mixture was evaporated and the residue was mixed with CH$_2$Cl$_2$ and concentrated NH$_3$. Evaporation of the organic phase, purification of the residue by chromatography on silica gel ((CH$_2$Cl$_2$/CH$_3$OH 0 to 5%) and crystallization from acetone afforded 12.3 g of N-{5-[(1,3-dioxo-1,3-dihydro-2H-isoindol-2-yl)methyl]-1,3-thiazol-2-yl}guanidine.
b) 1 g of 53a in 20 ml of CH$_3$OH was mixed with 0.81 ml of hydrazine hydrate and stirred at RT for 2 h. The mixture was then cooled to 0° C. and filtered, and the filtrate was concentrated and stirred with dilute HCl. This procedure was repeated several times, and the crude product obtained in this way was then stirred with ethanol; 0.92 g of white solids, ESI-MS [M+H$^+$]=172.05.

tert-Butyl 2-[4-(1H-benzimidazol-2-yl)phenyl]ethylcarbamate (54)

Preparation took place in analogy to the synthesis of building block 14 starting from tert-butyl 2-(4-cyanophenyl) ethylcarbamate. The crude product obtained after reaction with H$_2$S, alkylation with CH$_3$I and reaction with 1,2-phenylenediamine was purified by chromatography on silica gel (CH$_2$Cl$_2$/CH$_3$OH 4 to 50%) (4.8 g); ESI-MS [M+H$^+$] =338.15.

→ the amine required for the subsequent reaction was obtained by eliminating the Boc group with TFA (under standard conditions); the isolated TFA salts were then employed directly in the appropriate couplings.

N-{[5-(Aminomethyl)thien-3-yl]methyl}pyridin-2-amine (trifluoroacetate) (55)

a) A solution of tert-butyl (4-cyanothien-2-yl)methylcarbamate (7 g; 29.4 mmol) in 120 ml of ethanol was saturated with NH$_3$ and then hydrogenated in the presence of Ra—Ni (9 g of aqueous suspension; decanted with ethanol) under standard conditions. Filtration of the reaction mixture, evaporation and chromatography of the resulting residue on silica gel (CH$_2$Cl$_2$/CH$_3$OH plus aqueous NH$_3$) afforded 4.4 g of the amine as yellowish oil.
b) 1.2 g of the amine 55a (4.3 mmol), 0.6 g of ethyldiisopropylamine and 15 g of 2-fluoropyridine were refluxed for 20 h. The residue obtained after evaporation of the mixture was taken up in CH$_2$Cl$_2$, washed with 0.1N HCl and saturated NaCl solutions, dried and again evaporated.
1 g; ESI-MS [M+H$^+$]=320.15.
c) 0.9 g of the Boc-protected amine 55b were dissolved in 10 ml of CH$_2$Cl$_2$ and, after addition of 5 ml of TFA at 0° C., stirred at room temperature for 1 h. Evaporation of the reaction mixture afforded 1.65 g of a brownish oil, which was reacted directly without further purification (ESI-MS [M+H$^+$]=220.05).

N$^1$-Methyl-N$^2$-pyridin-2-ylethane-1,2-diamine (acetate) (56)

a) tert-Butyl 2-aminoethyl(methyl)carbamate (2.8 g; 16.1 mmol) and 19 ml of 2-fluoropyridine were refluxed for about 23 h. Evaporation of the reaction mixture afforded 4 g of a brown oil (ESI-MS [M+H$^+$]=252.15) which was directly reacted further.
b) 2 g of the crude product 56a were stirred in 30 ml of TFA at RT overnight. The mixture was evaporated and purified by MPLC on RP silica gel (CH$_3$CN/H$_2$O plus 0.1% acetic acid);
2.2 g; ESI-MS [M+H$^+$]=152.1.

N-[4-(Aminomethyl)phenyl]-2-pyridinamine (57)

Preparation took place in analogy to 56 starting from tert-butyl 4-aminobenzylcarbamate. 38 mg of the title compound were isolated; ESI-MS [M+H$^+$]=200.15.

N-[4-(Aminomethyl)phenyl]-N'-benzylurea (trifluoroacetate) (58)

a) Triethylamine (6.8 g, 67.12 mmol) and then, at 0° C., di-tert-butyl dicarbonate (18.6 g, 85.00 mmol) were added to 4-aminobenzylamine (10.0 g, 81.85 mmol) in 150 ml of $CH_2Cl_2$. The mixture was stirred at 0° C. for 1 h and at RT for 2 h. For workup, 150 ml of a 1% aqueous citric acid solution were added, the phases were separated, and the aqueous phase was back-extracted twice with $CH_2Cl_2$ (150 ml). Renewed washing with $H_2O$, drying of the combined organic phases with $Na_2SO_4$ and evaporation afforded a solid which was stirred with a little diisopropyl ether, filtered off with suction and dried.
13.0 g; ESI-MS [M+H$^+$–$^t$Bu]=167.05.
$^1$H-NMR (360 MHz, CDCl$_3$) δ (ppm): 7.04 (2H, d), 6.61 (2H, d), 4.78 (1H, s br.), 4.17 (2H, d), 3.67 (2H, s br.), 1.46 (9H, s).

b) Benzyl isocyanate (2.40 g, 18.00 mmol) was added to a solution of the protected amine 58a (4.0 g, 17.99 mmol) and triethylamine (1.82 g, 18.00 mmol) in 220 ml of 10:1 toluene/DMF while cooling in ice. The reaction mixture was stirred at RT overnight. It was possible for part of the urea which had formed to be filtered off directly as precipitate and dried. The filtrate was washed twice with $H_2O$, dilute tartaric acid to pH 3 and again twice with $H_2O$ to pH 5, and the organic phase was then dried and evaporated. A total of 6.0 g was obtained in this way; ESI-MS [M+H$^+$–$^t$Bu]=300.15.

c) The urea 58b obtained in this way was introduced into 90 ml of $CH_2Cl_2$ and, at 0° C., TFA (2.24 g, 196.25 mmol)—dissolved in 90 ml of $CH_2Cl_2$—was added dropwise. After 3 h, a further 1 ml of TFA was added, and the mixture was then stirred at RT overnight. Addition of a further 1 ml of TFA was followed by stirring for 5 h, and then the mixture was poured into ice-water and extracted with ethyl acetate (2×50 ml). The aqueous phase was basified with 2N NaOH solution and extracted with $CH_2Cl_2$ (2×50 ml). The insoluble portion between the phases was filtered off and dried.
4 g; ESI-MS [2M+H$^+$]=511.35.
$^1$H-NMR (200 MHz, DMSO) δ (ppm): 8.52 (1H, s), 7.39–7.07 (9H, m), 6.62 (1H, t), 4.27 (2H, d), 3.61 (2H, s).

[4-(Aminomethyl)phenyl]guanidine (bishydrochloride) (59)

p-Aminobenzylamine (6.7 g; 54.84 mmol) was suspended in 20 ml of 6N HCl and, while refluxing, 5.3 g of cyanamide—dissolved in 5 ml of $H_2O$—were slowly added dropwise. After the reaction was complete, 50% NaOH solution was added to the solution at 0° C., and the resulting precipitate was filtered off with suction, boiled in 50 ml of ethanol and filtered. Concentration of the mother liquor and stirring of the resulting residue with diethyl ether afforded 1.4 g of yellow solid; m.p.: 255° C.

[4-(5-Chloro-1H-benzimidazol-2-yl)phenyl]methanamine (trifluoroacetate) (60)

Preparation took place in analogy to building block 14 by reaction with 4-chloro-1,2-diaminobenzene (104 mg); ESI-MS [M+H$^+$]: 258.05, 129.6.

[4-(5,6-Dimethyl-1H-benzimidazol-2-yl)phenyl]methanamine (trifluoroacetate) (61)

Preparation took place in analogy to building block 14 by reaction with 4,5-diamino-o-xylene (230 mg); ESI-MS [M+H$^+$]: 253.1, 252.1, 147.1, 126.6.

N-[2-(4-Piperidinyl)ethyl]-2-pyridinamine (tristrifluoroacetate) (62)

Synthesis took place in analogy to building block 56 starting from 2-(4-piperidinyl)ethanamine which was previously converted under standard conditions into the corresponding tert-butyl 2-(4-piperidinyl)ethylcarbamate. 251 mg of the title compound were isolated; ESI-MS [M-3CF$_3$COO-+H+]: 206.1, 103.7.

N-[2-(3-Pyrrolidinyl)ethyl]-2-pyridinamine (tristrifluoroacetate) (63)

Synthesis took place in analogy to building block 56 starting from 2-(3-pyrrolidinyl)ethanamine which was previously converted under standard conditions into the corresponding tert-butyl 2-(3-pyrrolidinyl)ethylcarbamate. 500 mg of the title compound were isolated; ESI-MS [M-3CF$_3$COO—+H$^+$]: 192.15.

{4-[(3-Phenylpropanoyl)amino]phenyl}methanamine (hydro-chloride) (64)

a) 350 mg (1.66 mmol) of 3-phenylpropionic acid were dissolved in 20 ml of THF and, at 0° C., 1.24 g of DIPEA and 2.3 ml of 50% propanephosphonic anhydride solution in THF were added. After 15 min, 350 mg (1.57 mmol) of tert-butyl 4-aminobenzylcarbamate in 5 ml of THF were added dropwise, and the mixture was warmed to RT and stirred for 16 h. It was concentrated, the residue was taken up in 70 ml of $H_2O$/ethyl acetate, and the organic phase was washed with saturated NaHCO$_3$ solution, 1% citric acid and $H_2O$, dried and concentrated (500 mg); ESI-MS [M+H$^+$-t-butyl]=299.

b) 880 mg (2.48 mmol) of the above compound were dissolved in 20 ml of THF, and about 20 ml of HCl in diethyl ether (saturated at 0° C.) were added. The solution was then stirred at RT for 2 d and the resulting precipitate was filtered off and dried (700 mg); ESI-MS [M+H$^+$–NH$_4^+$]=234.

(4-{[(Benzyloxy)carbonyl]amino}phenyl)methanamine (hydrochloride) (65)

a) 730 mg (3.28 mmol) of tert-butyl 4-aminobenzylcarbamate were dissolved in 20 ml of THF and, after addition of a solution of 1.18 g of NaHCO$_3$ in 10 ml of water, cooled to 0° C. 590 mg of benzyloxycarbonyl chloride were added dropwise to this mixture, and it was stirred at RT overnight. The residue after concentration was dissolved in 70 ml of $H_2O$/ethyl acetate, and the organic phase was separated off and washed with saturated NaHCO$_3$ solution, 1% citric acid and $H_2O$. Drying and concentration afforded 1.08 g; ESI-MS [M+Na$^+$]=379.

b) The product from the previous stage was dissolved in 10 ml of THF, and in 20 ml of HCl in diethyl ether (saturated at 0° C.) were added. The solution was stirred overnight, and the resulting crystals were filtered off with suction (800 mg); ESI-MS [M+H$^+$–NH$_3$]=240.

[11-(2-tert-Butoxy-2-oxoethyl)-6-oxo-6,11-dihydro-5H-dibenzo[b,e]azepin-5-yl]acetic acid (66)

Alkylation of tert-butyl (6-oxo-6,11-dihydro-5H-dibenzo[b,e]azepin-11-yl)acetate (4) with methyl bromoacetate in analogy to the synthesis of building block 1 afforded 13.8 g of a pale yellowish oil, which was directly hydrolyzed further with KOH in dioxane/$H_2O$ (11.2 g); ESI-MS [M+H$^+$–$^t$Bu]=326.15.

$^1$H-NMR (DMSO-d6, 360 MHz) diastereomer mixture: δ (ppm): 7.80–7.0 (m, 8H), 4.8–4.6 (m, 2H), 4.55 (m, 1H), 3.6–3.1 (broad m, overlapped by $H_2O$, 2H), 3.05 (m, 2H), 1.3/1.15 (s, 9H).

[6-(1H-Benzimidazol-2-yl)pyridin-3-yl]methanamine (bistrifluoroacetate) (67)

a) Preparation took place in analogy to 13 starting from tert-butyl (6-cyanopyridin-3-yl)methylcarbamate (6.0 g, 25.72 mmol); crystallization of the crude product from methanol afforded 5.15 g; ESI-MS [M+H$^+$]=325.
b) 0.55 g of the Boc-protected amine 67a in 10 ml of $CH_2Cl_2$ were mixed with 5 ml of TFA and stirred at RT for 2 h. Evaporation of the reaction mixture afforded 0.95 g of a white solid; ESI-MS [M+H$^+$]=225.25.

N$^1$-Pyridin-2-ylpropane-1,3-diamine (68)

2-Bromopyridine (100 g; 0.633 mol) and 1,3-diaminopropane (234.5 g; 3.16 mol) were refluxed for 7 h. After the reaction was complete, the mixture was evaporated, and distillation of the remaining residue under oil pump vacuum afforded 43 g of the required product; ESI-MS [M+H$^+$]=152.15.

$^1$H-NMR (360 MHz, CDCl$_3$) δ (ppm): 8.05 (d, 1H), 7.36 (t, 1H), 6.51 (t, 1H), 6.36 (d, 1H), 4.98 (s, 1H), 3.35 (s, 2H), 2.82 (t, 2H), 1.73 (m, 1H), 1.32 (s, 2H).

(11E/Z)-11-(3-Methoxy-3-oxopropylidene)-6-oxo-6,11-dihydro-5H-dibenzo[b,e]azepin-5-yl acetate (69)

a) A suspension of 100 g (448 mmol) of 5H-dibenzo[b,e]azepine-6,11-dione in 2000 ml of toluene was added dropwise to 448 ml of a 1.5 molar vinyl Grignard solution while cooling in ice. The mixture was stirred at RT overnight and then 70 ml of ice-water were added, and precipitated salts were filtered off with suction, dried and concentrated to half the original volume. Filtration with suction and drying of the resulting precipitate afforded a total of 64.2 g.
b) A mixture of 39 g of 69a, 3 g of triphenylphosphine, 1 g of PdCl$_2$ and 40 ml of ethanol was treated with CO (550 to 650 bar) in a 300 ml autoclave at 80 to 100° C. for 20 h. The resulting precipitate was filtered off with suction, recrystallized from glacial acetic acid and then stirred with $CH_2Cl_2$ (33 g; m.p.: >250° C.).

11-(3-Methoxy-3-oxopropyl)-6-oxo-6,11-dihydro-5H-dibenzo-[b,e]azepin-5-yl acetate (70)

Hydrogenation of 69 in analogy to the preparation of 2 afforded 100 mg of methyl 3-[5-(2-tert-butoxy-2-oxoethyl)-6-oxo-6,11-dihydro-5H-dibenzo[b,e]azepin-11-yl]propanoate, which were then reacted with TFA to give the title compound (90 mg); ESI-MS [M+H$^+$]=354.25.

(10E/Z)-10-(2-Methoxy-2-oxoethylidene)-4-oxo-4H-thieno[3,4-c][1]benzazepin-5 (10H)-yl acetate (71)

4H-Thieno[3,4-c][1]benzazepine-4,10 (5H)-dione (preparation described in EP 0209022; 0.9 g; 4.33 mmol) was reacted by a standard method with methyl diethyl phosphonoacetate and sodium methanolate as base in 100 ml, and purification of the crude product by chromatography on silica gel ($CH_2Cl_2$/$CH_3OH$ 0 to 2%) and stirring in diethyl ether afforded 1.1 g. Alkylation with tert-butyl bromoacetate in analogy to 2 and subsequent ester cleavage with TFA afforded 85 mg of the title compound; ESI-MS [M+H$^+$]=344.

10-(2-Methoxy-2-oxoethyl)-4-oxo-4H-thieno[3,4-c][1]benzazepin-5(10H)-yl acetate (72)

Hydrogenation of 71 in analogy to the preparation of 2 and subsequent TFA cleavage afforded the title compound (45 mg); ESI-MS [M+H$^+$]=346.

(9E/Z)-9-(2-Methoxy-2-oxoethylidene)-5-oxo-9H-dithieno[3,4-b: 3,4-e]azepin-4 (5H)-yl acetate (73)

Synthesis took place in analogy to building block 71 starting from 9H-dithieno[3,4-b:3,4-e]azepine-5,9 (4H)-dione (preparation described in EP 0209773). 62 mg of the title compound were isolated; ESI-MS [M+H$^+$]=350.

9-(2-Methoxy-2-oxoethyl)-5-oxo-9H-dithieno[3,4-b: 3,4-e]azepin-4(5H)-yl acetate (74)

Hydrogenation of 73 in analogy to the preparation of 2 and subsequent TFA cleavage afforded the title compound (20 mg); ESI-MS [M+H$^+$)=352.

2-{[11-(2-tert-Butoxy-2-oxoethyl)-6-oxo-6,11-dihydro-5H-dibenzo-[b,e]azepin-5-yl]methyl}-1,3-thiazole-4-carboxylic acid (75)

a) Alkylation of 5 g (15.46 mmol) of tert-butyl (6-oxo-6,11-dihydro-5H-dibenzo[b,e]azepin-11-yl acetate (4) with bromoacetonitrile in analogy to 1 afforded 5.5 g of a brownish oil (ESI-MS [M+H$^+$]=363.15), which was reacted directly with $H_2S$ in pyridine with addition of triethylamine to give a thioamide. The crude product obtained after workup was stirred with n-pentane (7 g).
b) Reaction of the thioamide (4 g; 10.1 mmol) with ethyl bromopyruvate in 30 ml with the addition of 0.83 g of KHCO$_3$ led to ethyl 2-{[11-(2-tert-butoxy-2-hydroxypropyl)-6-oxo-6,11-dihydro-5H-dibenzo[b,e]azepin-5-yl]methyl}-1,3-thiazole-4-carboxylate (4.1 g; ESI-MS [M+H$^+$]=493.15), of which 3 g were hydrolyzed with KOH in dioxane/$H_2O$ (2 g; ESI-MS [M+H$^+$]=465.15).

Examples I.B

Examples of the Synthesis of Compounds of the Formula I (B—G—L)

Example I.B.1

6-Oxo-5-(2-oxo-2-{[2—(2-pyridinylamino)ethyl]amino}ethyl]11-dihydro-5H-dibenzo[b,e]azepin-11-yl acetate (15)

a) 11-(2-Methoxy-2-oxoethyl)-6-oxo-6,11-dihydro-5H-dibenzo-[b,e]azepin-5-yl acetate 3 (0.45 g; 1.33 mmol)

was dissolved in 25 ml of $CH_2Cl_2$ and, at 0° C., 1.1 eq. of N'-(dimethylaminopropyl)-N-ethylcarbodiimide (0.28 g) and 1.03 eq. of N-methylmorpholine (0.15 ml) were added. After about 40 min., N-(2-pyridinyl)-1,2-ethanediamine (0.18 g; 1.33 mmol) was added and the mixture was stirred at RT. After the reaction was complete (about 2 h), the mixture was diluted with $CH_2Cl_2$, washed with saturated NaCl solution, dried and concentrated. The remaining residue (0.49 g) was purified by chromatography on silica gel ($CH_2Cl_2/CH_3OH$ 3 to 10%).

0.36 g; ESI-MS [M+H+]459.

b) Methyl [6-oxo-5-(2-oxo-2-{[2-(2-pyridinylamino)ethyl]-amino}ethyl)-6,11-dihydro-5H-di-benzo[b,e]azepin-11-yl-]acetate (0.34 g; 0.74 mmol) was dissolved in 15 ml of $CH_3OH$ and 2 ml of $H_2O$ and, after addition of a total of 2 eq. of KOH (0.085 g), heated to reflux. After the reaction was complete, the mixture was evaporated, and the resulting crude product was purified by MPLC (silica gel: Bischoff Prontoprep 60–2540-C18E, 32 μm; eluent: $CH_3CN/H_2O$+0.1% acetic acid) and then lyophilized.

0.11 g; ESI-MS [M+H$^+$]=445.1;

$^1$H-NMR (200 MHz; DMSO-d6) diastereomer mixture: δ (ppm) 8.3 (m, 1H), 7.95 (m, 1H), 7.65–7.1 (m, 9H), 6.65–6.30 (m, 3H), 4.8–4.2 (m, 4H), 3.55–3.1 (m, 4H), 3.85 (1H).

Example I.B.2

6-Oxo-5-{2-oxo-2-[4-(2-pyridinyl)-1-piperazinyl]ethyl}-6,11-dihydro-5H-dibenzo[b,e]azepin-11-yl acetate (16)

a) 11-(2-Methoxy-2-oxoethyl)-6-oxo-6,11-dihydro-5H-dibenzo[b,e]-azepin-5-yl acetate 3 (1.2 g; 3.54 mmol) was dissolved in 25 ml of $CH_2Cl_2$ and, at 0° C., 1.1 eq. of N'-(dimethylaminopropyl)-N-ethylcarbodiimide (0.8 g) and 1.0 eq. of DIPEA (ethyldiisopropylamine) (0.45 g) and, after about 2 h, N-(2-pyridinyl)piperazine (0.57 g; 3.54 mmol) were added. The mixture was then stirred at RT. After the reaction was complete (about 2 h), the mixture was diluted with $CH_2Cl_2$, washed with saturated NaCl solution, dried and concentrated. The remaining residue (2.03 g) was purified by chromatography on silica gel ($CH_2Cl_2/CH_3OH$ 2 to 8%).

0.57 g; ESI-MS [M+H$^+$]=485.25;

b) Methyl (6-oxo-5-{2-oxo-2-[4-(2-pyridinyl)-1-piperazinyl]-ethyl}-6, 1-dihydro-5H-dibenzo-[b,e]azepin-1'-yl)acetate (0.485 g; 1.18 mmol) was dissolved in 30 ml of 5:1 dioxane/$H_2O$ and, after addition of 1.5 eq. of KOH (0.1 g), heated to reflux. After the reaction was complete, the mixture was evaporated, and the resulting crude product was purified by MPLC (silica gel: Bischoff Prontoprep 60–2540-C18E, 32 μm; eluent: $CH_3CN/H_2O$+ 0.1% acetic acid) and then lyophilized.

0.21 g; ESI-MS [M+H$^+$]=471.15;

$^1$H-NMR (200 MHz; DMSO-d6) diastereomer mixture: δ (ppm) 12.2–11.8 (broad, 1H), 8.15 (m, 1H), 7.7–7.05 (m, 9H), 6.85 (m, 1H), 6.7 (m, 1H), 5.25–4.25 (4H), 3.75–3 (m, overlapped by $H_2O$), 2.85 (m, 1H).

Example I.B.3

5-[2-({[6-(1H-Benzimidazol-2-yl)-3-pyridinyl]methyl}amino)-2-oxoethyl]-6-oxo-6,11-dihydro-5H-dibenzo[b,e]azepin-11-yl acetate (17)

11-(2-Methoxy-2-oxoethyl)-6-oxo-6,11-dihydro-5H-dibenzo[b,e]-azepin-5-yl acetate 3 (0.56 g; 1.66 mmol) was dissolved in 15 ml of $CH_2Cl_2$ and, at 0° C., 1.2 eq. of N'-(dimethylaminopropyl)-N-ethylcarbodiimide (0.37 g) and 4.4 eq. of DIPEA (0.95 g) were added. After about 50 minutes, 6-(1H-benzimidazol-2-yl)-3-pyridinyl]methanamine×2TFA (6) (0.94 g; 1.66 mmol)—dissolved in 15 ml of DMF—was added and stirred at RT. After the reaction was complete (about 2 h), the mixture was diluted with $CH_2Cl_2$, washed with saturated NaCl solution, dried and concentrated. The resulting crude product (1.4 g) was reacted directly without further purification.

ESI-MS [M+H$^+$]=546.25.

Methyl {5-[2-({[6-(1H-benzimidazol-2-yl)-3-pyridinyl]methyl}-amino)-2-oxoethyl]-6-oxo-6,11-dihydro-5H-dibenzo[b,e]azepin-11-yl}acetate (1.4 g) was dissolved in 30 ml of 5:1 dioxane/$H_2O$ and, after addition of 2.15 eq. of KOH (0.2 g), heated to reflux. After the reaction was complete (12 h), the mixture was evaporated, and the resulting crude product was purified by MPLC (silica gel: Bischoff Prontoprep 60–2540-C18E, 32 μm; eluent: $CH_3CN/H_2O$+0.1% acetic acid) and then lyophilized.

0.45 g; ESI-MS [M+H+]532.15

$^1$H-NMR (200 MHz; DMSO-d6) diastereomer mixture: δ (ppm) 12.9 (s, 1H), 8.95 (m, 1H), 8.70 (m, 1H), 8.30 (m, 1H), 7.85 (m, 1H), 7.8–7.05 (m 12H), 4.85–4.25 (m, 4H), 3.75–3.0 (m, overlapped by $H_2O$), 2.90 (m, 1H).

The following were prepared analogously:

Example I.B.4

10-Oxo-11-[2-oxo-2-({4-[(2-pyridinylamino)methyl]benzyl}amino)-ethyl]-10,11-dihydro-5H-dibenzo[a,d]cyclohepten-5-yl acetate (18)

Coupling with N-[4-(aminomethyl)benzyl]-2-pyridinamine (12) and subsequent hydrolysis of the methyl ester afforded 0.3 g;

ESI-MS [M+H$^+$]=521.25;

$^1$H-NMR (200 MHz; DMSO-d6) diastereomer mixture: δ (ppm) 8.70 (m, 1H), 7.95 (m, 1H), 7.70–6.95 (m, 15H), 6.45 (m, 2H), 4.85–4.2 (m 8H), 2.8 (m 1H).

Example I.B.5

5-(2-{[2-(4,5-Dihydro-1H-imidazol-2-ylamino)ethyl]amino}-2-oxoethyl)-6-oxo-6,11-dihydro-5H-dibenzo[b,e]azepin-11-yl acetate (19)

Coupling with N$^1$-(4,5-dihydro-1H-imidazol-2-yl)-1,2-ethanediamine and subsequent hydrolysis of the methyl ester afforded 0.42 g;

ESI-MS [M+H$^+$]=436.1;

Example I.B.6

2-{5-[({[11-(Carboxymethyl)-6-oxo-6,11-dihydro-5H-dibenzo[b,e]25 azepin-5-yl]acetyl}amino)methyl]-2-pyridinyl}-4,5-dihydro-1H-imidazol-1-ium acetate (20)

Coupling with 2-[5-(aminomethyl)-2-pyridinyl]-4,5-dihydro-1H-imidazole and subsequent hydrolysis of the methyl ester afforded 0.3 g as acetate;

ESI-MS [M+H$^+$]=502.15;

$^1$H-NMR (200 MHz; DMSO-d6) diastereomer mixture: δ (ppm) 9.15–8.80 (m, 2H), 8.65 (m, 1H), 8,1–7.05 (m 10H), 4.8–3.75 (m, overlapped by H$_2$O), 3.4 (m 2H), 2.80 (m, 2H), 1.85 (s, 3H).

Example I.B.7

6-Oxo-5-[2-oxo-2-({[1-(2-pyridinyl)-4-piperidinyl]methyl}amino)-ethyl]-6,11-dihydro-5H-dibenzo[b,e]azepin-11-yl acetate (21)

Coupling with [1-(2-pyridinyl)-4-piperidinyl]methanamine and subsequent hydrolysis of the methyl ester afforded 0.4 g;

ESI-MS [M+H$^+$]499.25;

$^1$H-NMR (200 MHz; DMSO-d6) diastereomer mixture: δ (ppm) 12.15 (broad), 8.2 (m 1H), 8.15 (m 1H), 7.75–7.05 (m, 9H), 6.85 (m 1H), δ 6.6 (m, 1H), 4.8–4.2 (m 4–5H), 3.65–2.7 (m, overlapped by H$_2$O), 1.70 (m 3H), 1.2 (m, 2H).

Example I.B.8

2-[({[11-(Carboxymethyl)-6-oxo-6,11-dihydro-5H-dibenzo[b,e]10 azepin-5-yl]acetyl}amino)methyl]-1H-benzimidazol-1-ium acetate (22)

Coupling with 1H-benzimidazol-2-ylmethanamine and subsequent hydrolysis of the methyl ester afforded 0.48 g as acetate;

ESI-MS [M+H$^+$]=455.15;

$^1$H-NMR (200 MHz; DMSO-d6) diastereomer mixture: δ (ppm) 12.1 broad, 8.95 (m 1H), 7.75–7.05 (m 12H), 4.85–4.30 (m, 6H), 2.85 (m 1H), 1.95 (s, 3H).

Example I.B.9

2-[({(11-(Carboxymethyl)-6-oxo-6,11-dihydro-5H-dibenzo[b,e]-azepin-5-yl}acetyl}amino)methyl]-3H-imidazo[4,5-b]pyridin-3-ium acetate (23)

Coupling with 2-(aminomethyl)-3H-imidazo[4,5-b]pyridine and subsequent hydrolysis of the methyl ester afforded 0.24 g as acetate;

ESI-MS [M+H$^+$]=456.15;

$^1$H-NMR (200 MHz; DMSO-d6) diastereomer mixture: δ (ppm) 9.8/9.25 (broad), 8.25 (m 1H), 7.95 (m 1H), 7.65–6.8 (m 8–9H), 4.75–4.40 (m 4H), 4.0–2.9 (m, overlapped by H$_2$O), 1.80 (s, 3H).

Example I.B.10

6-Oxo-5-(3-oxo-3-{[2-(2-pyridinylamino)ethyl]amino}propyl)-6,11-dihydro-5H-dibenzo[b,e]azepin-11-yl acetate (24)

Coupling of 3-[11-(2-tert-butoxy-2-oxoethyl)-6-oxo-6,11-dihydro 5H-dibenzo[b,e]azepin-5-yl]propanoic acid (6), subsequent cleavage of the tert-butyl ester with TFA and purification by MPLC afforded 40 mg;

ESI-MS [M+H$^+$]459.15;

$^1$H-NMR (200 MHz; DMSO-d6) diastereomer mixture: δ (ppm) 8.15 (in 1H), 7.95 (m 1H), 7.70–7.15 (m, 1H), 6.65 (broad, 1H), 6.45 (m 2H), 4.70 (m 1H), 4.40 (m 2H), 4.25–2.6 (m, overlapped by H$_2$O).

Example I.B.11

6-Oxo-5-{3-oxo-3-[4-(2-pyridinyl)-1-piperazinyl]propyl}-6,11-dihydro-5H-dibenzo[b,e]azepin-11-yl acetate (25)

85 mg were obtained in analogy to Example 10;

ESI-MS [M+H+)=485.25;

$^1$H-NMR (200 MHz; DMSO-d6) diastereomer mixture: δ (ppm)) 8.15 (m, 1H), 7.5–7.05 (m 9H), 6.85 (m 1H), 6.70 (m 1H), 4.85–3.85 (m, 4H), 3.65–3.15 (m, overlapped by H$_2$O), 3.05–2.7 (m 3H).

Example I.B.12

{5-[3-({[4-(1H-Benzimidazol-2-yl)-2-thienyl]methyl}amino)-3-oxopropyl]-6-oxo-6,11-dihydro-5H-dibenzo[b,e]azepin-11-yl}-acetic acid (26)

20 mg were obtained in analogy to Example 10;

ESI-MS [M+H$^+$]=551.15;

$^1$H-NMR (200 MHz; DMSO-d6) diastereomer mixture: δ (ppm) 12.2 (broad), 8.70 (m 1H), 8.10 (m, 1H), 7.80–6.95 (m, 13H), 4.70 (m 1H), 4.60–3.90 (m, 5H), 3.55–2.85 (m, overlapped by H$_2$O).

Example I.B.14

2-{[(1-{[11-(Carboxymethyl)-6-oxo-6,11-dihydro-5H-dibenzo-[b,e]azepin-5-yl]acetyl}-4-piperidinyl)methyl]amino}pyridinium acetate (28)

Coupling with N-(4-piperidinylmethyl)-2-pyridinamine and subsequent hydrolysis of the methyl ester afforded 65 mg;

ESI-MS [M+H$^+$]=499.25;

$^1$H-NMR (200 MHz; DMSO-d6) diastereomer mixture: δ (ppm) 8.05 (m, 1H), 7.80–7.15 (m, 9H), 6.70 (m, 1H), 6.55 (m, 2H), 5.35–4.80 (m 3H), 4.70–4.0 (m, 3H), 3.75–2.80 (m, overlapped by H$_2$O), 2.05 (s, 3H), 2.80 (m, 3H), 1.25 (m 2H).

Example I.B.15

5-(2-{4-[(Benzylamino)carbonyl]-1-piperazinyl}-2-oxoethyl)-6-oxo-6,11-dihydro-5H-dibenzo[b,e]azepin-11-yl acetate (29)

a) 11-(2-Methoxy-2-oxoethyl)-6-oxo-6,11-dihydro-5H-dibenzo[b,e]-azepin-5-yl acetate 3 (2.5 g; 7.37 mmol) was dissolved in 40 ml of CH$_2$Cl$_2$ and "preactivated"—as described above—by adding 1.2 eq. of N'-(dimethylaminopropyl)-N-ethylcarbodiimide (1.15 g) and 1.2 eq. of DIPEA (1.15 g). After 1 h, Boc-piperazine (1.37 g) was added, and the mixture was stirred at 0° C. for 1 h and then at RT. For workup, the mixture was diluted with $CH_2Cl_2$, washed with saturated NaCl solution, dried and concentrated. The resulting crude product (3.2 g) was purified by chromatography on silica gel ($CH_2Cl_2/CH_3OH$ 1 to 3%+0.1% acetic acid).

1.7 g; ESI-MS [M+H+]=508.2;

b) 5-{2-[4-(tert-Butoxycarbonyl)-1-piperazinyl]-2-oxoethyl}-6-oxo-6,11-dihydro-5H-dibenzo[b,e]azepin-11-yl acetate (1.7 g) was dissolved in 20 ml of $CH_2Cl_2$ and, at 0° C., 10 ml of TFA were added. After the reaction was complete, the mixture was concentrated and coevaporated 2× with toluene (1.75 g; ESI-MS [M+H+]=408.15).

The TFA salt was then dissolved in 30 ml of 1:1 toluene/dioxane and, after addition of 2 eq. of DIPEA (0.4 g) and 1 eq. of benzyl isocyanate (0.2 g), heated to reflux. After the reaction was complete, the mixture was concentrated, taken up in $CH_2Cl_2$, washed with 1N HCl solution and then saturated NaCl solution, dried and evaporated (0.81 g; ESI-MS [M+H+]=541.25). Hydrolysis was effected by dissolving in 25 ml of 2:1 dioxane/$H_2O$, adding 1.5 eq. of KOH (0.13 g) and heating to reflux. The mixture was then concentrated, acidified with 2N HCl and extracted 2× with $CH_2Cl_2$. The combined organic phases were then washed with saturated NaCl solution, dried and again concentrated, and the resulting residue was stirred with methyl tert-butyl ether.

0.36 g; ESI-MS [M+H+]=527.15;

$^1$H-NMR (200 MHz; DMSO-d6) diastereomer mixture: δ (ppm) 7.7–7.1 (m, 14H), 5.25–4.1 (4H), 3.7–3.1 (m, overlapped by $H_2O$), 2.95 (m, 1H).

Example I.B.16

5-[2-({[5-(1H-Benzimidazol-2-yl)-2-thienyl]methyl}amino)-2-oxoethyl]-6-oxo-6,11-dihydro-5H-dibenzo[b,e]azepin-11-yl acetate (30)

a) 11-(2-Methoxy-2-oxoethyl)-6-oxo-6,11-dihydro-5H-dibenzo-[b,e]azepin-5-yl acetate 3 (4 g; 11.8 mmol) was dissolved in 30 ml of $CH_2Cl_2$ and "preactivated"—as described above—by adding 1.15 eq. of N'-(dimethylaminopropyl)-N-ethylcarbodiimide (2.6 g) and 1.6 eq. of DIPEA (2.5 g). After 1 h, 5-(aminomethyl)-3-thiophenecarbonitrile (1.92 g)—dissolved in 35 ml of DMF—and a further 1 ml of DIPEA were added, and the mixture was stirred at 0° C. for 1 h and then at RT. The usual workup afforded 6.6 g of yellow oil which was purified by chromatography on silica gel ($CH_2Cl_2/CH_3OH$ 1 to 3%). 4.1 g; ESI-MS [M+H+]=460.15;

b) Methyl [10-(2-{[(5-cyano-2-thienyl)methyl]amino}-2-oxoethyl)-11-oxo-10,11-dihydro-5H-dibenzo[a,d]cyclohepten-5-yl]acetate (0.85 g; 1.85 mmol) was dissolved in 15 ml of pyridine and, at 0° C., 1.76 g of triethylamine were added, and $H_2S$ was passed in for 90 minutes. After 1 h at RT, the reaction mixture was concentrated, and $CH_2Cl_2$ was added and reevaporated 2× (0.9 g of yellow foam).

The thioamide was then dissolved in 20 ml of $CH_2Cl_2$ and, after addition of 5 eq. of $CH_3I$ (1.3 g), stirred at RT overnight. The mixture was evaporated, and the residue was taken up in 25 ml of $CH_3OH$, mixed with 1,2-phenylenediamine (0.197 g) and stirred at RT for 3 h. Concentration of the mixture afforded 1.35 g of crude product which was purified by chromatography on silica gel ($CH_2Cl_2/CH_3OH$). 0.46 g; ESI-MS [M+H+]=551.15.

Hydrolysis of the methyl ester took place in analogy to the examples already described in 20 ml of 3:1 dioxane/$H_2O$ with 80 mg of KOH at RT. Workup and purification of the crude product by MPLC (silica gel: Bischoff Prontoprep 60–2540-C18E, 32 μm; eluent: $CH_3CN/H_2O$+0.1% acetic acid) afforded 0.22 g of the required product.

ESI-MS [M+H+]=537.15;

$^1$H-NMR (200 MHz; DMSO-d6) diastereomer mixture: δ (ppm) 8.85 (m, 1H), 7.75–7.2 (m, 14H), 4.85–4.3 (m, 6H), 3.5–3.1 (m, overlapped by $H_2O$), 2.95 (m, 1H).

Example I.B.17

(5-{2-[({4-[Amino(imino)methyl]-2-thienyl}methyl)amino]-2-oxoethyl}-6-oxo-6,11-dihydro-5H-dibenzo[b,e]azepin-11'-yl)acetic acid (31)

Methyl-[5-(2-{[(4-cyano-2-thienyl)methyl]amino}-2-oxoethyl)-6-oxo-6,11-dihydro-5H-di-benzo-[b,e]azepin-11-yl]acetate and the corresponding thioamide were prepared in analogy to Example 16. Methyl {5-[2-({[4-(thiocarbamoyl)-2-thienyl]methyl}amino)-2-oxoethyl]-6-oxo-6,11-dihydro-5H-dibenzo[b,e]azepin-11-yl}acetate (2.3 g; 4.66 mmol) in 30 ml of $CH_2Cl_2$ was stirred with 5 eq. of $CH_3I$ (3.3 g) at RT overnight. The mixture was evaporated, and the residue was taken up in 20 ml of $CH_3OH$, mixed with 0.27 g of ammonium acetate and again stirred overnight. Concentration of the mixture afforded 1.44 g of the crude product (ESI-MS [M+H+]=477.15).

The methyl ester was taken up in 10 ml of dioxane and, after addition of 15 ml of 2N HCl refluxed for 6 h. The mixture was then evaporated, and the resulting residue was purified by MPLC (silica gel: Bischoff Prontoprep 60–2540-C18E, 32 μm; eluent: $CH_3CN/H_2O$+0.1% acetic acid).

0.12 g; ESI-MS [M+H$^+$]=463.05;

$^1$H-NMR (200 MHz; DMSO-d6) diastereomer mixture: δ (ppm) 10.5–9.1 (broad), 9.05/8.8 (m, 1H), 8.35 (m, 1H), 7.7–7.0 (m, 10H), 4.95–4.15 (m, 6H), 3.6–2.90 (m, overlapped by $H_2O$), 2.70 (m, 1H).

Example I.B.18

{5-[2-({[4-(1H-Benzimidazol-2-yl)-2-thienyl]methyl}amino)-2-oxoethyl]-6-oxo-6,11-dihydro-5H-dibenzo[b,e]azepin-11-yl}acetic acid (32)

Methyl [5-(2-{[(4-cyano-2-thienyl)methyl]amino}-2-oxoethyl)-6-oxo-6,11-dihydro-5H-dibenzo-[b,e]azepin-11-yl]acetate (0.5 g; 1.09 mmol) in 30 ml of $CH_3OH$ was refluxed with 0.2 ml of sodium methoxide solution (30% in $CH_3OH$) for 7 h. Then 0.2 g of 1,2-phenylenediamine bishydrochloride was added, and the mixture was again refluxed for about 8 h. After the reaction was complete, the mixture was concentrated and the remaining residue was purified by chromatography on silica gel ($CH_2Cl_2/CH_3OH$ 1 to 3%).

0.13 g; ESI-MS [M+H$^+$]=551.15;

Hydrolysis in 15 ml of 3:1 dioxane/$H_2O$ with 1.5 eq. of KOH (0.02 g) and purification of the crude product by MPLC (silica gel: Bischoff Prontoprep 60-2540-C18E, 32 μm; eluent: $CH_3CN/H_2O$+0.1 acetic acid).

0.03 g; ESI-MS [M+H$^+$]=537.15;

¹H-NMR (200 MHz; DMSO-d6) diastereomer mixture: δ (ppm) 9.0/8.8 (m, 1H), 8.15 (m, 1H), 7.75–7.0 (m, 14H), 4.85–4.20 (m, 6H), 3.75–2.8 (m, overlapped by H₂O).

Example I.B.19

{5-[2-({[4-(3H-Imidazo[4,5-b]pyridin-2-yl)-2-thienyl]methyl}-amino)-2-oxoethyl]-6-oxo-6,11-dihydro-5H-dibenzo[b,e]azepin-11-yl}acetic acid (33)

Analogously by reaction with 2,3-pyridinamine.
32 mg; ESI-MS [M+H⁺]=538.4;
¹H-NMR (200 MHz; DMSO-d6) diastereomer mixture: δ (ppm) 8.95–8.8 (m, 1H), 8.0 (m, 1H), 7.8–7.05 (m, 13H), 4.75–4.1 (m, 6H), 2.95 (m, 1H).

Example I.B.20

[5-(2-{[4-(1H-Benzimidazol-2-yl)benzyl]amino}-2-oxoethyl)-6-oxo-6,11-dihydro-5H-dibenzo[b,e]azepin-11-yl]acetic acid hydrochloride (34)

Analogously by reaction with 4-(1H-benzimidazol-2-yl)benzylmethylamine from building block 14.
40 mg; ESI-MS [M+H⁺]=531.15
¹H-NMR (400 MHz; DMSO-d6) diastereomer mixture: δ (ppm) 8.95–8.8 (m, 1H), 8.0 (m, 1H), 7.8–7.05 (m, 13H), 4.75–4.1 (m, 6H), 2.95 (m, 1H).

Example I.B.21

{5-[2-({[4-(1H-benzimidazol-2-yl)-1,3-thiazol-2-yl]methyl-amino)-2-oxoethyl]-6-oxo-6,11-dihydro-5H-dibenzo[b,e]azepin-11-yl}acetic acid (35)

Analogously by reaction with [4-(1H-benzimidazol-2-yl)-1,3-thiazol-2-yl]methylamine.
430 mg; ESI-MS [M+H⁺]=538.15;
¹H-NMR (360 MHz; DMSO-d6) diastereomer mixture: δ (ppm) 9.4/9.3 (m, 1H), 8.9 (m, 1H), 7.8–7.15 (m, 13H), 4.95–4.35 (m, 5H), 3.2 (m, overlapped by H₂O), 2.95 (m, 1H).

Example I.B.22

(5-(2-(4-(1H-Benzimidazol-2-yl)anilino)-2-oxoethyl)-6-oxo-6,11-dihydro-5H-dibenzo[b,e]azepin-11-yl)acetic acid (36)

Analogously by reaction with 4-(1H-benzimidazol-2-yl)aniline.
100 mg; ESI-MS [M+H⁺]=517.15;
¹H-NMR (360 MHz; DMSO-d6) diastereomer mixture: δ (ppm) 12.75 (broad), 10.6 (m, 1H), 8.2 (m, 2H), 7.9–7.1 (m, 14H), 4.8–4.75 (m, 2H), 4.4 (m, 1H), 3.75–3.0 (m, overlapped by H₂O), 2.8 (m, 1H).

Example I.B.23

Methyl [10-(2-{[4-(1H-benzimidazol-2-yl)benzyl]amino}-2-oxoethyl)-11-oxo-10,11-dihydro-5H-dibenzo[b,e][1,4]diazepin-5-yl]acetate

[5-(2-Methoxy-2-oxoethyl)-11-oxo-5,11-dihydro-10H-dibenzo-[b,e]-[1,4]diazepin-10-yl]acetic acid 37c (0.8 g; 2.35 mmol) was dissolved in 50 ml of DMF and, at 0° C., 1.05 g of HATU and 0.3 g of DIPEA were added, and the mixture was stirred at RT for 30 min. Addition of [4-(1H-benzimidazol-2-yl)phenyl]methanamine bistrifluoracetate from building block 14 (1.06 g; 2.35 mmol) and 0.6 g of DIPEA was followed by stirring at 5° C. for 2 h. The mixture was diluted with CH₂Cl₂, washed with H₂O, dried and concentrated. Chromatography on silica gel (CH₂Cl₂/CH₃OH 1→8%) afforded 1.3 g of a pale brownish oil (ESI-MS [M+H⁺]=546.
¹H-NMR (400 MHz; DMSO-d6): δ (ppm) 8.45 (t, 1H), 8.15 (d, 2H), 7.05–7.7 (m, 16H), 4.75 and 4.65 (each d, 2H), 4.45–4.55 (m, 2H), 3.55 (s, 3H).

Example I.B.24

[10-(2-{[4-(1H-Benzimidazol-2-yl)benzyl]amino}-2-oxoethyl)-11-oxo-10,11-dihydro-5H-dibenzo[b,e][1,4]diazepin-5-yl]acetic acid (acetate)

Methyl [10-(2-{[4-(1H-benzimidazol-2-yl)benzyl]amino}-2-oxoethyl)-11-oxo-10,11-dihydro-5H-dibenzo[b,e][1,4]diazepin-5-yl]acetate (1 g; 1.56 mmol) and 0.15 g of KOH were refluxed in 30 ml of 2:1 dioxane/H₂O for 3 h. Concentration of the mixture and chromatography of the crude product by MPLC (silica gel: Bischoff Prontoprep 60–2540-C₁₈E, 32 μm; eluent: CH₃CN/H₂O+0.1% acetic acid) afforded 0.22 g of the required product as acetate; ESI-MS [M+H⁺]532.
¹H-NMR (400 MHz; DMSO-d₆): δ (ppm) 12.75 (s br, 1H), 8.40 (t, 1H), 8.15 (d, 2H), 7.15–7.7 (m, 16H), 4.75 and 4.60 (each d, 2H), 4.45–4.55 (m, 2H), 2.1 (s, 3H).

Example I.B.25

Methyl [10-(2-{[(2-{[(benzylamino)carbonyl]amino}-1,3-thiazol-4-yl)methyl]amino}-2-oxoethyl)-11-oxo-10,11-dihydro-5H-dibenzo-[b,e][1,4]diazepin-5-yl]acetate Preparation took place in analogy to I.B.23 by reacting [5-(2-methoxy-2-oxoethyl)-11-oxo-5,11-dihydro-10H-dibenzo[b,e]-[1,4]diazepin-10-yl]acetic acid 37c with N-[4-(aminomethyl)1,3-thiazol-2-yl]-N'-benzylurea (hydrochloride) (38). Chromatography on silica gel (CH₂Cl₂/CH₃OH 2→10%) afforded 0.45 g; ESI-MS [M+H⁺]=585.25.

Example I.B.26

[10-(2-{[(2-{[(Benzylamino)carbonyl]amino}-1,3-thiazol-4-yl)-methyl]amino}-2-oxoethyl)-11-oxo-10,11-dihydro-5H-dibenzo-[b,e][1,4]diazepin-5-yl]acetic acid Hydrolysis of the methyl ester in analogy to I.B.24 and purification of the crude product by MPLC afforded 0.11 g; ESI-MS [M+H⁺]=571.25.

Example I.B.27

[10-(2-{[(2-{[Amino(imino)methyl]-[10-(2-{[(2-{[Amino(imino)methyl]amino}-1,3-thiazol-5-yl)methyl]-diazepin-5-yl}acetic acid Reaction in analogy to I.B.23 with [4-(aminomethyl)-1,3-thiazol-2-yl]guanidine (bishydrochloride) (39) afforded 0.09 g;
ESI-MS [M+H⁺]=535.15.

Example I.B.28

[5-(2-{[3-(1H-Imidazol-2-ylamino)-3-oxopropyl]amino}-2-oxoethyl)-6-oxo-6,11-dihydro-5H-dibenzo[b,e]azepin-11-yl]acetic acid a) 440 mg (1.3 mmol) of 11-(2-methoxy-2-oxoethyl)-6-oxo-6,11-dihydro-5H-dibenzo[b,e]-azepin-5-yl acetate (3) were dissolved in 15 ml of DMF, and 0.3 ml of DIPEA and 543 mg of HATU were added. After 30 min at room temperature, 3-amino-N-(1H-imidazol-2-yl)propanamide 42 (200 mg, 1.3 mmol) dissolved in DMF was slowly added dropwise, and the mixture was stirred for 6 h. It was taken up in ethyl acetate and water and shaken 3× with $H_2O$ and 3× with $NaHCO_3$ solution. The organic phase was dried and concentrated, and the remaining residue was dissolved in $CH_2Cl_2/CH_3OH$ 19:1 and precipitated with diethyl ether. The precipitate was filtered off with suction, washed and dried (220 mg). ESI-MS [M+H$^+$]=476.

b) I.B.28a was dissolved in 5 ml of THF, and a solution of 45 mg of LiOH (1.89 mmol) in aqueous solution was added. The mixture was stirred at RT until the reaction was complete and was then acidified with 10% citric acid and concentrated. A white precipitate separated out and was filtered off with suction, washed 4× with $H_2O$ and dried in vacuo (120 mg);
ESI-MS [M+H$^+$]=462.

Example I.B.29

(5-{2-[4-({(Benzylamino)carbonyl]amino}methyl)piperidin-1-yl]-2-oxoethyl}-6-oxo-6,11-dihydro-5H-dibenzo[b,e]azepin-11-yl)acetic acid a) Coupling of 11-(2-Methoxy-2-oxoethyl)-6-oxo-6,11-dihydro-5H-dibenzo[b,e]azepin-5-yl] acetate (3) with N-benzyl-N'-(piperidin-4-ylmethyl)carbamate (THL 31, 47, 1990, 6903) in analogy to Example I.B.1 and subsequent purification afforded 1.65 g, which were then hydrogenated under standard conditions with 5% Pd on active carbon in 20 ml of $CH_3COH$ and addition of 1.35 ml of 2 N HCl (1.04 g).

b) Reaction of the free amine (0.21 g) with 0.06 g of benzyl isocyanate and 0.046 g of N-methylmorpholine in 15 ml of $CH_2Cl_2$ under reflux, washing of the mixture with aqueous 1 N HCl and saturated NaCl solution and concentration afforded 0.17 g of a yellowish oil; ESI-MS [M+H$^+$]=569.25.

C) Hydrolysis of the methyl ester under standard conditions in analogy to I.B.1 and the usual workup afforded 0.16 g as a white solid foam; ESI-MS [M+H$^+$]=555.25.

The following were prepared in analogy to Example I.B.10:

Example I.B.30

6-Oxo-5-(3-oxo-3-{[(1-pyridin-2-ylpiperidin-4-yl)methyl]-amino}propyl)-6,11-dihydro-5H-dibenzo[b,e]azepin-11-yl acetate Coupling of 3-[11-(2-tert-butoxy-2-oxoethyl)-6-oxo-6,11-dihydro-5H-dibenzo[b,e]azepin-5-yl]propanoic acid 6 with [1-(2-pyridinyl)-4-piperidinyl]methanamine, subsequent cleavage of the tert-butyl ester with TFA and purification by MPLC afforded 106 mg; ESI-MS [M+H$^+$]=513.25.

Example I.B.31

5-{3-[({1-[(Benzylamino)carbonyl]piperidin-4-yl}methyl)-amino]-3-oxopropyl}-6-oxo-6,11-dihydro-5H-dibenzo[b,e]azepin-11-yl acetate Coupling with 4-(aminomethyl)-N-benzylpiperidine-1-carboxamide (43), cleavage of the tert-butyl ester with TFA and purification by MPLC afforded 0.46 g; ESI-MS [M+H$^+$]=569.25.

Example I.B.32

5-[3-({[5-(1H-Benzimidazol-2-yl)thien-2-yl]methyl}amino)-3-oxopropyl]-6-oxo-6,11-dihydro-5H-dibenzo[b,e]azepin-11-yl acetate Coupling with [5-(1H-benzimidazol-2-yl)thien-2-yl]methanamine (45), cleavage of the tert-butyl ester with TFA and purification by MPLC afforded 70 mg; ESI-MS [M+H$^+$]=551.15.

Example I.B.33

5-[3-({[4-(1H-Benzimidazol-2-yl)thien-2-yl]methyl}amino)-3-oxopropyl]-6-oxo-6,11-dihydro-5H-dibenzo[b,e]azepin-11-yl acetate Coupling with (4-(1H-benzimidazol-2-yl)thien-2-yl)methanamine (44), cleavage of the tert-butyl ester with TFA and purification by MPLC afforded 20 mg; ESI-MS [M+H$^+$]=551.15.

The following were prepared in analogy to Example I.B.1:

Example I.B.34

5-[2-[({1-[(Benzylamino)carbonyl]piperidin-4-yl]methyl)amino]-2-oxoethyl}-6-oxo-6,11-dihydro-5H-dibenzo[b,e]azepin-11-yl acetate Coupling of 11-(2-methoxy-2-oxoethyl)-6-oxo-6,11-dihydro-5H-dibenzo[b,e]azepin-5-ylacetate (3) with 4-(aminomethyl)-N-benzylpiperidine-1-carboxamide (43), ester cleavage and subsequent purification resulted in 0.42 g as a solid foam;

ESI-MS [M+H$^+$]=555.25.

Example I.B.35

5-(2-{[4-({[(Benzylamino)carbonyl]amino}methyl)benzyl]amino} 2-oxoethyl)-6-oxo-6,11-dihydro-5H-dibenzo[b,e]azepin-11-yl acetate Coupling of 3 with N-[4-(aminomethyl)benzyl]-N'-benzylurea (40), ester cleavage and subsequent purification resulted in 0.62 g as a solid foam.

$^1$H-NMR (DMSO-d6, 400 MHz) diastereomer mixture: δ (ppm) 7.70–7.10 (m, 13H), 6.65–6.5 (m, 2H), 4.75–4.65 (m, 2H), 4.5–4.2 (m, 5H), 3.55, 3.25 (each dd, 1H), 2.0–1.85 (m, 2H).

Example I.B.36

6-Oxo-5-{2-oxo-2-[4-(pyridin-2-ylamino)piperidin-1-yl]ethyl}-6,11-dihydro-5H-dibenzo[b,e]azepin-11-yl acetate Coupling of 3 with 2-(piperidin-4-ylamino)pyridine (46), ester cleavage and subsequent purification resulted in 0.3 g as a solid foam; ESI-MS [M+H$^+$]=485.15.

Example I.B.37

5-(2-{[4-(1H-Benzimidazol-2-ylamino)benzyl]amino}-2-oxoethyl)-6-oxo-6,11-dihydro-5H-dibenzo[b,e]azepin-11-yl acetate Coupling of 11-(2-tert-butoxy-2-oxoethyl)-6-oxo-6,11-dihydro-5H-dibenzo[b,e]azepin-5-yl acetate (66) with N-[4-(aminomethyl)-phenyl]-1H-benzimidazol-2-amine (hydrochloride) (47) using HATU as coupling reagent, ester cleavage with TFA and purification of the crude product by MPLC afforded 0.4 g; ESI-MS [M+H$^+$]=546.25.

Example I.B.38

Methyl-[5-(2-{[4-(1H-benzimidazol-2-ylamino)benzyl]amino}-2-oxoethyl)-6-oxo-6,11-dihydro-5H-dibenzo[b,e]azepin-11-yl acetate 5-(2-{([4-(1H-Benzimidazol-2-ylamino)benzyl]amino}-2-oxoethyl)-6-oxo-6,11-dihydro-5H-dibenzo[b,e]azepin-11-ylacetate I.B.37(0.9 g; 0.16 mmol) was suspended in 5 ml of CH$_3$OH and, after dropwise addition of 0.02 ml of SOCl$_2$, stirred at RT for 48 h. For workup, the reaction mixture was evaporated and stirred with n-pentane (40 mg); ESI-MS [M+H$^+$]=560.25.

Example I.B.39

5-(2-{[5-(1H-Benzimidazol-2-ylamino)pentyl]amino}-2-oxoethyl)-6-oxo-6,11-dihydro-5H-dibenzo[b,e]azepin-11-yl acetate Coupling of 3 with N$^1$-(1H-benzimidazol-2-yl)pentane-1,5-diamine (hydrochloride) (48) using HATU as coupling reagent, cleavage of the methyl ester in analogy to Example I.B.1 and filtration of the resulting crude product through a Chromabond C$_{18}$ cartridge afforded 0.24 g; ESI-MS [M+H$^+$]=525.6.

Example I.B.40

5-(2-{[4-(1H-Benzimidazol-2-ylamino)butyl]amino}-2-oxoethyl)-6-oxo-6,11-dihydro-5H-dibenzo[b,e]azepin-11-yl acetate Coupling of 11-(2-tert-butoxy-2-oxoethyl)-6-oxo-6,11-dihydro-5H-dibenzo[b,e]azepin-5-ylacetate (66) with N$^1$-(1H-benzimidazol-2-yl)butane-1,4-diamine (trifluoroacetate) (49) using HATU as coupling reagent, cleavage of the tert-butyl ester and purification of the resulting crude product by RP-MPLC afforded 94 mg; ESI-MS [M+H$^+$]=512.25.

Example I.B.41

5-{2-[(3-{[(Benzylamino)carbonyl]amino}benzyl)amino]-2-oxoethyl}-6-oxo-6,11-dihydro-5H-dibenzo[b,e]azepin-11-yl acetate Coupling of 11-(2-tert-butoxy-2-oxoethyl)-6-oxo-6,11-dihydro-5H-dibenzo[b,e]azepin-5-yl acetate (66) with (3-{[(benzylamino)-carbonyl]amino}phenyl)methanamine (hydrochloride) (41), TFA cleavage and stirring of the resulting crude product with methyl tert-butyl ether/CH$_3$OH 19:1 afforded 0.61 g of slightly brownish solids; ESI-MS [M+H$^+$]=563.25.

Example I.B.42

5-(2-{4-[(1H-Benzimidazol-2-ylamino)methyl]piperidin-1-yl}-2-oxoethyl)-6-oxo-6,11-dihydro-5H-dibenzo[b,e]azepin-11-yl acetate Coupling of 11-(2-tert-butoxy-2-oxoethyl)-6-oxo-6,11-dihydro-5H-dibenzo[b,e]azepin-5-ylacetate (66) with N-(piperidin-4-ylmethyl)-1H-benzimidazol-2-amine (trifluoroacetate) (50), TFA cleavage and chromatography by RP-MPLC afforded 60 mg; ESI-MS [M+H$^+$]=538.25.

Example I.B.43

6-Oxo-5-[2-oxo-2-({[2-(pyridin-2-ylamino)-1,3-thiazol-4-yl]-methyl}amino)ethyl]-6,11-dihydro-5H-dibenzo[b,e]azepin-11-yl acetate Coupling of 11-(2-tert-butoxy-2-oxoethyl)-6-oxo-6,11-dihydro-5H-dibenzo[b,e]azepin-5-yl acetate (66) with N-[4-(aminomethyl)-1,3-thiazol-2-yl]pyridin-2-amine (bishydrochloride) (51), TFA cleavage and chromatography by RP-MPLC afforded 65 mg;
ESI-MS [M+H$^+$]=514.15.

Example I.B.44

6-Oxo-5-[2-oxo-2-({[2-(pyridin-2-ylamino)-1,3-thiazol-5-yl]-methyl}amino)ethyl]-6,11-dihydro-5H-dibenzo[b,e]azepin-11-yl acetate Coupling of 11-(2-tert-butoxy-2-oxoethyl)-6-oxo-6,11-dihydro-5H-dibenzo[b,e]azepin-5-ylacetate (66) with N-[5-(aminomethyl)-1,3-thiazol-2-yl]pyridin-2-amine (bishydrochloride) (52), TFA cleavage and chromatography by RP-MPLC afforded 170 mg; ESI-MS [M+H$^+$]=514.15.

Example I.B.45

5-(2-{[(2-{[Amino(imino)methyl]amino}-1,3-thiazol-4-yl)methyl]-amino}-2-oxoethyl)-6-oxo-6,11-dihydro-5H-dibenzo[b,e]azepin-11-yl acetate (trifluoroacetate)

Coupling of 11-(2-tert-butoxy-2-oxoethyl)-6-oxo-6,11-dihydro-5H-dibenzo[b,e]azepin-5-yl acetate (66) with [4-(aminomethyl)-1,3-thiazol-2-yl]guanidine (bishydrochloride) (39), TFA cleavage and chromatography by RP-MPLC afforded 25 mg; ESI-MS [M+H$^+$]=479.15.

Example I.B.46

5-(2-{[(2-{[Amino(imino)methyl]amino}-1,3-thia-zol-5-yl)-methyl]amino}-2-oxoethyl)-6-oxo-6,11-dihydro-5H-dibenzo[b,e]-azepin-11-yl acetate Coupling of 11-(2-tert-Butoxy-2-oxoethyl)-6-oxo-6,11-dihydro-5H-dibenzo[b,e]-azepin-5-yl acetate (66) with N-[5-(aminomethyl)-1,3-thiazol-2-yl]guanidine (dihydrochloride) (53) and TFA cleavage afforded 70 mg; ESI-MS [M+H$^+$]=479.15.

Example I.B.47

5-[2-({2-[4-(1H-Benzimidazol-2-yl)phenyl]ethyl}amino)-2-oxo-ethyl]-6-oxo-6,11-dihydro-5H-dibenzo[b,e]azepin-11-yl acetate Coupling of 11-(2-tert-butoxy-2-oxoethyl)-6-oxo-6,11-dihydro-5H-dibenzo[b,e]azepin-5-yl acetate (66) with 2-[4-(1H-benzimidazol-2-yl)phenyl]ethanamine from building block 54 and TFA cleavage afforded 35 mg; ESI-MS [M+H$^+$]=545.25.

Example I.B.48

6-Oxo-5-{2-oxo-2-[({4-[(pyridin-2-ylamino)methyl]thien-2-yl}-methyl)amino]ethyl}-6,11-dihydro-5H-dibenzo[b,e]azepin-11-yl acetate Coupling of 11-(2-tert-butoxy-2-oxoethyl)-6-oxo-6,11-dihydro-5H-dibenzo[b,e]azepin-5-ylacetate (66) with N-{[5-(aminomethyl)-thien-3-yl]methyl}pyridin-2-amine (trifluoroacetate) (55) and TFA cleavage afforded 170 mg; ESI-MS [M+H$^+$]=527.25.

Example I.B.49

5-(2-{methyl-[2-(pyridin-2-ylamino)ethyl]amino}-2-oxoethyl)-6-oxo-6,11-dihydro-5H-dibenzo[b,e]azepin-11-yl acetate Coupling of 11-(2-tert-butoxy-2-oxoethyl)-6-oxo-6,11-dihydro-5H-dibenzo[b,e]-azepin-5-ylacetate (66) with N$^1$-methyl-N$^2$-pyridin-2-ylethane-1,2-diamine (acetate) (56), TFA cleavage and RP-MPLC afforded 130 mg; ESI-MS [M+H$^+$]=459.25.

Example I.B.50

6-Oxo-5-(2-oxo-2-[4-(2-pyridinylamino)benzyl]amino}ethyl)-6,11-dihydro-5H-dibenzo[b,e]azepin-11-yl acetate Coupling of 3 with N-[4-(aminomethyl)phenyl]-2-pyridinamine (57), cleavage of the methyl ester in analogy to Example I.B.1 and filtration of the resulting crude product through a Chromabond C$_{18}$ cartridge afforded 3 mg; ESI-MS [M+K$^+$]=545.3, [M+H$^+$]=507.2, 326.0, 254.1.

Example I.B.51

Methyl (5-{2-[(4-{[(benzylamino)carbonyl]amino}benzyl)amino]-2-oxoethyl}-6-oxo-6,11-dihydro-5H-dibenzo[b,e]azepin-11-yl) acetate Coupling of 3 with N-[4-(aminomethyl)phenyl]-N'-benzylurea (trifluoroacetate) (58) and purification of the crude product by chromatography on silica gel afforded 550 mg; ESI-MS [M+K$^+$]=615.2, [M+H$^+$]: 577.35.

Example I.B.52

(5-{2-[(4-{[(Benzylamino)carbonyl]amino}benzyl)amino]-2-oxoethyl}-6-oxo-6,11-dihydro-5H-dibenzo[b,e]azepin-11-yl)acetic acid Hydrolysis of the methyl ester from I.B.51 in analogy to I.B.1 and purification of the crude product by RP-MPLC afforded 174 mg;
ESI-MS [M+K$^+$]=601.25, [M+H$^+$]: 563.35.

Example I.B.53

{4-[({[11-(Carboxymethyl)-6-oxo-6,11'-dihydro-5H-dibenzo[b,e]45 azepin-5-yl]acetyl}amino)methyl]anilino}(imino)methanamine (trifluoroacetate)

Coupling of 11-(2-tert-butoxy-2-oxoethyl)-6-oxo-6,11-dihydro-5H-dibenzo[b,e]azepin-5-ylacetate (66) with [4-(aminomethyl) phenyl]guanidine (bishydrochloride) (59), TFA cleavage and purification of the crude product by RP-MPLC afforded 7.8 mg;
ESI-MS [M+K$^+$]=510.1, [M+H$^+$]=472.15.

Example I.B.54

[5-(2-{[4-(5-Chloro-1H-benzimidazol-2-yl)benzyl]amino}-2-oxo-ethyl)-6-oxo-6,11-dihydro-5H-dibenzo[b,e]azepin-11-yl]acetic acid Coupling of 3 with [4-(5-chloro-1H-benzimidazol-2-yl)phenyl]-methanamine (trifluoroacetate) (60) and cleavage of the methyl ester in analogy to I.B.1 afforded 25 mg; ESI-MS [M+H$^+$]: 565.25.

Example I.B.55

[5-(2-{[4-(5,6-Dimethyl-1H-benzimidazol-2-yl)benzyl]amino}-2-oxoethyl)-6-oxo-6,11-dihydro-5H-dibenzo[b,e]azepin-11-yl]acetic acid Coupling of 3 with [4-(5,6-dimethyl-1H-benzimidazol-2-yl)phenyl]methanamine (trifluoroacetate) (61) and cleavage of the methyl ester in analogy to Example I.B.1 afforded 100 mg; ESI-MS [M+H$^+$]: 559.25.

Example I.B.56

[6-Oxo-5-(2-oxo-2-{[3-(2-pyridinylamino)propyl]amino}ethyl)-6,11-dihydro-5H-dibenzo[b,e]azepin-11-yl]acetic acid Coupling of 3 with N$^1$-(2-pyridinyl)-1,3-propanediamine (68) and cleavage of the methyl ester in analogy to Example I.B. afforded 8 mg; ESI-MS [M+H$^+$]: 459.25.

Example I.B.57

Methyl [6-oxo-5-(2-oxo-2-{4-[2-(2-pyridinylamino) ethyl]-1-piperidinyl}ethyl)-6,11-dihydro-5H-dibenzo [b,e]azepin-11-yl]-acetate Coupling of 3 with N-[2-(4-piperidinyl)ethyl]-2-pyridinamine (trifluoroacetate) (62) afforded 140 mg; ESI-MS [M+H$^+$]: 527.25.

Example I.B.58

[6-Oxo-5-(2-oxo-2-[4-[2-(2-pyridinylamino)ethyl]-1-piperidinyl}-ethyl)-6,11-dihydro-5H-dibenzo[b,e] azepin-11-yl]acetic acid Hydrolysis of the methyl ester from Example I.B.57 with LiOH in ethanol/H$_2$O afforded 90 mg; ESI-MS [M+K$^+$]=551.2, [M+H$^+$]: 513.25.

Example I.B.59

Methyl [6-oxo-5-(2-oxo-2-{3-[2-(2-pyridinylamino) ethyl]-1-pyrrolidinyl}ethyl)-6,11-dihydro-5H-dibenzo[b,e]azepin-11-yl]-acetate Coupling of 3 with N-[2-(3-pyrrolidinyl)ethyl]-2-pyridinamine (trifluoroacetate) (63) afforded 150 mg; ESI-MS [M+K$^+$]=551.2, [M+H$^+$]: 513.25.

Example I.B.60

[6-oxo-5-(2-oxo-2-{3-[2-(2-pyridinylamino)ethyl]-1-pyrrolidinyl}-ethyl)-6,11-dihydro-5H-dibenzo[b,e] azepin-11-yl]acetic acid Hydrolysis of the methyl ester from Example I.B.59 afforded 150 mg; ESI-MS [M+K$^+$]=537.2, [M+H$^+$]: 499.25.

Example I.B.61

{6-Oxo-5-[2-oxo-2-({4-[(3-phenylpropanoyl)amino] benzyl}amino)-ethyl]-6,1'-dihydro-5H-dibenzo[b,e] azepin-11-yl}acetic acid Coupling of 3 with {4-[(3-phenylpropanoyl)amino]phenyl}-methanamine (hydrochloride) (64) and cleavage of the methyl ester in analogy to Example I.B.1 afforded 100 mg; ESI-MS [M+K$^+$]=600.2, [M+H$^+$]=562.2.

Example I.B.62

(5-{2-[(4-{{[(Benzyloxy)carbonyl]amino}benzyl) amino]-2-oxo-ethyl}-6-oxo-6,11-dihydro-5H-dibenzo[b,e]azepin-11-yl)acetic acid Coupling of 11-(2-tert-butoxy-2-oxoethyl)-6-oxo-6,11-dihydro-5H-dibenzo[b,e]azepin-5-ylacetate (66) with (4-{[(benzyloxy)-carbonyl]amino}phenyl)methanamine (hydrochloride) (65) and TFA cleavage afforded 72 mg; ESI-MS [M+K$^+$)=602.2, [M+H$^+$]: 564.2, 308.0, 102.2.

Example I.B.63

(5-{2-[({5-[Amino(imino)methyl]-2-thienyl]methyl) amino]-2-oxo-ethyl}-6-oxo-6,11-dihydro-5H-dibenzo[b,e]azepin-11-yl)acetic acid (acetate)

a) Coupling of 3 with 5-(aminomethyl)thiophene-2-carbonitrile afforded 1.35 g of a yellowish oil (ESI-MS [M+H$^+$]: 460.15). 1.25 g of this amide in 15 ml of ethanol were mixed with 3 eq. of DIPEA and 2.5 eq. of hydroxylammonium chloride and stirred firstly at RT then at 70° C. for 7 h. After addition of a further 1 eq. each of DIPEA and hydroxylammonium chloride, the mixture was stirred at 50° C. for 4 h. The reaction mixture was then concentrated, diluted with methyl tert-butyl ether and washed with water. The precipitate formed thereby was filtered off with suction, taken up in CH$_2$Cl$_2$, again washed with H$_2$O and evaporated. Stirring of the remaining residue with ethanol/petroleum ether afforded 1 g of a white amorphous solid.)

b) Methyl (5-{2-[({5-[(hydroxyamino)(imino)methyl]-3-thienyl}-methyl)amino]-2-oxoethyl}-6-oxo-6,11-dihydro-5H-dibenzo[b,e]azepin-11-yl)acetate from I.B.63a was introduced into 10 ml of glacial acetic acid and, after addition of 0.69 g of Zn dust, stirred at RT overnight. The reaction mixture was then filtered through Celite and evaporated to dryness (1.3 g);
ESI-MS [M+H$^+$]: 477.15.)

c) Methyl ester I.B.63b (0.54 g) was mixed with 50 ml of 2 N HCl and refluxed for 4 h. The mixture was then evaporated and the resulting crude product was purified by RP-MPLC (60 mg);
ESI-MS [M+H$^+$]=463.18.

Example I.B.64

[5-(5-{[(Benzylamino)carbonyl]amino}pentyl)-6-oxo-6,11-dihydro-5H-dibenzo[b,e]azepin-11-yl]acetic acid a) 3 g (10.13 mmol) of methyl (6-oxo-5,6-dihydro-11H-dibenzo-[b,e]azepin-11-yl)acetate 4a in 100 ml of DMF were mixed with 1.12 g of potassium tert-butoxide and stirred at RT for 30 min. Then 2.95 g of 2-(5-bromopentyl)-1H-isoindole-1,3 (2H)-dione were added and the mixture was stirred for 14 h. After the reaction was complete, the mixture was poured into ice-water and extracted with ethyl acetate, and the organic phase was washed 5× with saturated NaCl solution and dried. The crude product obtained after evaporation was purified by chromatography on silica gel (CH$_2$Cl$_2$) (3.5 g).

b) Hydrolysis with hydrazine hydrate and the usual workup afforded the free amine, which was likewise prepared by chromatography on silica gel (CH$_2$Cl$_2$/CH$_3$OH 0 to 10%). Subsequent reaction with benzyl isocyanate in 55 ml of toluene/DMF 10:1 and the usual workup afforded 260 mg; ESI-MS [M+H$^+$]=500.25.

c) Hydrolysis of the methyl ester under standard conditions afforded 10 g of the title compound; ESI-MS [M+K$^+$]=524.3, [M+H$^+$]=486.2, 243.6.

Example I.B.65

Methyl (5-{2-[(4-aminobenzyl)oxy]ethyl}-6-oxo-6, 11-dihydro-5H-dibenzo[b,e]azepin-11-yl)acetate (hydrochloride)

a) Methyl (6-oxo-5,6-dihydro-11H-dibenzo[b,e]azepin-11-yl)acetate 4a (10 g; 35.55 mmol)—dissolved in 200 ml of THF was slowly added dropwise to 36 mmol of lithium diisopropylamide in 200 ml of THF at 0° C. and then stirred at 0° C. for 1 h. Subsequently about 100 ml of ethylene oxide were added, and the reaction mixture was stored at about 10° C. overnight. The next day, a further approx. 50 ml of ethylene oxide were added, and the mixture was stirred under autogenous pressure at RT for 48 h. For workup, the mixture was poured into saturated $NH_4Cl$ solution and extracted with ethyl acetate and the organic phase was washed with 1 NHCl and then with $H_2O$. The crude product obtained after drying and concentration was purified by chromatography on silica gel (n-heptane/ethyl acetate 0 to 30%) (4 g); ESI-MS $[M+H^+]$=326.

b) A solution of the alcohol I.B.65a (3.2 g; 9.84 mmol) in 50 ml of DMF was added dropwise to a suspension of 0.4 g of NaOH (60%; oil removed with n-pentane) in 100 ml of DMF at 0° C., and the mixture was stirred for about 1 h for complete formation of the anion. Then 9.5 g of 4-nitrobenzyl bromide—dissolved in 50 ml of DMF—were added, and the mixture was stirred at RT for 48 h. For workup, the mixture was poured into saturated $NH_4Cl$ solution and extracted with ethyl acetate, and the organic phase was washed 5× with saturated NaCl solution. The crude product obtained after drying and concentration was purified by chromatography on silica gel (n-heptane/ethyl acetate 0 to 30%) (0.8 g).

c) Reduction of the nitro compound I.B.65b (0.65 g; 1.41 mmol) with $H_2$ and 10% Pd on active carbon in 100 ml of $CH_3OH$ afforded after the workup 650 mg of the title compound;
ESI-MS $[M+K^+]$=469.1, $[M+Na^+]$=453.15, $[M+H^+]$=431.25, 236.6, 216.15.

Example I.B.66

Methyl (5-{2-[(4-{[(benzylamino)carbonyl]amino}benzyl)oxy]ethyl}-6-oxo-6,11-dihydro-5H-dibenzo[b,e]azepin-11-yl)acetate 0.65 g (1.51 mmol) of the methyl ester I.B.65 were converted with 0.23 g of benzyl isocyanate and 0.17 g of triethylamine in 100 ml of $CH_2Cl_2$ into the corresponding benzylurea (purification of the crude product by chromatography on silica gel ($CH_2Cl_2$/ethanol)).
Hydrolysis of the ester in analogy to I.B.1 afforded 22 mg of the title compound; ESI-MS $[M+K^+]$=588.3, $[M+H^+]$=550.25.

Example I.B.67

Methyl {5-[4-(4-{[(benzylamino)carbonyl]amino}phenyl)butyl]-6-oxo-6,11-dihydro-5H-dibenzo[b,e]azepin-11-yl}acetate a) A solution of methyl (6-oxo-5,6-dihydro-11H-dibenzo[b,e]-azepin-11-yl)acetate 4a (0.2 g; 0.72 mmol) in 10 ml of DMF was added dropwise to a suspension of 0.3 g of NaH (60%; oil removed with n-pentane) in 30 ml of DMF at 0° C., and the mixture was then stirred for 1 h for complete formation of the anion. The mixture was subsequently heated to 75° C., and a solution of 4-(4-nitrophenyl)butyl methanesulfonate (0.2 g) in DMF was added. The mixture was stirred at 75° C. for 3 h and, for workup, then poured into saturated $NH_4Cl$ solution and extracted with ethyl acetate, and the organic phase was washed 4× with saturated NaCl solution and concentrated. Alkaline extraction of the crude product obtained in this way afforded 130 mg of methyl {5-[4-(4-nitrophenyl)-butyl]-6-oxo-6,11-dihydro-5H-dibenzo[b,e]azepin-11-yl}acetate; ESI-MS $[M+H^+]$=445.

b) Reduction of the nitro compound in analogy to I.B.65 afforded the corresponding amine (56 mg: ESI-MS $[M+H^+]$=415), which was then converted in analogy to I.B.66 with 0.02 g of benzyl isocyanate and 0.015 g of triethylamine into the benzylurea. Purification of the crude product by chromatography on silica gel afforded 5 mg; ESI-MS $[M+K^+]$=586.2, $[M+H^+]$: 548.3, 274.6.

Example I.B.68

N-{4-[({[5-(carboxymethyl)-6-oxo-6,11-dihydro-5H-dibenzo[b,e]-azepin-11-yl]acetyl}amino)methyl]phenyl}-1H-benzimidazol-2-amine (hydrochloride)

a) 0.5 g (1.26 mmol) of methyl [5-(2-tert-butoxy-2-oxoethyl)-6-oxo-6,11-dihydro-5H-dibenzo[b,e]azepin-11-yl]acetate (2) was hydrolyzed by the standard method with LiOH in ethanol/$H_2O$ to give [5-(2-tert-butoxy-2-oxoethyl)-6-oxo-6,11-dihydro-5H-dibenzo[b,e]azepin-11-yl] acetic acid. Coupling of the acid with N-[4-(aminomethyl)phenyl]-1H-benzimidazol-2-amine (hydrochloride) (47) using HATU as coupling reagent and chromatography of the resulting crude product on silica gel ($CH_2/Cl_2$/$CH_3OH$ 0 to 2%) afforded 170 mg of tert-butyl-[11-(2-{[4-(1H-benzimidazol-2-ylamino)benzyl]-amino}-2-oxoethyl)-6-oxo-6,11-dihydro-5H-dibenzo[b,e]azepin 5-yl]acetate; ESI-MS $[M+H^+]$: 602.

b) TFA cleavage, dissolving of the crude product in $CH_2Cl_2$ and conversion into the corresponding hydrochloride (HCl in diethyl ether; saturated at 0° C.) afforded 25 mg of the title compound; ESI-MS $[M+H^+]$: 546.2.

The following were prepared analogously:

Example I.B.69

[5-(2-{[3-(4-Methyl-1H-imidazol-1-yl)propyl]amino}-2-oxoethyl)-6-oxo-6,11-dihydro-5H-dibenzo[b,e]azepin-11-yl]acetic acid 2 mg; ESI-MS $[M+H^+]$447.

Example I.B.70

[5-(2-{[3-(4-Methyl-1-piperazinyl)propyl]amino}-2-oxoethyl)-6-oxo-6,11-dihydro-5H-dibenzo[b,e]azepin-11-yl]acetic acid 4 mg; ESI-MS $[M+H^+]$=465.

Example I.B.71

(6-Oxo-5-{2-oxo-2-[(3-pyridinylmethyl)amino]ethyl}-6,11-dihydro-5H-dibenzo[b,e]azepin-11-yl)acetic acid 3 mg; ESI-MS [M+H$^+$]=416.

Example I.B.72

[5-(2-{[3-(1H-Imidazol-1-yl)propyl]amino}-2-oxoethyl)-6-oxo-6,11-dihydro-5H-dibenzo[b,e]azepin-11-yl]acetic acid 3 mg; ESI-MS [M+H$^+$]=433.

Example I.B.73

[5-(2-{[1-Methyl-2-(4-morpholinyl)ethyl]amino}-2-oxoethyl)-6-oxo-6,11-dihydro-5H-dibenzo[b,e]azepin-11-yl]acetic acid 3 mg; ESI-MS [M+H$^+$]=452.

Example I.B.74

[5-(2-{[(1-Ethyl-2-pyrrolidinyl)methyl amino]-2-oxoethyl)-6-oxo-6,11-dihydro-5H-dibenzo[b,e]azepin-11-yl)acetic acid 2 mg; ESI-MS [M+H$^+$]=436.

Example I.B.75

(6-Oxo-5-{2-oxo-2-[4-(4-pyridinylmethyl)-1-piperazinyl]ethyl}-6,11-dihydro-5H-dibenzo[b,e]azepin-11-yl]acetic acid 4 mg; ESI-MS [M+H$^+$]=485.

Example I.B.76

[6-Oxo-5-(2-oxo-2-{4-[2-(1-pyrrolidinyl)ethyl]-1-piperazinyl}-ethyl)-6,11-dihydro-5H-dibenzo[b,e]azepin-11-yl]acetic acid 2 mg; ESI-MS [M+H$^+$]=491.

Example I.B.77

[5-(2-{4-[2-(Diethylamino)ethyl]-1-piperazinyl}-2-oxoethyl)-6-oxo-6,11-dihydro-5H-dibenzo[b,e]azepin-11-yl]acetic acid 2 mg; ESI-MS [M+H$^+$]=493.

Example I.B.78

[5-(2-{4-[2-(4-Morpholinyl)ethyl]-1-piperazinyl}-2-oxoethyl)-6-oxo-6,11-dihydro-5H-dibenzo[b,e]azepin-11-yl]acetic acid 4 mg; ESI-MS [M+H$^+$]=507.

Example I.B.79

(6-Oxo-5-{2-oxo-2-[4-(2-pyrimidinyl)-1-piperazinyl]ethyl}-6,11-dihydro-5H-dibenzo[b,e]azepin-11-yl)acetic acid 3 mg; ESI-MS [M+H$^+$]=472.

Example I.B.80

(6-Oxo-5-{2-oxo-2-[(2-pyridinylmethyl)amino]ethyl}-6,11-dihydro-5-H-dibenzo[b,e]azepin-11-yl)acetic acid 2 mg; ESI-MS [M+H$^+$]=416.

Example I.B.81

[5-(2-{[2-(4-Morpholinyl)ethyl]amino}-2-oxoethyl)-6-oxo-6,11-dihydro-5H-dibenzo[b,e]azepin-11-yl]acetic acid 3 mg; ESI-MS [M+H$^+$]=438.

Example I.B.82

[5-(2-{[3-(Dibutylamino)propyl]amino}-2-oxoethyl)-6-oxo-6,11-dihydro-5H-dibenzo[b,e]azepin-11-yl]acetic acid 1 mg; ESI-MS [M+H$^+$]=494.

Example I.B.83

(6-Oxo-5-{2-oxo-2-[4-(4-pyridinyl)-1-piperazinyl]ethyl}-6,11-dihydro-5H-dibenzo[b,e]azepin-11-yl)acetic acid 2 mg; ESI-MS [M+H$^+$]=471.

Example I.B.84

[5-(2-{4-[3-(4-Morpholinyl)propyl]-1-piperazinyl}-2-oxoethyl)-6-oxo-6,11-dihydro-5H-dibenzo[b,e]azepin-11-yl]acetic acid 3 mg; ESI-MS [M+H$^+$]=521.

Example I.B.85

[5-(2-{[3-(2-Methyl-1H-imidazol-1-yl)propyl]amino}-2-oxoethyl)-6-oxo-6,11-dihydro-5H-dibenzo[b,e]azepin-11-yl]acetic acid 1 mg; ESI-MS [M+H$^+$]=447.

Example I.B.86

(6-Oxo-5-{2-oxo-2-[(4-pyridinylmethyl)amino]ethyl}-6,11-dihydro-5H-dibenzo[b,e]azepin-11-yl)acetic acid 1 mg; ESI-MS [M+H$^+$]=416.

Example I.B.87

(5-{2-[(1-Methyl-4-piperidinyl)amino]-2-oxoethyl}-6-oxo-6,11-dihydro-5H-dibenzo[b,e]azepin-11-yl)acetic acid 2 mg; ESI-MS [M+H$^+$]=422.

Example I.B.88

(6-Oxo-5-(2-oxo-2-{[2-(1-piperidinyl)ethyl]amino}ethyl)-6,11-dihydro-5H-dibenzo[b,e]azepin-11-yl]acetic acid 1 mg; ESI-MS [M+H$^+$]=436.

Example I.B.89

(6-Oxo-5-(2-oxo-2-}4-[3-(1-pyrrolidinyl)propyl]-1-piperazinyl}-ethyl)-6,11-dihydro-5H-dibenzo[b,e]azepin-11-yl]acetic acid 1 mg; ESI-MS [M+H$^+$]=505.

Example I.B.90

(5-(2-{4-[2-(Dimethylamino)ethyl]-1-piperazinyl}-2-oxoethyl)-6-oxo-6,11-dihydro-5H-dibenzo[b,e]azepin-11-yl]acetic acid 2 mg; ESI-MS [M+H$^+$]=465,

Example I.B.91

[5-(2-{4-[3-(Dimethylamino)propyl]-1-piperazinyl}-2-oxoethyl]-6-oxo-6,11-dihydro-5H-dibenzo[b,e]azepin-11-yl]acetic acid 1 mg; ESI-MS [M+H$^+$]=479.

Example I.B.92

[5-(2-{4-(2-(Dipropylamino)ethyl]-1-piperazinyl}-2-oxoethyl)-6-oxo-6,11-dihydro-5H-dibenzo[b,e]azepin-11-yl]acetic acid 1 mg; ESI-MS [M+H$^+$]=521.

Example I.B.93

[6-Oxo-5-(2-oxo-2-{4-[2-(1-piperidinyl)ethyl]-1-piperazinyl}-ethyl)-6,11-dihydro-5H-dibenzo[b,e]azepin-11-yl]acetic acid 2 mg; ESI-MS [M+H$^+$]=505.

Example I.B.94

[5-(2-{4-[3-(Dipropylamino)propyl]-1-piperazinyl}-2-oxoethyl)-6-oxo-6,11-dihydro-5H-dibenzo[b,e]azepin-11-yl]acetic acid 2 mg; ESI-MS [M+H$^+$]=535.

Example I.B.95

[5-(2-{[4-(Dibutylamino)butyl]amino}-2-oxoethyl)-6-oxo-6,11-dihydro-5H-dibenzo[b,e]azepin-11-yl]acetic acid 2 mg; ESI-MS [M+H$^+$]=508.

Example I.B.96

[6-Oxo-5-(2-oxo-2-{4-[2-oxo-2-(1-pyrrolidinyl)ethyl]-1-piperazinyl-1}ethyl)-6,11-dihydro-5H-dibenzo[b,e]azepin-11-yl]acetic acid 3 mg; ESI-MS [M+H$^+$]=505.

Example I.B.97

[5-(2-{[3-(Diethylamino)propyl]amino}-2-oxoethyl)-6-oxo-6,11-dihydro-5H-dibenzo[b,e]azepin-11-yl]acetic acid 1 mg; ESI-MS [M+H$^+$]=438.

Example I.B.98

[5-(2-{[2-(Dimethylamino)ethyl]amino}-2-oxoethyl)-6-oxo-6,11-dihydro-5H-dibenzo[b,e]azepin-11-yl]acetic acid 1 mg; ESI-MS [M+H$^+$]=396.

Example I.B.99

[5-(2-{[4-(Dimethylamino)butyl]amino}-2-oxoethyl)-6-oxo-6,11-dihydro-5H-dibenzo[b,e]azepin-11-yl]acetic acid 1 mg; ESI-MS [M+H]+=424.

Example I.B.100

Methyl (3E/z)-3-(5-{2-[(4-{[(benzylamino)carbonyl]amino}benzyl)-amino]-2-oxoethyl}-6-oxo-5,6-dihydro-11H-dibenzo[b,e]azepin-11-yliden)propanoate Coupling of (11Z/E)-11-(3-methoxy-3-oxopropylidene)-6-oxo-6,11-dihydro-5H-dibenzo[b,e]azepin-5-yl)acetate (69) with N-[4-(aminomethyl)phenyl]-N'-benzylurea (trifluoroacetate) (58) using HATU as coupling reagent afforded 65 mg; ESI-MS [M+K$^+$]627.5, [M+H$^+$]=589.3.

Example I.B.101

(3E/Z)-3-(5-{2-[(4-{[(benzylamino)carbonyl]amino}benzyl)amino]-2-oxoethyl}-6-oxo-5,6-dihydro-11H-dibenzo[b,e]azepin-11-ylidene)-propanoic acid Hydrolysis of the methyl ester from Example I.B.100 and purification of the crude product by chromatography on silica gel (CH$_2$Cl$_2$/CH$_3$OH 0 to 20%) afforded 21 mg; ESI-MS [M+K$^+$]=613.2, [M+Na$^+$]=597.2, [M+H$^+$=575.2.

Example I.B.102

Methyl 3-(5-{2-[(4-{[(benzylamino)carbonyl]amino}benzyl)amino]-2-oxoethyl}-6-oxo-6,11-dihydro-5H-dibenzo[b,e]azepin-11-yl)-propanoate Coupling of 11-(3-methoxy-3-oxopropyl)-6-oxo-6,11-dihydro-5H-dibenzo[b,e]azepin-5-yl acetate (70) with N-(4-(aminomethyl)phenyl-N'-benzylurea (trifluoroacetate) (58) using HATU as coupling reagent afforded 140 mg; ESI-MS [M+K$^+$]=629.2, [M+H$^+$]: 591.25, 296.1.

Example I.B.103

3-(5-{2-[(4-{[(Benzylamino)carbonyl]amino}benzyl)amino]-2-oxo-ethyl}-6-oxo-6,11-dihydro-5H-dibenzo[b,e]azepin-11-yl)propanoic acid Hydrolysis of the methyl ester from Example I.B.102 afforded 83 mg of the title compound; ESI-MS [M+K$^+$]=615.2, [M+H$^+$]: 577.25, 289.1.

Example I.B.104

Methyl 3-[6-oxo-5-(2-oxo-2-{[2-(2-pyridinylamino)ethyl]amino}-ethyl)-6,11-dihydro-5H-dibenzo[b,e]azepin-11-yl]propanoate Coupling of 11-(3-methoxy-3-oxopropyl)-6-oxo-6,11-dihydro-5H-dibenzo[b,e]azepin-5-yl acetate (70) with N$^1$-(2-pyridinyl)-1,2-ethanediamine and purification of the crude product by chromatography on silica gel (CH$_2$Cl$_2$/CH$_3$OH 0 to 5%) afforded 3 mg; ESI-MS [M+H$^+$]: 473.

Example I.B.105

3-[6-Oxo-5-(2-oxo-2-{[2-(2-pyridinylamino)ethyl]amino}ethyl)-6,11-dihydro-5H-dibenzo[b,e]azepin-11-yl]propanoic acid (Na salt)

Hydrolysis of the methyl ester from Example I.B.102 afforded 3 mg of the title compound; ESI-MS [M+K$^+$]=497.1, [M+H$^+$]: 459.15.

Example I.B.106

Methyl (2E/Z)-(5-{2-[(4-{[(benzylamino)carbonyl]amino}benzyl)-amino]-2-oxoethyl}-4-oxo-4,5-dihydro-10H-thieno[3,4-c][1]benzazepin-10-ylidene)ethanoate Coupling of (10E/Z)-10-(2-methoxy-2-oxoethylidene)-4-oxo-4H-thieno[3,4-c][1]benzazepin-5 (10H)-yl acetate (71) with N-[4-(aminomethyl)phenyl]-N'-benzylurea (trifluoroacetate) (58) afforded 98 mg; ESI-MS [M+K$^+$]=619.2, [M+H$^+$]=581.15, 291.1.

Example I.B.107

(2E)-(5-{2-[(4-{[(Benzylamino)carbonyl]amino}benzyl)amino]-2-oxoethyl}-4-oxo-4,5-dihydro-10H-thieno[3,4-c][1]benzazepin-10-ylidene)ethanoic acid Hydrolysis of the methyl ester I.B.106 afforded 24 mg of the title compound; ESI-MS [M+K$^+$]=605.15, [M+H$^+$]: 567.15, 284.2.

Example I.B.108

Methyl [5-(2-{[4-(1H-benzimidazol-2-ylamino)benzyl]amino}2-oxoethyl)-4-oxo-5,10-dihydro-4H-thieno[3,4-c][1]benzazepin-10-yl]acetate Coupling of 10-(2-methoxy-2-oxoethyl)-4-oxo-4H-thieno[3,4-c]-[1]benzazepin-5 (10H)-yl acetate (72) with N-[4-(aminomethyl)phenyl]-1H-benzimidazol-2-amine (hydrochloride) (47) and purification of the crude product by chromatography on silica gel (CH$_2$Cl$_2$/CH$_3$OH 0 to 2%) afforded 47 mg; ESI-MS [M+H$^+$]: 566.2.

Example I.B.109

[5-(2-{[4-(1H-Benzimidazol-2-ylamino)benzyl]amino}-2-oxoethyl)-4-oxo-5,10-dihydro-4H-thieno[3,4-c][1]benzazepin-10-yl]acetate Hydrolysis of the methyl ester I.B.108 afforded 9 mg of the title compound; ESI-MS [M+H$^+$]: 552.22.

Example I.B.110

Methyl (2E/Z)-(4-{2-[(4-{[(benzylamino)carbonyl]amino}benzyl)-amino]-2-oxoethyl}-5-oxo-4,5-dihydro-9H-dithieno[3,4-b:3,4-e]azepin-9-ylidene)ethanoate Coupling of (9E/Z)-9-(2-methoxy-2-oxoethylidene)-5-oxo-9H-dithieno[3,4-b:3,4-e]azepin-4 (5H)-yl acetate (73) with N-[4-(aminomethyl)phenyl]-N'-benzylurea (trifluoroacetate) (58) afforded 55 mg of the title compound; ESI-MS [M+K$^+$]=625.05, [M+H$^+$]: 587.15.

Example I.B.111

(2E/Z)-(4-{2-[(4-{[(benzylamino)carbonyl]amino}benzyl)amino]-2-oxoethyl}-5-oxo-4,5-dihydro-9H-dithieno[3,4-b:3,4-e]azepin-9-ylidene)ethanoic acid Hydrolysis of the methyl ester I.B.110 afforded 10 mg of the title compound; ESI-MS [M+K$^+$]=611.0, [M+H$^+$]: 573.2, 129.15, 100.2.

Example I.B.112

Methyl [4-(2-{[4-(1H-Benzimidazol-2-ylamino)benzyl]amino}-2-oxoethyl)-5-oxo-4,5-dihydro-9H-dithieno[3,4-b:3,4-e]azepin-9-yl]-acetate Coupling of (9-(2-methoxy-2-oxoethyl)-5-oxo-9H-dithieno[-3,4-b:3,4-e]azepin-4 (5H)-yl acetate (74) with N-[4-(aminomethyl)phenyl]-1H-benzimidazol-2-amine (hydrochloride) (47) afforded 21 mg of the title compound; ESI-MS [M+H$^+$]: 573.

Example I.B.113

Sodium [4-(2-{[4-(1H-benzimidazol-2-ylamino)benzyl]amino}-2-oxoethyl)-5-oxo-4,5-dihydro-9H-dithieno[3,4-b:3,4-e]azepin-9-yl]acetate Hydrolysis of the methyl ester I.B.112 afforded 10 mg of the title compound; ESI-MS [M+H$^+$]: 558.05, 502.1.

Example I.B.114

5-{[4-({[4-(1H-Benzimidazol-2-yl)benzyl]amino}carbonyl)-1,3-thiazol-2-yl]methyl}-6-oxo-6,11-dihydro-5H-dibenzo[b,e]azepin-11-yl acetate Coupling of 2-{[1-(2-tert-butoxy-2-oxoethyl)-6-oxo-6,11-dihydro-5H-dibenzo[b,e]azepin-5-yl]methyl}-1,3-thiazole-4-carboxylic acid (75) with [4-(1H-benzimidazol-2-yl)benzyl]methylamine from building block 14 afforded 15 mg of the title compound ESI-MS [M+H$^+$]: 614.25.

The following were prepared in analogy to I.B.114:

Example I.B.115

6-Oxo-5-{[4-({4-[(2-pyridinylamino)methyl]-1-piperidinyl}-carbonyl)-1,3-thiazol-2-yl]methyl}-6,11-dihydro-5H-dibenzo[b,e]-azepin-11-yl acetate 60 mg; ESI-MS [M+H$^+$]: 528.25.

Example I.B.116

5-[(4-{[4-{[(Benzylamino)carbonyl]amino}benzyl)amino]-carbonyl}-1,3-thiazol-2-yl)methyl]-6-oxo-6,11-dihydro-5H-dibenzo-[b,e]azepin-11-yl acetate 25 mg; ESI-MS [M+H$^+$]: 646.25.

Example I.B.117

6-Oxo-5-({4-[({4-[(2-pyridinylamino)methyl]benzyl}amino)-carbonyl]-1,3-thiazol-2-yl}methyl)-6,11-dihydro-5H-debenzo-[b,e]azepin-11-yl acetate 15 mg; ESI-MS [M+H$^+$]: 604.15.

Example I.B.118

6-Oxo-5-[(4-{[({4-[(2-pyridinylamino)methyl]-2-thienyl}methyl)-amino]carbonyl}-1,3-thiazol-2-yl)methyl]-6,11-dihydro-5H-dibenzo [b,e]azepin-11-yl acetate 70 mg; ESI-MS [M+H$^+$]: 610.15.

II. BIOLOGICAL EXAMPLES

Example 1

Integrin $\alpha_v\beta_3$ Assay

Integrin $\alpha_v\beta_3$ antagonists were identified and assessed by using an assay system based on competition between the natural integrin $\alpha_v\beta_3$ ligand vitronectin and the test substance for binding to solid phase-bound integrin $\alpha_v\beta_3$.

Procedure
  Coat microtiter plates with 250 ng/ml integrin $\alpha_v\beta_3$ in 0.05 M NaHCO$_3$ pH 9.2; 0.1 ml/well;
  saturate with 1% milk powder/assay buffer; 0.3 ml/well; 0.5 h/RT
  wash 3× with 0.05% Tween 20/assay buffer
  test substance in 0.1% milk powder/assay buffer, 50 µl/well+0 µg/ml or 2 µg/ml human vitronectin (Boehringer Ingelheim T007) in 0.1% milk powder/assay buffer, 50 µl/well; 1 h/RT
  wash 3× with 0.05% Tween 20/assay buffer
  1 µg/ml anti-human vitronectin antibody coupled to peroxidase (Kordia SAVN-APHRP) in 0.1% milk powder/assay buffer; 0.1 ml/well; 1 h/RT
  wash 3× with 0.05% Tween 20/assay buffer
  0.1 ml/well peroxidase substrate
  stop reaction with 0.1 ml/well 2 M H$_2$SO$_4$
  measure absorption at 450 nm
  Integrin $\alpha_v\beta_3$: human placenta is solubilized with Nonidet, and integrin $\alpha_v\beta_3$ is affinity-purified on a GRGDSPK matrix (elution with EDTA). Contamination by integrin $\alpha_{IIb}\beta_3$ and human serum albumin, and the detergent and EDTA, are removed by anion exchange chromatography.
  Assay buffer: 50 mM Tris pH 7.5; 100 mM NaCl; 1 mM CaCl$_2$; 1 mM MgCl$_2$; 10 µM MnCl$_2$
  Peroxidase substrate: mix 0.1 ml of TMB solution (42 mM TMB in DMSO) and 10 ml of substrate buffer (0.1 M Na acetate, pH 4.9) and then add 14.7 µl of 3% H$_2$O$_2$.

Various dilutions of the test substances are used in the assay, and the IC$_{50}$ values are determined (concentration of the antagonist at which 50% of the ligand is displaced). The compounds of Examples I.B.37, I.B.46, I.B.52 and I.B.118 showed the best results in this.

Example 2

Integrin $\alpha_{IIb}\beta_3$ Assay

The assay is based on competition between the natural integrin $\alpha_{IIb}\beta_3$ ligand fibrinogen and the test substance for binding to integrin $\alpha_{IIb}\beta_3$.

Procedure
  coat microtiter plates with 10 µg/ml fibrinogen (Calbiochem 341578) in 0.05 M NaHCO$_3$ pH 9.2; 0.1 ml/well;
  saturate with 1% BSA/PBS; 0.3 ml/well; 30 min/RT
  wash 3× with 0.05% Tween 20/PBS
  test substance in 0.1% BSA/PBS; 50 µl/well+200 µg/ml integrin $\alpha_{IIb}\beta_3$ (Kordia) in 0.1% BSA/PBS; 50 µl/well; 2 to 4 h/RT
  wash 3× as above
  biotinylated anti-integrin $\alpha_{IIb}\beta_3$ antibody (Dianova CBL 130 B); 1:1000 in 0.1% BSA/PBS; 0.1 ml/well; 2 to 4 h/RT
  wash 3× as above
  streptavidin-peroxidase complex (B.M. 1089153) 1:10,000 in 0.1% BSA/PBS; 0.1 ml/well; 30 min/RT
  wash 3× as above
  0.1 ml/well peroxidase substrate
  stop reaction with 0.1 ml/well 2 M H$_2$SO$_4$
  measure the absorption at 450 nm
  Peroxidase substrate: mix 0.1 ml of TMB solution (42 mM TMB in DMSO) and 10 ml of substrate buffer (0.1 M Na acetate pH 4.9) and then add 14.7 µl of 3% H$_2$O$_2$ Various dilutions of the test substances are used in the assay, and the IC$_{50}$ values are determined (concentration of the antagonist at which 50% of the ligand is displaced).

The selectivity of the substances can be determined by comparing the IC$_{50}$ values in the integrin $\alpha_{IIb}\beta_3$ and integrin $\alpha_v\beta_3$ assays.

Example 3

CAM Assay

The CAM (chorioallantoic membrane) assay is a generally accepted model for assessing the in vivo activity of integrin $\alpha_v\beta_3$ antagonists. It is based on the inhibition of angiogenesis and neovascularization of tumor tissue (Am. J. Pathol. 1975, 79, 597–618; Cancer Res. 1980, 40, 2300–2309; Nature 1987, 329, 630). The procedure is analogous to the prior art. The growth of chicken embryo blood vessels and of transplanted tumor tissue is easy to follow and assess.

Example 4

Rabbit Eye Assay

It is possible in this in vivo model to follow and assess in analogy to Example 3 the inhibition of angiogenesis and neovascularization in the presence of integrin $\alpha_v\beta_3$ antagonists. The model is generally accepted and is based on growth of blood vessels starting from the edge into the cornea of the rabbit eye (Proc. Natl. Acad. Sci. USA. 1994, 91, 4082–4085; Science 1976, 193, 70–72). The procedure is analogous to the prior art.

We claim:
1. A compound of the formula I

B—G—L  I where B, G and L have the following meanings:
L is a structural element of the formula $I_L$

—U—T  $I_L$ where
T is COOH, COO—$C_{1-8}$-alkyl or COO-benzyl, and
—U— is —$(X_L)_a$—$(CR_L^1R_L^2)_b$— or =$CR_L^1$—,
where
a is 0 or 1,
b is 0, 1 or 2,
$X_L$ is $CR_L^3R_L^4$ or oxygen
$R_L^1$, $R_L^2$, $R_L^3$ and $R_L^4$
are, independently of one another, hydrogen, a halogen radical, a branched or unbranched, optionally substituted $C_1$–$C_4$-alkyl, $C_1$–$C_4$-alkoxy radical, or in each case independently of one another, two radicals $R_L^1$ and $R_L^2$ or $R_L^3$ and $R_L^4$ or, where appropriate, $R_L^1$ and $R_L^3$ together are an optionally substituted 3- to 7-membered cycloalkyl radical G is

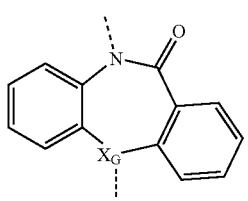

where
the structural element G can be incorporated in both orientations, and where structural element G is connected to structural element L or B via $X_G$, wherein $X_G$; is carbon and where the rings fused on the 7-membered ring of the structural element G are optionally substituted,
B is a structural element of the formula $I_B$

A—E—  $I_B$ where A and E have the following meanings:
A is a structural element selected from the group of structural elements of the formulae $I_A^1$, $I_A^4$, $I_A^7$, $I_A^8$, $I_A^{14}$:

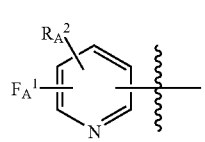  $I_A^1$

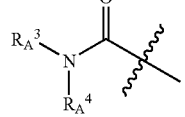  $I_A^4$

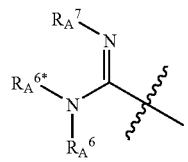  $I_A^7$

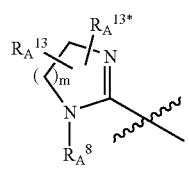  $I_A^8$ and

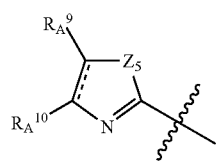  $I_A^{14}$ where
m is 1, 2 or 3
$R_A^1$ and $R_A^2$
are, independently of one another, hydrogen, CN, halogen, a branched or unbranched, optionally substituted $C_1$–$C_6$-alkyl or CO—$C_1$–$C_6$-alkyl radical or an optionally substituted aryl, arylalkyl, hetaryl, hetarylalkyl or $C_3$–$C_7$-cycloalkyl radical or a radical CO—O—$R_A^{14}$, O—$R_A^{14}$, S—$R_A^{14}$, $NR_A^{15}R_A^{16}$, CO—$NR_A^{15}R_A^{16}$ or $SO_2NR_A^{15}R_A^{16}$ or the two $R_A^1$ and $R_A^2$ radicals together are a fused-on, optionally substituted 5- or 6-membered, unsaturated or aromatic carbocyclic or heterocyclic system which may contain up to three heteroatoms selected from the group of O, N and S,
$R_A^{13}$ and $R_A^{13*}$
are, independently of one another, hydrogen, CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, $NR_A^{15}R_A^{16}$ or CO—$NRA^{15}R_A^{16}$ radical, where $R_A^{14}$ is hydrogen, a branched or unbranched, optionally substituted $C_1$–$C_6$-alkyl, alkylene-$C_1$–$C_4$-alkoxy, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_A^{15}$ and $R_A^{16}$, are, independently of one another, hydrogen, a branched or unbranched, optionally substituted $C_1$–$C_6$-alkyl, CO—$C_1$–$C_6$-alkyl, $SO_2$—$C_1$–$C_6$-alkyl, COO—$C_1$–$C_6$-alkyl, arylalkyl, COO-alkylene-aryl, $SO_2$-alkylene-aryl or hetarylalkyl radical or an optionally substituted $C_3$–$C_7$-cycloalkyl, aryl, CO-aryl, $SO_2$-aryl, hetaryl or CO-hetaryl radical, $R_A^3$ and $R_A^4$ are, independently of one another, hydrogen, —$(CH_2)_n$—$(X_A)_j$—$R_A^{12}$, or the two radicals together are a 3- to 8-membered, saturated, unsaturated or aromatic N heterocyclic system which may additionally contain two other identical or different heteroatoms O, N or S, it being possible for the ring optionally to be substituted or for another, optionally substituted, saturated, unsaturated or aromatic ring to be fused onto this ring, where n is 0, 1, 2 or 3, j is 0 or 1, $X_A$ is —$SO_2$—, —S—, —O—, —CO—, —O—CO—, —CO—O—, —CO—$N(R_A^{12})$—, —$N(R_A^{12})$—CO—, —$N(R_A^{12})$—$SO_2$— or —$SO_2$—$N(R_A^{12})$— and $R_A^{12}$ is hydrogen, a branched or unbranched, optionally substituted $C_1$–$C_6$-alkyl, $C_1$–$C_4$-alkoxy, —O-alkylene-aryl or —O-aryl radical, an amino radical with primary or, where appropriate, secondary or tertiary Substitution, an optionally $C_1$–$C_4$-alkyl- or aryl-substituted $C_2$–$C_6$-alkynyl or $C_2$–$C_6$-alkenyl radical or a 3- to 6-membered, saturated or unsaturated heterocyclic system which is substituted by up to three identical or different radicals and which may contain up to three different or identical heteroatoms O, N, S, $C_3$–$C_7$-cycloalkyl, aryl or hetaryl radical, it being possible for two radicals together to be a fused-on, saturated, unsaturated or aromatic carbocyclic or heterocyclic system which may contain up to three different or identical heteroatoms O, N, S, and the ring may optionally be substituted, or another, optionally substituted, saturated, unsaturated or aromatic ring may be fused onto this ring, $R_A^6$ and $R_A^{6*}$ are hydrogen, a branched or unbranched, optionally substituted $C_1$–$C_4$-alkyl, —CO—O—$C_1$–$C_4$-alkyl, arylalkyl, —CO—O-alkylene-aryl, —CO—O-allyl, —CO—$C_1$–$C_4$-alkyl, —CO-alkylene-aryl, $C_3$–$C_7$-cycloalkyl or —CO-allyl radical or the two radicals $R_A^6$ and $R_A^{6*}$ in the structural element $I_A^7$ together are an optionally substituted, saturated, unsaturated or aromatic heterocyclic system which may, in addition to the ring nitrogen, contain up to two further different or identical heteroatoms O, N, S, $R_A^7$ is hydrogen, —OH, —CN, —$CONH_2$, a branched or unbranched, optionally substituted $C_1$–$C_4$-alkyl, $C_1$–$C_4$-alkoxy, $C_3$–$C_7$-cycloalkyl or —O—CO—$C^1$–$C_4$-alkyl radical, or an optionally substituted arylalkyl, —O-alkylene-aryl, —O—CO-aryl, —O—CO-alkylene-aryl or —O—CO-allyl radical, or the two radicals $R_A^6$ and $R_A^7$ together are an optionally substituted, unsaturated or aromatic heterocyclic system which may, in addition to the ring nitrogen, contain up to two further different or identical heteroatoms O, N, S, $R_A^8$ is hydrogen, a branched or unbranched, optionally substituted $C_1$–$C_4$-alkyl, CO—$C_1$–$C_4$-alkyl, $SO_2$—$C_1$–$C_4$-alkyl or CO—O—$C_1$–$C_4$-alkyl radical or an optionally substituted aryl, CO-aryl, $SO_2$-aryl, CO—O-aryl, CO-alkylene-aryl, $SO_2$-alkylene-aryl, CO—O-alkylene-aryl or alkylene-aryl radical, $R_A^9$ and $R_A^{10}$ are, independently of one another, hydrogen, —CN, halogen, a branched or unbranched, optionally substituted $C_1$–$C_6$-alkyl radical or an optionally substituted aryl, arylalkyl, hetaryl, $C_3$–$C_7$-cycloalkyl radical or a CO—O—$R_A^{14}$, O—$R_A^{14}$, S—$R_A^{14}$, $NR_A^{15}R_A^{16}$ or CO—$NR_A^{15}R_A^{16}$ radical, or the two $R^{A9}$ and $R_A^{10}$ radicals in the structural element $I_A^{14}$ together are a 5- to 7-membered saturated, unsaturated or aromatic carbocyclic or heterocyclic system which may contain up to three different or identical heteroatoms O, N, S and is optionally substituted by up to three identical or different radicals, $Z^5$ is $NR_A^8$, oxygen or sulphur, and E is a spacer structural element which connects structural element A to structural element G covalently, wherein the spacer structural element E is composed of two to four partial structural elements selected from the group of $E^1$ and $E^2$, the partial structural elements being linked in any sequence, and $E^1$ and $E^2$ having the following meanings:

$E^1$ is a partial structural element of the formula $I_{E1}$ $$—(X_E)_i—(CH_2)_c—CR_E^1R_E^2—(CH_2)_d—(Y_E)_f— \qquad I_{E1}$$

and $E^2$ is a partial structural element of the formula $I_{E2}$ $$(NR_E^3)_e—(CR_E^4R_E^5)_f—(Q_E)_k—(CR_E^6R_E^7)_g—(NR_E^8)_h— \qquad I_{E2}$$

where c, d, f and g are, independently of one another, 0, 1 or 2, e, h, i, k and l, are, independently of one another, 0 or 1, $X_E$ and $Q_E$ are, independently of one another, CO, CO—$NR_E^9$, S, SO, $SO_2$, $SO_2NR_E^9$, CS, CS—$NR_E^9$, CS—O, CO—O, O—CO, O, ethynyl, $CR_E^{10}$—O—$CR_E^{11}$, $CR_E^{10}R_E^{11}$—, C(=$CR_E^{10}R_E^{11}$), $CR_E^{10}$=$CR_E^{11}$—, $CR_E^{11}(OR_E^{12})$—$CR_E^{11}$, $CR_E^{10}$—$CR_E^{11}(OR_E^{12})$ or an optionally substituted 4- to 11-membered mono- or polycyclic aliphatic or aromatic hydrocarbon which may contain up to 6 double bonds and up to 6 heteroatoms selected from the group of N, O, S, $Y_E$ is —CO—, —$NR_E^9$—CO—, —SO—, —$SO_2$—, —$NR_E^9$—$SO_2$—, —CS—, —$NR_E^9$—CS—, —O—CS— or —O—CO—

$R_E^1$, $R_E^2$, $R_E^4$, $R_E^5$, $R_E^6$ and $R_E^7$ are, independently of one another, hydrogen, halogen, a hydroxyl group, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical, a —(CH₂)ᵥᵥ—$R_E^{13}$ radical, an optionally substituted $C_3$–$C_7$-cycloalkyl, aryl, arylalkyl, hetaryl, hetarylalkyl, O-aryl or O-alkylene-aryl radical, or, independently of one another, in each case two radicals $R_E^1$ and $R_E^2$ or $R_E^4$ and $R_E^5$ or $R_E^6$ and $R_E^7$ together are a 3- to 7-membered, optionally substituted, saturated or unsaturated carbocyclic system, where w is 0,1,2, 3 or 4, $R_E^3$, $R_E^8$ and $R_E^9$
are, independently of one another, hydrogen, a branched or unbranched, optionally substituted $C_1$–$C_6$-alkyl, CO—$C_1$–$C_6$-alkyl, CO—O—$C_1$–$C_6$-alkyl or SO₂—$C_1$–$C_6$-alkyl radical or an optionally substituted $C_3$–$C_7$-cycloalkyl, CO—O-alkylene-aryl, CO-alkylene-aryl, CO-aryl, SO₂-aryl, CO-hetaryl or SO₂-alkylene-aryl radical, $R_E^{10}$ and $R_E^{11}$
are, independently of one another, hydrogen, a hydroxyl group, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_E^{12}$ is hydrogen, a branched or unbranched, optionally substituted $C_1$–$C_6$-alkyl, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_E^{13}$ is hydrogen, a hydroxyl group, a branched or unbranched, optionally substituted $C_1$–$C_6$-alkyl, $C_1$–$C_4$-alkoxy, -arylalkyl, —O-alkylene-aryl or —O-aryl radical, an amino radical with primary or, where appropriate, secondary or tertiary substitution, be an optionally $C_1$–$C_4$-alkyl- or aryl-substituted $C_2$–$C_6$-alkynyl or $C_2$–$C_6$-alkenyl radical, a $C_5$–$C_{12}$-bicycloalkyl, $C_6$–$C_{18}$-tricycloalkyl radical, a CO—O—$R^{414}$ radical, or a 3- to 6-membered, saturated or unsaturated heterocyclic system which is substituted by up to three identical or different radicals and which may contain up to three different or identical heteroatoms O, N, S, $C_3$–$C_7$-cycloalkyl, aryl or hetaryl radical, it being possible for two radicals together to be a fused-on, saturated, unsaturated or aromatic carbocyclic or heterocyclic system which may contain up to three different or identical heteroatoms O, N, S, and the ring may optionally be substituted or another, optionally substituted, saturated, unsaturated or aromatic ring may be fused onto this ring, wherein the optional substituents are selected from the group consisting of —NO₂, —NH₂, —OH, —CN, —COOH, —O—CH₂—COOH, halogen, a branched or unbranched, $C_1$–$C_4$-alkyl, $C_1$–$C_4$-haloalkyl —CO—O—$C_1$–$C_4$-alkyl, $C_3$–$C_6$-cycloalkyl, $C_1$–$C_4$-alkoxy, $C_1$–$C_4$-alkylthio, —NH—CO—O—$C_1$–$C_4$-alkyl, —O—CH₂—COO—$C_1$–$C_4$-alkyl, —NH—CO—$C_1$–$C_4$-alkyl, —CO—NH—$C_1$–$C_4$-alkyl, —NH—SO₂—$C_1$–$C_4$-alkyl, —SO₂—NH—$C_1$–$C_4$-alkyl, —N($C_1$–$C_4$-alkyl)₂, —NH—$C_1$–$C_4$-alkyl, —SO₂—$C_1$–$C_4$-alkyl —NH—CO-aryl, CO—NH-aryl, —NH—CO—O-aryl, —NH—CO—O-alkylene-aryl, —NH—SO₂-aryl, SO₂—NH-aryl, —CO—NH-benzyl, —NH—SO₂-benzyl, —SO₂—NH-benzyl, —SO₂—NR²R³ or —CO—NR²R³, where the radicals R² and R³, independently of one another, have the meaning of $R_L^5$, or the two radicals R² and R³ together are a 3- to 6-membered, optionally substituted, saturated, unsaturated or aromatic heterocyclic system which, in addition to the ring nitrogen, contains up to three other different or identical heteroatoms O, N, S, and optionally two radicals substituting this heterocyclic system together are a fused or saturated, unsaturated or aromatic carbocyclic or heterocyclic system which contains up to three different or identical heteroatoms O, N, S, and the ring can optionally be substituted or another, optionally substituted ring can be fused onto this ring or a physiologically tolerated salt, enantiomerically pure, diastereomerically pure or tautomeric form thereof.

2. A compound as claimed in claim 1, wherein the spacer structural element E used is a structural element of the formula $I_{E1E2}$

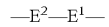

$$—E^2—E^1—  \qquad I_{E1E2}$$

and $E^1$ and $E^2$ have the following meanings:

$E^1$ is a partial structural element of the formula $I_{E1}$

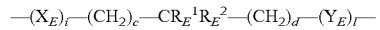

$$—(X_E)_i—(CH_2)_c—CR_E^1R_E^2—(CH_2)_d—(Y_E)_j— \qquad I_{E1}$$

and $E^2$ is a partial structural element of the formula $I_{E2}$

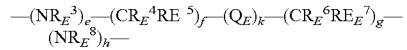

$$—(NR_E^3)_e—(CR_E^4RE^5)_f—(Q_E)_k—(CR_E^6RE_E^7)_g—(NR_E^8)_h— \qquad I_{E2}$$

where c, d, f and g
are, independently of one another, 0, 1 or 2 e, h, i, k and l
are, independently of one another, 0 or 1, $X_E$ and $Q_E$
are, independently of one another, CO, CO—$NR_E^9$, S, SO, SO₂, SO₂$NR_E^9$, CS, CS—$NR_E^9$, CS—O, CO—O, O—CO, O, ethynyl, $CR_E^{10}$—O—$CR_E^{11}$, $CR_E^{10}R_E^{11}$, C(=$CR_E^{10}R_E^{11}$), $CR_E^{10}CR_E^{11}$, $CR_E^{10}(OR_E^{12})$—$CR_E^1$, $CR_E^{11}$—$CR_E^{11}$—($OR_E^{12}$) or an optionally substituted 4- to 11-membered mono- or polycyclic aliphatic or aromatic hydrocarbon which may contain up to 6 double bonds and up to 6 heteroatoms selected from the group of N, O, S, YE is —CO—, —$NR_E^9$—CO—, —SO—, —SO₂—, —$NR_E^9$—SO₂—, —CS—, —$NR_E^9$—CS—, —O—CS— or —O—CO—

$R_E^1$, $R_E^2$, $R_E^4$–$R_E^5$, $R_E^6$ and $R_E^7$
are, independently of one another, hydrogen, halogen, a hydroxyl group, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical, a —(CH₂)ᵥᵥ—$R_E^{13}$ radical, an optionally substituted $C_3$–$C_7$-cycloalkyl, aryl, arylalkyl, hetaryl, hetarylalkyl, O-aryl or O-alkylene-aryl radical, or, independently of one another, in each case two radicals $R_E^1$ and $R_E^2$ or $R_E^4$ and $R_E^5$ or $R_E^6$ and $R_E^7$ together are a 3- to 7-membered, optionally substituted, saturated or unsaturated carbocyclic system, where w is 0, 1, 2, 3 or 4, $R_E^3$, $R_E^8$ and $R_E^9$
are, independently of one another, hydrogen, a branched or unbranched, optionally substituted $C_1$–$C_6$-alkyl, CO—$C_1$–$C_6$-alkyl, CO—O—$C_1$–$C_6$-alkyl or SO₂—$C_1$–$C_6$-alkyl radical or an optionally substituted $C_3$–$C_7$-cycloalkyl, CO—O-alkylene-aryl, CO-alkylene-aryl, CO-aryl, SO₂-aryl, CO-hetaryl or SO₂-alkylene-aryl radical, $R_E^{10}$ and $R_E^{11}$
are, independently of one another, hydrogen, a hydroxyl group, a branched or unbranched, optionally substituted $C_1$–$C_6$-alkyl, $C_1$–$C_4$-alkoxy, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, $R_E^{12}$ is hydrogen, a branched or unbranched, optionally substituted $C_1$–$C_6$-alkyl, $C_2$–$C_6$-alkenyl, $C_2$–$C_6$-alkynyl or alkylene-cycloalkyl radical or an optionally substituted $C_3$–$C_7$-cycloalkyl, aryl, arylalkyl, hetaryl or hetarylalkyl radical, and $R_E^{13}$ is hydrogen, a hydroxyl group, a branched or unbranched, optionally substituted $C_1$–$C_6$-alkyl, $C_1$–$C_4$-alkoxy, arylalkyl, —O-alkylene-aryl or —O-aryl radical, an amino radical with primary or, where appropriate, secondary or tertiary substitution, an optionally $C_1$–$C_4$-alkyl- or aryl-substituted $C_2$–$C_6$-alkynyl or $C_2$–$C_6$-alkenyl radical, a $C_5$–$C_{12}$-bicycloalkyl, $C_6$–$C_{18}$tricycloalkyl radical, a CO—O—$R_A^{14}$ radical, or a 3- to 6-membered, saturated or unsaturated heterocyclic system which is substituted by up to three identical or different radicals and which may contain up to three different or identical heteroatoms O, N, S, $C_3$–$C_7$-cycloalkyl, aryl or hetaryl radical, it being possible for two radicals together to be a fused-on, saturated, unsaturated or aromatic carbocyclic or heterocyclic system which may contain up to three different or identical heteroatoms O, N, S, and the ring may optionally be substituted, or another, optionally substituted, saturated, unsaturated or aromatic ring may be fused onto this ring, wherein the optional substituents are selected from the group consisting of —$NO_2$, —$NH_2$, —OH, —CN, —COOH, —O—$CH_2$—COOH, halogen, a branched or unbranched, $C_1$–$C_4$-alkyl, $C_1$–$C_4$-haloalkyl —CO—O—$C_1$–$C_4$-alkyl, $C_3$–$C_6$-cycloalkyl, $C_1$–$C_4$-alkoxy, $C_1$–$C_4$-alkylthio, —NH—CO—O—$C_1$–$C_4$-alkyl, —O—$CH_2$—COO—$C_1$–$C_4$-alkyl, —NH—CO—$C_1$–$C_4$-alkyl, —CO—NH—$C_1$–$C_4$-alkyl, —NH—$SO_2$—$C_1$–$C_4$-alkyl, —$SO_2$—NH—$C_1$–$C_4$-alkyl, —N($C_1$–$C_4$-alkyl)$_2$, —NH—$C_1$–$C_4$-alkyl, —$SO_2$—$C_1$–$C_4$-alkyl —NH—CO-aryl, CO—NH-aryl, —NH—CO—O-aryl, —NH—CO—O-alkylene-aryl, —N H—$SO_2$-aryl, $SO_2$—N H-aryl, —CO—N H-benzyl, —N H—$SO_2$-benzyl, —$SO_2$—NH-benzyl, —$SO_2$—$NR^2R^3$ or —CO—$NR^2R^3$, where the radicals $R^2$ and $R^3$, independently of one another, have the meaning of $R_L^5$, or the two radicals $R^2$ and $R^3$ together are a 3 to 6-membered, optionally substituted, saturated, unsaturated or aromatic heterocyclic system which, in addition to the ring nitrogen, contains up to three other different or identical heteroatoms O, N, S, and optionally two radicals substituting this heterocyclic system together are a fused or saturated, unsaturated or aromatic carbocyclic or heterocyclic system which contains up to three different or identical heteroatoms O, N, S, and the ring can optionally be substituted or another, optionally substituted ring can be fused onto this ring.

3. A pharmaceutical preparation for oral or parenteral use, comprising at least one compound as claimed in claim 1 in addition to conventional pharmaceutical excipients.

* * * * *